US010069967B2

(12) United States Patent
Hodge

(10) Patent No.: US 10,069,967 B2
(45) Date of Patent: *Sep. 4, 2018

(54) TELECOMMUNICATION CALL MANAGEMENT AND MONITORING SYSTEM WITH VOICEPRINT VERIFICATION

(71) Applicant: **GLOBAL TEL*LINK CORP.**, Reston, VA (US)

(72) Inventor: Stephen Lee Hodge, Aubry, TX (US)

(73) Assignee: **Global Tel*Link Corporation**, Reston, VA (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/865,658

(22) Filed: Sep. 25, 2015

(65) Prior Publication Data
US 2016/0021242 A1 Jan. 21, 2016

Related U.S. Application Data

(63) Continuation of application No. 14/613,153, filed on Feb. 3, 2015, which is a continuation of application
(Continued)

(51) Int. Cl.
*H04M 3/00* (2006.01)
*H04M 3/38* (2006.01)
(Continued)

(52) U.S. Cl.
CPC ........... *H04M 3/382* (2013.01); *A61K 31/435* (2013.01); *A61K 31/44* (2013.01); *A61K 31/505* (2013.01);
(Continued)

(58) Field of Classification Search
CPC .... A61K 31/435; A61K 31/44; A61K 31/505; G06F 17/30259; G06F 17/30268;
(Continued)

(56) References Cited

U.S. PATENT DOCUMENTS 4,054,756 A 10/1977 Comella
4,191,860 A 3/1980 Weber
(Continued)

FOREIGN PATENT DOCUMENTS

EP 0585004 A2 3/1994
EP 0989720 A1 3/2000
(Continued)

OTHER PUBLICATIONS

"Bellcore Notes on the Networks (Formerly BOC Notes on the LEC Networks)," Bellcore, Special Report SR-2275, Issue 3, Dec. 1997.
(Continued)

*Primary Examiner* — Hemant Patel
(74) *Attorney, Agent, or Firm* — Sterne, Kessler, Goldstein & Fox P.L.L.C.

(57) ABSTRACT

Disclosed is a secure telephone call management system for authenticating users of a telephone system in an institutional facility. Authentication of the users is accomplished by using a personal identification number, preferably in conjunction with speaker independent voice recognition and speaker dependent voice identification. When a user first enters the system, the user speaks his or her name which is used as a sample voice print. During each subsequent use of the system, the user is required to speak his or her name. Voice identification software is used to verify that the provided speech matches the sample voice print. The secure system includes accounting software to limit access based on funds in a user's account or other related limitations. Management software implements widespread or local changes to the system and can modify or set any number of user account parameters.

20 Claims, 38 Drawing Sheets

Related U.S. Application Data

No. 12/218,145, filed on Jul. 11, 2008, now Pat. No. 8,948,350, which is a continuation of application No. 10/893,575, filed on Jul. 16, 2004, now Pat. No. 7,403,766, which is a continuation-in-part of application No. 10/215,367, filed on Aug. 8, 2002, now Pat. No. 7,333,798.

(51) Int. Cl.

| | | |
|---|---|---|
| *H04M 1/67* | (2006.01) | |
| *A61K 31/435* | (2006.01) | |
| *A61K 31/44* | (2006.01) | |
| *A61K 31/505* | (2006.01) | |
| *H04M 3/22* | (2006.01) | |
| *G06F 17/30* | (2006.01) | |
| *G06K 9/00* | (2006.01) | |
| *G06K 9/62* | (2006.01) | |
| *H04N 5/33* | (2006.01) | |
| *H04M 3/42* | (2006.01) | |

(52) U.S. Cl.
CPC .. *G06F 17/30259* (2013.01); *G06F 17/30268* (2013.01); *G06F 17/30528* (2013.01); *G06F 17/30743* (2013.01); *G06F 17/30876* (2013.01); *G06K 9/00288* (2013.01); *G06K 9/6212* (2013.01); *H04M 1/67* (2013.01); *H04M 3/2281* (2013.01); *H04M 3/38* (2013.01); *H04M 3/385* (2013.01); *H04M 3/42221* (2013.01); *H04N 5/33* (2013.01); *H04M 2201/41* (2013.01); *H04M 2203/558* (2013.01); *H04M 2203/6054* (2013.01)

(58) Field of Classification Search
CPC ......... G06F 17/30528; G06F 17/30743; G06F 17/30876; G06K 9/00288; G06K 9/6212; H04M 1/67; H04M 3/2281; H04M 3/382; H04M 3/38; H04M 3/385; H04M 3/42221; H04M 2201/41; H04M 2203/558; H04M 2203/6054; H04N 5/33
USPC ............. 370/259–271, 351–357; 379/37–52, 379/67.1–88.28, 189, 201.01; 709/201–207, 217–248; 348/14.01–14.16; 704/270–278
See application file for complete search history.

(56) References Cited

U.S. PATENT DOCUMENTS

| | | | |
|---|---|---|---|
| 4,449,189 | A | 5/1984 | Feix et al. |
| 4,706,275 | A | 11/1987 | Kamil |
| 4,890,317 | A | 12/1989 | Hird et al. |
| 4,933,965 | A | 6/1990 | Hird |
| 4,935,956 | A | 6/1990 | Hellwarth et al. |
| 4,993,068 | A | 2/1991 | Piosenka et al. |
| 5,053,774 | A | 10/1991 | Schuermann et al. |
| 5,093,855 | A | 3/1992 | Vollert et al. |
| 5,170,426 | A | 12/1992 | D'Alessio et al. |
| 5,181,238 | A | 1/1993 | Medamana et al. |
| 5,185,781 | A | 2/1993 | Dowden et al. |
| 5,229,764 | A | 7/1993 | Matchett et al. |
| 5,274,695 | A | 12/1993 | Green |
| 5,276,444 | A | 1/1994 | McNair |
| 5,319,702 | A | 6/1994 | Kitchin et al. |
| 5,353,335 | A | 10/1994 | Durso et al. |
| 5,420,910 | A | 5/1995 | Rudokas et al. |
| 5,473,671 | A | 12/1995 | Partridge |
| 5,483,581 | A | 1/1996 | Hird et al. |
| 5,485,507 | A | 1/1996 | Brown et al. |
| 5,502,759 | A | 3/1996 | Cheng et al. |
| 5,511,111 | A | 4/1996 | Serbetcioglu et al. |
| 5,513,272 | A | 4/1996 | Bogosian, Jr. |
| 5,535,261 | A | 7/1996 | Brown et al. |
| 5,535,596 | A | 7/1996 | Todack |
| 5,539,812 | A | 7/1996 | Kitchin et al. |
| 5,561,718 | A * | 10/1996 | Trew .................. A61B 5/1176 382/118 |
| 5,623,539 | A | 4/1997 | Bassenyemukasa et al. |
| 5,629,981 | A | 5/1997 | Nerlikar |
| 5,638,430 | A | 6/1997 | Hogan et al. |
| 5,655,013 | A * | 8/1997 | Gainsboro .......... H04M 3/2281 379/188 |
| 5,675,704 | A | 10/1997 | Juang et al. |
| 5,696,880 | A | 12/1997 | Gustafson |
| 5,715,518 | A | 2/1998 | Barrere et al. |
| 5,717,743 | A | 2/1998 | McMahan et al. |
| 5,745,558 | A | 4/1998 | Richardson, Jr. et al. |
| 5,768,355 | A | 6/1998 | Salibrici et al. |
| 5,793,415 | A | 8/1998 | Gregory, III et al. |
| 5,796,811 | A | 8/1998 | McFarlen |
| 5,805,685 | A | 9/1998 | McFarlen |
| 5,809,126 | A | 9/1998 | Smith et al. |
| 5,809,462 | A | 9/1998 | Nussbaum |
| 5,822,418 | A | 10/1998 | Yacenda et al. |
| 5,867,562 | A | 2/1999 | Scherer |
| 5,875,236 | A | 2/1999 | Jankowitz et al. |
| 5,883,945 | A | 3/1999 | Richardson, Jr. et al. |
| 5,893,057 | A | 4/1999 | Fujimoto et al. |
| 5,923,746 | A | 7/1999 | Baker et al. |
| 5,926,533 | A | 7/1999 | Gainsboro |
| 5,937,043 | A | 8/1999 | He |
| 5,943,403 | A | 8/1999 | Richardson et al. |
| 5,950,167 | A | 9/1999 | Yaker |
| 5,953,652 | A | 9/1999 | Amin et al. |
| 5,956,634 | A | 9/1999 | Otterson et al. |
| 5,991,429 | A | 11/1999 | Coffin et al. |
| 6,052,454 | A | 4/2000 | Kek et al. |
| 6,054,928 | A | 4/2000 | Lemelson et al. |
| 6,058,163 | A | 5/2000 | Pattison et al. |
| 6,058,173 | A | 5/2000 | Penfield et al. |
| 6,064,963 | A | 5/2000 | Gainsboro |
| 6,078,807 | A | 6/2000 | Dunn et al. |
| 6,084,967 | A | 7/2000 | Kennedy et al. |
| 6,092,192 | A | 7/2000 | Kanevsky et al. |
| 6,104,922 | A | 8/2000 | Baumann |
| 6,122,239 | A | 9/2000 | Bodo et al. |
| 6,122,354 | A | 9/2000 | Dowens |
| 6,122,357 | A | 9/2000 | Farris et al. |
| 6,141,406 | A | 10/2000 | Johnson |
| 6,160,903 | A | 12/2000 | Hamid et al. |
| 6,161,090 | A | 12/2000 | Kanevsky et al. |
| 6,182,221 | B1 | 1/2001 | Hsu et al. |
| 6,185,536 | B1 | 2/2001 | Haber et al. |
| 6,213,391 | B1 | 4/2001 | Lewis |
| 6,219,439 | B1 | 4/2001 | Burger |
| 6,219,640 | B1 | 4/2001 | Basu et al. |
| 6,226,362 | B1 | 5/2001 | Gerszberg et al. |
| 6,246,751 | B1 | 6/2001 | Bergl et al. |
| 6,246,987 | B1 | 6/2001 | Fisher et al. |
| 6,252,947 | B1 | 6/2001 | Diamond et al. |
| 6,282,566 | B1 | 8/2001 | Lee et al. |
| 6,301,344 | B1 | 10/2001 | Meyer et al. |
| 6,327,345 | B1 | 12/2001 | Jordan |
| 6,345,252 | B1 | 2/2002 | Beigi et al. |
| 6,377,699 | B1 | 4/2002 | Musgrave et al. |
| 6,389,397 | B1 | 5/2002 | Otto |
| 6,421,645 | B1 | 7/2002 | Beigi et al. |
| 6,430,274 | B1 | 8/2002 | Winstead et al. |
| 6,442,265 | B1 | 8/2002 | Harlow et al. |
| 6,542,602 | B1 | 4/2003 | Elazar |
| 6,560,323 | B2 | 5/2003 | Gainsboro |
| 6,611,583 | B1 | 8/2003 | Gainsboro |
| 6,647,096 | B1 | 11/2003 | Milliorn et al. |
| 6,665,376 | B1 | 12/2003 | Brown |
| 6,665,380 | B1 | 12/2003 | Cree et al. |
| 6,665,736 | B1 | 12/2003 | Fan |
| 6,668,044 | B1 | 12/2003 | Schwartz et al. |
| 6,668,045 | B1 | 12/2003 | Mow |
| 6,681,205 | B1 | 1/2004 | San Martin et al. |
| 6,687,733 | B2 | 2/2004 | Manukyan |

(56) References Cited

U.S. PATENT DOCUMENTS

| | | |
|---|---|---|
| 6,731,744 B1 | 5/2004 | Khuc |
| 6,748,356 B1 | 6/2004 | Beigi et al. |
| 6,765,470 B2 | 7/2004 | Shinzaki |
| 6,766,295 B1 | 7/2004 | Murveit et al. |
| 6,775,269 B1 | 8/2004 | Kaczmarczyk et al. |
| 6,785,282 B1 | 8/2004 | Gardner |
| 6,788,772 B2 | 9/2004 | Barak et al. |
| 6,810,480 B1 | 10/2004 | Parker et al. |
| 6,819,219 B1 | 11/2004 | Bolle et al. |
| 6,836,556 B1 | 12/2004 | Bromba et al. |
| 6,853,716 B1 | 2/2005 | Shaffer |
| 6,892,052 B2 | 5/2005 | Kotola et al. |
| 6,920,209 B1 | 7/2005 | Gainsboro |
| 6,950,508 B1 | 9/2005 | Griffiths |
| 6,975,708 B1 | 12/2005 | Scherer |
| 6,978,238 B2 | 12/2005 | Wohlsen |
| 6,996,216 B2 | 2/2006 | Brown et al. |
| 7,035,386 B1 | 4/2006 | Susen et al. |
| 7,042,987 B2 | 5/2006 | Schwartz et al. |
| 7,042,992 B1 | 5/2006 | Falcone et al. |
| 7,054,430 B2 | 5/2006 | Lynam et al. |
| 7,079,636 B1 | 7/2006 | McNitt et al. |
| 7,092,494 B1 | 8/2006 | Anders et al. |
| 7,106,843 B1 * | 9/2006 | Gainsboro .......... H04M 3/2281 379/191 |
| 7,120,238 B1 | 10/2006 | Bednarz et al. |
| 7,167,551 B2 | 1/2007 | Brown et al. |
| 7,173,532 B2 | 2/2007 | Hanle |
| 7,181,017 B1 | 2/2007 | Nagel et al. |
| 7,191,133 B1 | 3/2007 | Pettay |
| 7,197,560 B2 | 3/2007 | Caslin et al. |
| 7,245,716 B2 | 7/2007 | Brown et al. |
| 7,278,028 B1 | 10/2007 | Hingoranee |
| 7,333,798 B2 | 2/2008 | Hodge |
| 7,348,961 B1 | 3/2008 | Shneidman |
| 7,403,766 B2 | 7/2008 | Hodge |
| 7,406,039 B2 | 7/2008 | Cherian et al. |
| 7,466,816 B2 | 12/2008 | Blair |
| 7,551,732 B2 | 1/2009 | Anders |
| 7,486,779 B2 | 2/2009 | Brown et al. |
| 7,494,061 B2 | 2/2009 | Reinhold |
| 7,505,406 B1 | 3/2009 | Spadaro et al. |
| 7,505,573 B2 | 3/2009 | Leonard |
| 7,529,357 B1 | 5/2009 | Rae et al. |
| 7,783,021 B2 | 8/2010 | Hodge |
| 7,805,457 B1 | 9/2010 | Viola et al. |
| 7,844,252 B2 | 11/2010 | Hodge |
| 7,848,510 B2 | 12/2010 | Shaffer et al. |
| 7,853,243 B2 | 12/2010 | Hodge |
| 7,860,222 B1 | 12/2010 | Sidler et al. |
| 7,881,446 B1 | 2/2011 | Apple |
| 7,889,847 B2 | 2/2011 | Gainsboro |
| 7,899,167 B1 | 3/2011 | Rae |
| 7,916,845 B2 | 3/2011 | Rae et al. |
| 7,979,612 B2 | 7/2011 | Kerdemelidis et al. |
| 8,000,269 B1 | 8/2011 | Rae et al. |
| 8,098,804 B1 | 1/2012 | Rae et al. |
| 8,135,115 B1 | 3/2012 | Hogg et al. |
| 8,295,446 B1 | 10/2012 | Apple |
| 8,370,262 B2 | 2/2013 | Blessing |
| 8,509,736 B2 | 8/2013 | Hodge |
| 8,515,031 B2 | 8/2013 | Hodge et al. |
| 8,577,003 B2 | 11/2013 | Rae |
| 8,705,701 B2 | 4/2014 | Bennett, III et al. |
| 8,886,663 B2 | 11/2014 | Gainsboro et al. |
| 8,929,525 B1 | 1/2015 | Edwards |
| 8,948,350 B2 | 2/2015 | Hodge |
| 9,014,355 B2 | 4/2015 | Heaton et al. |
| 9,143,609 B2 | 9/2015 | Hodge |
| 9,143,610 B2 | 9/2015 | Hodge |
| 9,282,188 B2 | 3/2016 | Hodge et al. |
| 9,357,061 B2 | 5/2016 | Rokosky et al. |
| 9,521,250 B2 | 12/2016 | Hodge |
| 9,686,402 B2 | 6/2017 | Hodge |
| 9,699,303 B2 | 7/2017 | Hodge |
| 2001/0034220 A1 | 10/2001 | Berstis |
| 2001/0036821 A1 | 11/2001 | Gainsboro et al. |
| 2001/0044295 A1 | 11/2001 | Saito et al. |
| 2001/0056349 A1 | 12/2001 | St John |
| 2002/0021001 A1 | 2/2002 | Stratford et al. |
| 2002/0021791 A1 | 2/2002 | Heilmann et al. |
| 2002/0025028 A1 | 2/2002 | Manto |
| 2002/0042879 A1 | 4/2002 | Gould et al. |
| 2002/0046055 A1 | 4/2002 | Martino et al. |
| 2002/0049817 A1 | 4/2002 | Drory et al. |
| 2002/0087858 A1 | 7/2002 | Oliver et al. |
| 2002/0140542 A1 * | 10/2002 | Prokoski ............ G06K 9/00885 340/5.52 |
| 2002/0152390 A1 * | 10/2002 | Furuyama .......... G06F 17/3025 713/185 |
| 2002/0159571 A1 * | 10/2002 | Stock .................. G06F 21/32 379/88.02 |
| 2002/0177433 A1 | 11/2002 | Bravo et al. |
| 2002/0188575 A1 | 12/2002 | Freeny |
| 2003/0046083 A1 | 3/2003 | Devinney, Jr. et al. |
| 2003/0086546 A1 | 5/2003 | Falcone et al. |
| 2003/0125944 A1 | 7/2003 | Wohlsen et al. |
| 2003/0126470 A1 | 7/2003 | Crites et al. |
| 2003/0138085 A1 | 7/2003 | Forman et al. |
| 2003/0215069 A1 | 11/2003 | Hitzeman |
| 2003/0229492 A1 | 12/2003 | Nolan |
| 2004/0010430 A1 | 1/2004 | Mani |
| 2004/0015355 A1 | 1/2004 | Trinkel |
| 2004/0022382 A1 | 2/2004 | Sweeney et al. |
| 2004/0028193 A1 | 2/2004 | Kim |
| 2004/0029564 A1 | 2/2004 | Hodge |
| 2004/0081296 A1 | 4/2004 | Brown et al. |
| 2004/0114739 A1 | 6/2004 | Hausmann et al. |
| 2004/0131160 A1 | 7/2004 | Mardirossian |
| 2004/0213388 A1 | 10/2004 | Mow |
| 2004/0249650 A1 | 12/2004 | Freedman et al. |
| 2004/0252447 A1 | 12/2004 | Hesse et al. |
| 2005/0063522 A1 | 3/2005 | Kim et al. |
| 2005/0094794 A1 | 5/2005 | Creamer et al. |
| 2005/0102371 A1 | 5/2005 | Aksu |
| 2005/0125226 A1 | 6/2005 | Magee |
| 2005/0175159 A1 | 8/2005 | Cooper et al. |
| 2005/0238154 A1 | 10/2005 | Heaton et al. |
| 2005/0246291 A1 | 11/2005 | Delgrosso et al. |
| 2005/0271251 A1 | 12/2005 | Russell et al. |
| 2005/0273333 A1 | 12/2005 | Morin |
| 2006/0198504 A1 | 9/2006 | Shemisa et al. |
| 2006/0285650 A1 | 12/2006 | Hodge |
| 2006/0285665 A1 | 12/2006 | Wasserblat et al. |
| 2007/0041545 A1 | 2/2007 | Gainsboro |
| 2007/0047734 A1 | 3/2007 | Frost |
| 2007/0071206 A1 | 3/2007 | Gainsboro et al. |
| 2008/0046241 A1 | 2/2008 | Osburn et al. |
| 2008/0195387 A1 | 8/2008 | Zigel et al. |
| 2009/0083841 A1 | 3/2009 | Gierach |
| 2010/0151820 A1 | 6/2010 | Mulherin et al. |
| 2011/0055256 A1 | 3/2011 | Phillips et al. |
| 2011/0206038 A1 | 8/2011 | Hodge |
| 2013/0308499 A1 | 11/2013 | Hodge |
| 2013/0329867 A1 | 12/2013 | Hodge |
| 2015/0156315 A1 | 6/2015 | Hodge |
| 2015/0288810 A1 | 10/2015 | Hodge |
| 2015/0358457 A1 | 12/2015 | Hodge |
| 2016/0014270 A1 | 1/2016 | Hodge |
| 2016/0021243 A1 | 1/2016 | Hodge |
| 2016/0255189 A1 | 9/2016 | Hodge |
| 2017/0013120 A1 | 1/2017 | Hodge |
| 2017/0104869 A1 | 4/2017 | Hodge |

FOREIGN PATENT DOCUMENTS

| | | |
|---|---|---|
| EP | 1191771 A2 | 3/2002 |
| EP | 1280137 B1 | 12/2004 |
| GB | 2 148 569 A | 5/1985 |

(56) References Cited

FOREIGN PATENT DOCUMENTS

| WO | WO 97/46964 | 12/1997 |
|---|---|---|
| WO | WO 0074355 A1 | 12/2000 |

OTHER PUBLICATIONS

"Bellcore Notes on the Networks," Bellcore, Special Report SR-2275, Issue 3, Dec. 1997.
"Cisco IAD2400 Series Business-Class Integrated Access Device", Cisco Systems Datasheet, 2003.
"Cisco IAD2420 Series Integrated Access Devices Software Configuration Guide—Initial Configuration," Cisco Systems, accessed Sep. 23, 2014, accessible at http://www.cisco.com/en/US/docs/routers/access/2400/2420/software/configuration/guide/init_cf.html.
"Hong Kong: Prison Conditions in 1997," Human Rights Watch, Mar. 1, 1997, C905, available at http://www.refworld.org/docid/3ae6a7d014.html, accessed May 29, 2014.
"PacketCable™ Audio/Video Codecs Specification," Cable Television Laboratories, Inc., Ser. No. PKT-SP-CODEC-I05-040113 (2004).
"Service-Observing Arrangements Using Key Equipment for Telephone Company Business Offices. Description and Use," Pac. Tel. & Tel. Co., Bell System Practices, Station Operations Manual, Section C71.090, Issue A, 1-1-57-N (1957).
"SIP and IPLinkTM in the Next Generation Network: An Overview," Intel, 2001.
"The AutoEDMS Document Management and Workflow System: An Overview of Key Features, Functions and Capabilities." ACS Software, May 2003.
"Voice Over Packet in Next Generation Networks: An Architectural Framework," Bellcore, Special Report SR-4717, Issue 1, Jan. 1999.
Beek et al., "An Assessment of the Technology of Automatic Speech Recognition for Military Applications," IEEE Trans. Acoustics, Speech, and Signal Processing, vol. ASSP-25, No. 4, pp. 310-322 (1977).
Bimbaum et al., "A Voice Password Ssytem for Access Security," AT&T Technical Journal, vol. 65, No. 5, Sep./Oct. 1986; pp. 68-74.
BubbleLINK® Software Architecture (Science Dyanmics 2003).
Bur Goode, Voice Over Internet Protocol (VoIP), Proceedings of the IEEE, vol. 90, No. 9, 1495-1517 (Sep. 2002).
Claim Construction Order, *Single Touch Interactive, Inc.* v. *Zoove Corporation*, Case No. 4:12-cv-00831-YGR (N.D. Cal.), filed Jul. 17, 2013.
Clifford J. Weinstein, MIT, The Experimental Integrated Switch Network—A System-Level Network Test Facility (IEEE 1983).
Commander Call Control System, Rev. 1.04 (Science Dynamics 2002).
Complaint for Patent Infringement, filed Aug. 1, 2013, *Securus Technologies, Inc.* v. *Global Tel\*Link Corporation*, Case No. 3:13-cv-03009-K (N.D. Tex.).
Definition of "logic", IEEE 100: The Authoritative Dictionary of IEEE Standard Terms, Seventh Edition, Standards Information Network, IEEE Press (2000).
Definition of "telephony", McGraw-Hill Dictionary of Scientific and Technical Terms, 6th Edition (McGraw-Hill, 2003).
Definitions of "Local Area Network (LAN)" and "Wide Area Network (WAN)," Microsoft Computer Dictionary (Microsoft Press 2002), pp. 304 and 561.
English-language Abstract for European Patent Publication No. 0989720 A1.
English-language Abstract for European Patent Publication No. 1191771 A2.
Excerpts from the Prosecution History of U.S. Appl. No. 10/135,878, filed Apr. 29, 2002.
Excerpts from the Prosecution History of U.S. Pat. No. 7,899,167, U.S. Appl. No. 10/642,532, filed Aug. 15, 2003.
File History of U.S. Pat. No. 7,403,766, U.S. Appl. No. 10/893,575, filed Jul. 16, 2004.
File History of U.S. Pat. No. 7,899,167, U.S. Appl. No. 10/642,532, filed Aug. 15, 2003.
File History of U.S. Pat. No. 8,577,003, U.S. Appl. No. 13/009,483, filed Jan. 19, 2011.
File History of U.S. Pat. No. 9,143,609, U.S. Appl. No. 13/949,980, flied Jul. 24, 2013.
Final Office Action for U.S. Appl. No. 12/861,322, dated Apr. 24, 2013; 4 pages.
Final Office Action for U.S. Appl. No. 13/949,980, dated Nov. 20, 2014; 7 pages.
Final Office Action for U.S. Appl. No. 14/743,041, dated Jul. 19, 2016; 6 pages.
Fleischman, E., "Advanced Streaming Format (ASF) Specification," Microsoft Corporation (Jan. 9, 1998).
Fox, B., "The First Amendment Rights of Prisoners," 63 J. Crim. L. Criminology & Police Sci. 162 (1972).
Investigative Analysis Software webpage titled "i2 TextChart, Text Visualized", published by The Visual Space, available at www.i2.co.uk/proclucts/i2TextChart/, accessed Jun. 13,2005; 2 pages.
Jeff Hewett and Lee Dryburgh, Signaling System No. 7 (SS7/C7): Protocol, Architecture, and Services (Networking Technology) at 85 (Cisco Press, Jun. 2005).
Joint Claim Construction and Prehearing Statement, Exhibit B: Securus' Intrinsic and Extrinsic Evidence Charts, *Global Tel\*Link Corporation* v. *Securus Technologies, Inc.*, No. 3:14-cv-00829-K (N.D. Tex.), Sep. 26, 2014.
Kozamernik, F., "Media Streaming over the Internet—an overview of delivery technologies," EBU Technical Review (Oct. 2002).
Maes, et al., "Conversational speech biometrics," E-Commerce Agents, Marketplace Solutions, Security Issues, and Supply and Demand, Springer-Verlang, London, UK, 2001, pp. 166-179.
Microsoft Computer Dictionary, Fifth Edition, Microsoft Computer Press: Redmond, WA. 2002.
Newton, H., Newton's Telecom Dictionary (18th ed. 2002); p. 655.
Non-Final Office Action for U.S. Appl. No. 14/831,533, dated Nov. 17, 2015; 8 pages.
Non-Final Office Action for U.S. Appl. No. 11/045,589, dated Jul. 10, 2008; 5 pages.
Non-Final Office Action for U.S. Appl. No. 11/045,589, dated Jun. 2, 2009; 4 pages.
Non-Final Office Action for U.S. Appl. No. 12/861,322, dated Jul. 3, 2012; 6 pages.
Non-Final Office Action for U.S. Appl. No. 13/949,980, dated Jul. 15, 2014; 6 pages.
Non-Final Office Action for U.S. Appl. No. 14/613,153, dated May 31, 2016; 18 pages.
Notice of Allowance for U.S. Appl. No. 11/045,589, dated Apr. 13, 2010; 4 pages.
Notice of Allowance for U.S. Appl. No. 13/949,980, dated Aug. 4, 2015; 5 pages.
Notice of Allowance for U.S. Appl. No. 13/949,980, dated May 7, 2015; 5 pages.
Notice of Allowance for U.S. Appl. No. 14/831,533, dated Jun. 2, 2016; 5 pages.
Nuance 7.0 Technical Data Sheet, available at www.nuance.com; 2 pages.
Nuance 7.0: Powerful Speech Recognition for Transactions over the Telephone, Nuance Communications, 2000; 2 pages.
Nuance 7.0: Powerful Speech Recognition for Transactions over the Telephone, Nuance Communications, Jun. 19, 2000-Mar. 14, 2002, http://www.nuance.com/index.htma?SCREEN=nuance7; 2 pages.
Osifchin, N., "A Telecommunications Buildings/Power Infrastructure in a New Era of Public Networking," IEEE 2000.
PacketCableTM 1.0 Architecture Framework Technical Report, PKT-TR-ARCH-V0 1-001201 (Cable Television Laboratories, Inc. 1999).
Pages from http://www.corp.att.com/history, archived by web.archive.org on Nov. 4, 2013.
Parties' Proposed Claim Constructions in *Global Tel\*Link Corporation* v. *Securus Technologies, Inc.*, No. 3:14-cv-00829-K (N.D. Tex.), filed Sep. 26, 2014; 17 pages.
Prosecution History of U.S. Appl. No. 11/005,816, filed Dec. 7, 2004.

(56) References Cited

OTHER PUBLICATIONS

Prosecution History of U.S. Appl. No. 11/045,589, filed Jan. 28, 2005.
Prosecution History of U.S. Appl. No. 11/182,625, filed Jul. 15, 2005.
Prosecution History of U.S. Appl. No. 11/479,990, filed Jun. 30, 2006.
Response to Office Action, filed Jan. 6, 2009, in Prosecution History of U.S. Appl. No. 10/642,532, filed Aug. 15, 2003.
Rey, R.F., ed., "Engineering and Operations in the Bell System," 2nd Edition, AT&T Bell Laboratories: Murray Hill, NJ, 1983.
Science Dynamics, Inmate Telephone Control Systems, http://scidyn.com/fraudprev_main.htm (archived by web.archive.org on Jan. 12, 2001).
Science Dynamics, SciDyn BubbleLINK, http://www.scidyn.com/products/bubble.html (archived by web.archive.org on Jun. 18, 2006).
Science Dynamics, SciDyn Call Control Solutions: Commander II, http://www.scidyn.com/products/commander2.html (archived by web.archive.org on Jun. 18, 2006).
Science Dynamics, SciDyn IP Gateways, http://scidyn.com/products/ipgateways.html (archived by web.archive.org on Aug. 15, 2001).
Science Dynamics, Science Dynamics—IP Telephony, http://www.scidyn.com/iptelephony_maim.htm (archive by web.archive.org on Oct. 12, 2000).
Simmons, R., "Why 2007 is Not Like 1984: A Broader Perspective on Technology's Effect on Privacy and Fourth Amendment Jurisprudence," 97 J. Crim. L. & Criminology 531(2006-2007).
Smith, Megan J., "Corrections Turns Over a New LEAF: Correctional Agencies Receive Assistance From the Law Enforcement Analysis Facility," Corrections Today, Oct. 1, 2001.
Specification of U.S. Appl. No. 10/720,848, "Information Management and Movement System and Method," to Viola, et al., filed Nov. 24, 2003.
Sundstrom, K., "Voice over IP: An Engineering Analysis," Master's Thesis, Department of Electrical and Computer Engineering, University of Manitoba, Sep. 1999.
U.S. Appl. No. 14/831,533, to Hodge, "Digital Telecommunications Call Management and Monitoring System," filed Aug. 20, 2015.
U.S. Appl. No. 15/154,645, "Telecommunication Call Managment and Monitoring System With Voiceprint Verification," to Hodge, filed May 13, 2016.
USPTO Class Definition, Telephonic Communications.
Walden, R., "Performance Trends for Analog-to-Digital Converters," IEEE Communications Magazine, Feb. 1999.
File History of U.S. Pat. No. 7,333,798, U.S. Appl. No. 10/215,367, filed Aug. 8, 2002.
CTI EDGE Automated Operator System Brochures, Jan.-Feb. 1988.
Value Added Communications, System 20 Dealer Information Package, Apr. 1991.
Notice of Allowance for U.S. Appl. No. 10/215,367, dated Sep. 18, 2007; 3 pages.
Notice of Allowability for U.S. Appl. No. 10/215,367, dated Sep. 18, 2007; 3 pages.
Non-Final Office Action for U.S. Appl. No. 10/215,367, dated May 23, 2006, 7 pages.
Non-Final Office Action for U.S. Appl. No. 10/215,367, dated Dec. 16, 2004; 8 pages.
Final Office Action for U.S. Appl. No. 10/215,367, dated Feb. 20, 2007; 8 pages.
Final Office Action for U.S. Appl. No. 10/215,367, dated Sep. 7, 2005; 10 pages.
Notice of Allowance for U.S. Appl. No. 10/893,575, dated Mar. 11, 2008; 7 pages.
Non-Final Office Action for U.S. Appl. No. 10/893,575, dated Jul. 21, 2006; 15 pages.
Final Office Action for U.S. Appl. No. 10/893,575, dated Feb. 22, 2007; 13 pages.

Notice of Allowability for U.S. Appl. No. 11/371,641, dated Sep. 21, 2010; 3 pages.
Notice of Allowance for U.S. Appl. No. 11/371,641, dated Jul. 21, 2010; 6 pages.
Non-Final Office Action for U.S. Appl. No. 11/371,641, dated Mar. 5, 2010; 13 pages.
Non-Final Office Action for U.S. Appl. No. 11/371,641, dated May 13, 2009; 9 pages.
Final Office Action for U.S. Appl. No. 11/371,641 dated Oct. 8, 2009; 10 pages.
Notice of Allowance for U.S. Appl. No. 12/002,507, dated Aug. 5, 2010; 6 pages.
Non-Final Office Action for U.S. Appl. No. 12/002,507, dated Sep. 24, 2009; 8 pages.
Final Office Action for U.S. Appl. No. 12/002,507, dated Mar. 9, 2010; 10 pages.
Sunplemental Notice of Allowability for U.S. Appl. No. 12/218,145, dated Dec. 22, 2014; 2 pages.
Notice of Allowance for U.S. Appl. No. 12/218,145, dated Sep. 11, 2014; 10 pages.
Non-Final Office Action for U.S. Appl. No. 12/218,145, dated Jun. 19, 2013; 26 pages.
Non-Final Office Action for U.S. Appl. No. 12/218,145, dated Nov. 23, 2011; 19 pages.
Final Office Action for U.S. Appl. No. 12/218,145, dated Apr. 4, 2014; 21 pages.
Final Office Action for U.S. Appl. No. 12/218,145, dated Dec. 19, 2012; 24 pages.
Supplemental Notice of Allowability for U.S. Appl. No. 12/951,790, dated May 3, 2013; 8 pages.
Supplemental Notice of Allowability for U.S. Appl. No. 12/951,790, dated Jul. 22, 2013; 8 pages.
Notice of Allowance, for U.S. Appl. No. 12/951,790, dated Apr. 16, 2013; 12 pages.
Non-Final Office Action for U.S. Appl. No. 12/951,790, dated Nov. 6. 2012; 4 pages.
Final Office Action for U.S. Appl. No. 13/966,011, dated Feb. 13, 2015; 5 pages.
Non-Final Office Action for U.S. Appl. No. 13/996,011, dated Oct. 23, 2014; 8 pages.
Notice of Allowance for U.S. Appl. No. 13/966,011, dated Mar. 20, 2015; 7 pages.
Notice of Allowability for U.S. Appl. No. 13/966,011, dated May 20, 2015; 4 pages.
Notice of Allowance for U.S. Appl. No. 13/966,011, dated Jul. 30, 2015; 7 pages.
"Open Architecture—Windows NT," Audiolog Intelligent Recording Solutions, Mercom Systems, Inc., 1998.
"The Pay-Tel Phone," PayTel Communications Equipment and Products, Dec. 14, 2003.
"Criminal Calls: A Review of the Bureau of Prisons' Management of Inmate Telephone Privileges" U.S. Department of Justice, Office of the Inspector General, Aug. 1999.
U.S. Appl. No. 10/135,878, "Information Management and Movement System and Method," to Viola, et al., filed Apr. 29, 2002.
U.S. Appl. No. 60/607,447, "IP-based telephony system and method," to Apple, et al., filed Sep. 3, 2004.
Prosecution History of U.S. Appl. No. 12/002,507, filed Dec. 17, 2007.
Defendant's Opening Claim Construction Brief, *Global Tel\*Link Corporation* v. *Securus Technologies, Inc.*, Case No. 3:14-cv-0829-K (N.D. Tex.), filed Nov. 19, 2014.
Defendant's Responsive Claim *Global Tel\*Link Corporation* v. *Securus Technologies, Inc.*, Case No. 3:14-cv-0829-K (N.D. Tex.), filed Dec. 10, 2014.
"Global Call API for Linux and Windows Operating Systems," Intel Dialogic Library Reference, Dec. 2005. (3 parts).
Auckenthaler, et al., "Speaker-Centric Score Normalization and Time Pattern Analysis for Continuous Speaker Verification," International Conference on Acoustic, Speech, and Signal Processing (ICASSP), vol. 2, Jun. 2000, pp. 1065-1068.

(56) References Cited

OTHER PUBLICATIONS

Beigi, H., "Challenges of Large-Scale Speaker Recognition," 3rd European Cooperation in the Field of Scientific and Technical Research Conference, Nov. 4, 2005.
Carey, et al., "User Validation for Mobile Telephones," International Conference, on Acoustics, Speech, and Signal Processing (ICASSP), vol. 2, Jun. 2000, pp. 1093-1096.
Furui, S., "50 Years of Progress in Speech and Speaker Recognition Research," ECTI Transactions on Computer and Information Technology, vol. 1, No. 2, Nov. 2005, pp. 64-74.
Pollack, et al., "On the Identification of Speakers by Voice," The Journal of the Acoustical Society of America, vol. 26, No. 3, May 1954.
Shearme, et al., "An Experiment Concerning the Recognition of Voices," Language and Speech, vol. 2, No. 3, Jul./Sep. 1959.
Juang et al., "Automatic Speech Recognition—A Brief History of the Technology Development," Oct. 8, 2014.
Kinnunen. et al., "Real-Time Speaker Identification and Verification," IEEE Transactions on Audio, Speech, and Language Processing, vol. 14, No. 1, Jan. 2006, pp. 277-288.
Original Specification as-filed Aug. 26, 2005, in U.S. Appl. No. 11/212,495 to Frost.
Specification as-filed Jul. 22, 2005, in U.S. Appl. No. 11/187,423 to Shaffer.
Ross, et al., "Multimodal Biometrics: An Overview," Proc. of 12th European Signal Processing Conference (EUSIPCO), Vienna, Austria, Sep. 2004, pp. 1221-1224.
Prosecution History of U.S. Appl. No. 11/480,258, filed Jun. 30, 2006.
"Cool Edit Pro, Version 1.2 User Guide," Syntrillium Software Corporation, 1998.
Bolton, et al., "Statistical Fraud Detection: A Review," Statistical Science, vol. 17, No. 3 (2002), pp. 235-255.
Rosenberg, et al., "The Use of Cohort Normalized Scores for Speaker Verification," Speech Research Department, AT&T Bell Laboratories, 2nd International Conference on Spoken Language Processing, Banff, Alberta, Canada, Oct. 12-16, 1992.
Audacity Team, "About Audacity," World Wide Web, 2014, accessible at http://wiki.audacity.team.org/wiki/About_Audacity.
Beigi, et al., "A Hierarchical Approach to Large-Scale Speaker Recognition," EuroSpeech 1999, Sep. 1999, vol. 5; pp. 2203-2206.
Beigi, et al., "IBM Model-based and Frame-By-Frame Speaker-Recognition," Speaker Recognition and its Commercial and Forensic Applications, Apr. 1998; pp. 1-4.
Boersma, et al., "Praat: Doing Phonetics by computer," World Wide Web, 2015, accessible at http://www.fon.hum.uva.nl/praat.
Chaudhari, et al., "Transformation enhanced multi-grained modeling for text-independent speaker recognition," International Conference on Spoken Language Processing, 2000, pp. 298-301.
Clavel, et al., "Events Detection for an Audio-Based Surveillance System," IEEE International Conference on Multimedia and Expo (ICME2005), Jul. 6-8, 2005, pp. 1306-1309.
Dunn, et al., "Approaches to speaker detection and tracking in conversational speech," Digital Signal Processing, vol. 10, 2000; pp. 92-112.
File History of U.S. Pat. No. 8,886,663, U.S. Appl. No. 12/284,450, filed Sep. 20, 2008. (2 parts).
Furui, et al., "Experimental studies in a new automatic speaker verification system using, telephone speech," Acoustics, Speech, and Signal Processing, IEEE International Conference on ICASSP '80, vol. 5, Apr. 1980, pp. 1060-1062.
Hansen, et al., "Speaker recognition using phoneme-specific gmms," The Speaker and Language Recognition Workshop, May-Jun. 2004.
Isobe, et al., "A new cohort normalization using local acoustic information for speaker verification," Proceedings of the IEEE International Acoustics, Speech, and Signal Processing, vol. 2, Mar. 1999; pp. 841-844.
Maes, et al., "Open SESAME! Speech, Password or Key to Secure Your Door?," Asian Conference on Computer Vision, Jan. 1998; pp. 1-3.
Matsui, et al., "Concatenated Phoneme Models for Text-Variable Speaker Recognition," International Conference on Acoustics, Speech, and Signal Processing (ICASSP), vol. 2, Apr. 1993; pp. 391-394.
"The NIST Year 2002 Speaker Recognition Evaluation Plan," NIST, Feb. 27, 2002, accessible at http://www.itl.nist.gov/iad/mig/tests/spk/2002/2002-spkrecevalplan-v60.pdf.
Pelecanos, J. "Conversational biometrics," in Biometric Consortium Meeting, Baltimore, MD, Sep. 2006, accessible at http://www.biometrics.org/bc2006/presentations/Thu_Sep_21/Session_I/Pelecanos_Conversational_Biometics.pdf.
Reynolds, D., "Automatic Speaker Recognition Using Gaussian Mixture Speaker Models," The Lincoln Laboratory Journal, vol. 8, No. 2, 1995; pp. 173-192.
Viswanathan, et al., "Multimedia Document Retrieval using Speech and Speaker Recognition," International Journal on Document Analysis and Recognition, Jun. 2000, vol. 2; pp. 1-24.
English-Language Abstract of European Patent Application Publication No. 0989720 AI; 2 pages.
English-Language Abstract of European Patent Application Publication No. 1191771 A2; 2 pages.
Non-Final Office Action for U.S. Appl. No. 14/613,153, dated Oct. 2, 2015; 17 pages.
Non-Final Office Action for U.S. Appl. No. 14/613,153, dated Nov. 18, 2015; 20 pages.
Definitions of "suspicion" and "suspect", American Heritage Dictionary, 4th Edition, New York: Houghton Mifflin, 2006; pp. 1743-1744.
Non-Final Office Action for U.S. Appl. No. 14/743,041, dated Feb. 17, 2016; 6 pages.
U.S. Appl. No. 12/284,450, "Multi-Party Conversation Analyzer and Logger," to Gainsboro et al., filed Sep. 20, 2008; 47 pages.
Definition of "constantly", The American Heritage College Dictionary, 4th Ed. (2002); p. 306.
Non-Final Office Action for U.S. Appl. No. 14/865,779, dated Aug. 4, 2016; 6 pages.
Non-Final Office Action for U.S. Appl. No. 14/865,679, dated Aug. 1, 2016; 8 pages.
Non-Final Office Action for U.S. Appl. No. 14/831,533, dated Sep. 7, 2016; 8 pages.
Notice of Allowance for U.S. Appl. No. 14/743,041, dated Oct. 12, 2016; 7 pages.
Notice of Allowance for U.S. Appl. No. 14/865,779, dated Dec. 15, 2016; 7 pages.
Non-Final Office Action for U.S. Appl. No. 15/266,551, dated Dec. 16, 2016; 8 pages.
Non-Final Office Action for U.S. Appl. No. 15/268,142, dated Jan. 13, 2017; 21 pages.
Non-Final Office Action for U.S. Appl. No. 15/337,804, dated Jan. 3, 2017; 27 pages.
Non-Final Office Action for U.S. Appl. No. 15/287,458, dated Dec. 29, 2016; 20 pages.
Final Office Action for U.S. Appl. No. 14/831,533, dated Jul. 10, 2017; 9 pages.
Final Office Action for U.S. Appl. No. 15/337,804, dated Jul. 12, 2017; 36 pages.
Final Office Action for U.S. Appl. No. 15/266,551, dated Aug. 9, 2017; 8 pages.
Non-Final Office Action for U.S. Appl. No. 14/613,153, dated Jun. 28, 2017; 30 pages.
Final Office Action for U.S. Appl. No. 15/287,458, dated Apr. 5, 2017; 19 pages.
Non Final Office Action for U.S. Appl. No. 14/831,533, dated May 3, 2017; 7 pages.
*Global Tel\*Link Corporation v. Securus Technologies, Inc.*, Case No. 3:14-cv-00829-K (N.D. Tex.), Stayed dure to pending Inter Partes Reviews Aug. 17, 2015.
*Securus Technologies, Inc., v. Global Tel\*Link Corporation*, Case No. IPR2015-00155 (P.T.A.B.), Final Written Decision Issued Apr. 7, 2016.

(56) References Cited

OTHER PUBLICATIONS

*Securus Technologies, Inc.*, v. *Global Tel*Link Corporation*, Case No. IPR2015-00155 (P.T.A.B.), Terminated Jan. 10, 2017.
Final Office Action for U.S. Appl. No. 14/613,153, dated Jan. 25, 2017; 35 pages.
Non-Final Office Action for U.S. Appl. No. 15/154,645, dated Feb. 1, 2017; 5 pages.
Non-Final Office Action for U.S. Appl. No. 15/346,543, dated Feb. 23, 2017; 24 pages.
Notice of Allowance for U.S. Appl. No. 14/865,779, dated Feb. 15, 2017; 4 pages.

\* cited by examiner

FIG. 12

Telephone Location Maintenance

Telephone Location

| Station | Living Unit | Location | | Rec Ch. | Time(s) |
|---|---|---|---|---|---|
| 0001 | Default | LINE #1 | | 0001 | 1 |
| 0002 | Default | LINE #2 | | 0002 | 2 |
| 0003 | LOCATION A | LINE #3 | | 0003 | 3 |
| 0004 | LOCATION A | LINE #4 | | 0004 | 4 |
| 0005 | LOCATION A | LINE #5 | | 0005 | 5 |
| 0006 | Default | LINE #6 | | 0006 | 6 |
| 0007 | Default | LINE #7 | | 0007 | 7 |
| 0008 | Default | LINE #8 | | 0008 | 8 |
| 0009 | CELL BLOCK B | LINE #9 | | 0009 | 9 |
| 0010 | CELL BLOCK B | LINE #10 | | 0010 | 10 |
| 0011 | CELL BLOCK B | LINE #11 | | 0011 | 11 |
| 0012 | Default | LINE #12 | | 0012 | 12 |

Site Server Name: itacni_test — 1201

Station Number: 0004    Rec Channel: 4

Living Unit: LOCATION A — 1205

Location: LINE #4 — 1207

[Change]  [Close]

Nationwide Telephone Number Control — 1400

Facility Telephone Number — 1402

| Telephone Number | Type |
|---|---|
| (212) 383-0404 | Approved |
| (800) 426-9400 | Approved |
| (972) 808-3305 | Approved |
| (567) 887-2324 | Blocked |
| (972) 454-0100 | Blocked |
| (212) 424-1000 | Blocked |
| (914) XXX-XXXX | Blocked |
| (202) 222-XXXX | Blocked |
| (214) 555-1212 | Blocked |
| (972) 808-9431 | Allowed |

Telephone Number: ( 914 ) XXX - XXXX — 1403

Max Extra Digits: 0 — 1405

Type — 1404
● Block  ○ Approved  ○ Exclude
☑ Collect  ☑ Direct

Number of days: 0    Date: 11/17/1998 — 1409

Comments: NO WESTCHESTER CALLS ALLOWED — 1411

User: Administrator

Add   Change   Delete — 1407    International — 1413   OK   Close

| Date | Time | Type | Amount | Balance | Facility | Ref. Number | User |
|------|------|------|--------|---------|----------|-------------|------|
| 10/01/1998 | 09:08 | INMATE INIT FUND | $100.00 | $7374.55 | 2 | 1189 | INMA |
| 10/03/1998 | 00:54 | DEPOSIT | $300.00 | $7574.55 | 2 | 1207 | Admin |
| 10/03/1998 | 01:27 | WITHDRAW | $300.00 | $7274.55 | 2 | 1208 | Admin |
| 10/03/1998 | 03:26 | DEPOSIT | $123.00 | $7397.55 | 2 | 1209 | Admin |
| 10/03/1998 | 03:27 | REFUND | $23.00 | $7420.55 | 2 | 1210 | Admin |
| 10/03/1998 | 03:28 | WITHDRAW | $100.00 | $7320.55 | 2 | 1211 | Admin |
| 10/03/1998 | 03:38 | DEPOSIT | $234.00 | $7554.55 | 2 | 1212 | Admin |
| 10/03/1998 | 03:35 | WITHDRAW | $123.00 | $7431.55 | 2 | 1213 | Admin |
| 10/03/1998 | 03:44 | DEPOSIT | $123.00 | $7554.55 | 2 | 1214 | Admin |
| 10/03/1998 | 03:44 | WITHDRAW | $123.00 | $7431.55 | 2 | 1215 | Admin |
| 10/03/1998 | 03:47 | DEPOSIT | $234.00 | $7665.55 | 2 | 1216 | Admin |
| 10/03/1998 | 03:48 | WITHDRAW | $234.00 | $7431.55 | 2 | 1217 | Admin |
| 10/03/1998 | 03:50 | DEPOSIT | $23.00 | $7454.55 | 2 | 1218 | Admin |

Year 1998  Month Oct  Display  Current Month  Sort Order  Refund

FIG. 26

| Date | Time | Dialed Digits | Duration | Charge | Charge Type | Call Result | Recorder | Alert Type |
|---|---|---|---|---|---|---|---|---|
| 10/19/1998 | 00:00 | 9721618625 | 0 | $0.00 | DIRECT CALL | 10 | 62 | N/A |
| 10/19/1998 | 00:00 | 9721618625 | 0 | $0.00 | DIRECT CALL | 10 | 62 | N/A |
| 10/19/1998 | 00:00 | 9721618625 | 0 | $0.00 | DIRECT CALL | 10 | 62 | N/A |
| 10/19/1998 | 00:00 | 9721618625 | 87 | $0.30 | DIRECT CALL | 0 | 62 | N/A |
| 10/19/1998 | 00:00 | 9721618625 | 87 | $0.30 | DIRECT CALL | 0 | 62 | N/A |
| 10/19/1998 | 00:00 | 9721618625 | 0 | $0.00 | DIRECT CALL | 10 | 62 | N/A |
| 10/19/1998 | 00:00 | 9721618625 | 87 | $0.30 | DIRECT CALL | 0 | 62 | N/A |
| 10/19/1998 | 00:00 | 9721618625 | 85 | $0.30 | DIRECT CALL | 0 | 62 | N/A |
| 10/19/1998 | 00:00 | 9721618625 | 87 | $0.30 | DIRECT CALL | 10 | 62 | N/A |
| 10/19/1998 | 00:00 | 9721618625 | 0 | $0.00 | DIRECT CALL | 0 | 62 | N/A |
| 10/19/1998 | 00:00 | 9721618625 | 87 | $0.30 | DIRECT CALL | 0 | 62 | N/A |
| 10/19/1998 | 00:00 | 9721618625 | 87 | $0.30 | DIRECT CALL | 0 | 62 | N/A |

FIG. 30

Call Details

- Telephone: 2026162060
- Date/Time: 08/14/2000 14:01:51
- Call Result: Completed call
- Extra Dialed Digits: ☐
- Three Way Call: ☐
- Facility: Y2K DEMO 1
- Telephone Location: CAMP 1-E
- Station ID: 0001
- Destination: BOP
- Call Type: Long Distance
- Carrier: GTE
- City: WASHINGTON
- State: DC

[Play] [Close]

FIG. 33

| AID | Date | Time | Dest_ANI | Dur | Station Name |
|---|---|---|---|---|---|
| 09090111 | 11/10/2000 | 08:51:49 | 9728082781 | 0:19 | CAMP 1-E |
| 09090111 | 11/10/2000 | 09:12:22 | 9728083382 | 2:17 | CAMP 1-E |
| 09090111 | 11/10/2000 | 09:18:29 | 9728083382 | 0:00 | CAMP 1-E |
| 09090111 | 11/13/2000 | 08:39:02 | 9728083382 | 0:17 | CAMP 1-E |
| 09090111 | 11/13/2000 | 08:42:49 | 9728083382 | 0:00 | CAMP 1-E |
| 09090222 | 11/10/2000 | 08:57:35 | 9728083313 | 1:41 | CAMP 1-E |
| 09090222 | 11/13/2000 | 08:54:50 | 9728083382 | 0:00 | CAMP 1-E |
| 09090222 | 11/13/2000 | 09:06:59 | 9728083382 | 1:59 | CAMP 1-E |
| 09090333 | 11/10/2000 | 09:10:16 | 9728083382 | 0:35 | CAMP 1-E |
| 09090333 | 11/10/2000 | 09:20:47 | 9728083382 | 0:00 | CAMP 1-E |
| 09090333 | 11/10/2000 | 09:22:47 | 9728083382 | 0:13 | CAMP 1-E |
| 09990101 | 12/19/2000 | 13:47:18 | 9728083382 | 0:05 | CAMP 1-E |
| 09990101 | 12/19/2000 | 14:34:05 | 4073337000 | 0:00 | CAMP 1-E |
| 09990101 | 12/19/2000 | 14:38:21 | 4073337000 | 0:05 | CAMP 1-E |
| 09990101 | 12/18/2000 | 15:43:04 | 4073337000 | 0:00 | CAMP 1-E |
| 09990102 | 12/20/2000 | 12:47:58 | 2143400650 | 0:21 | CAMP 1-E |
| 09990102 | 01/20/2001 | 13:16:13 | 0115722412438 | 0:00 | CAMP 1-E |
| 09990109 | 12/19/2000 | 15:28:50 | 9728083307 | 0:00 | CAMP 1-E |
| 09990110 | 12/19/2000 | 15:47:04 | 9728083307 | 0:00 | CAMP 1-E |
| 11234453 | 11/09/2000 | 15:38:34 | 9728083307 | 0:00 | CAMP 1-E |
| 11234453 | 11/09/2000 | 15:44:19 | 9728083307 | 0:00 | CAMP 1-E |
| 11234453 | 11/10/2000 | 11:58:12 | 9728083307 | 0:00 | CAMP 1-E |

[Close] [Save To] [Print] [Printer Setup] [Play] [Cancel Play]

FIG. 35

Run Date: 04/12/2000
Run Time: 17:57:47

Correctional Facility
Account Telephone Number List

Page 1 of 1

Report Site: VAC TEST FACILITY.SITE 2
Terminal Making Request: RAY_SQL
User ID: Administrator — 3505

Register 12345111   Facility  TS2
Inmate Name  Clinton Chuck

| Phone Number | Collect | Direct | Record | Allow | Called Party Language | Date Changed |
|---|---|---|---|---|---|---|
| 2026162040 | YES | YES | YES | YES | ENGLISH | 12/15/2000 |
| 9725428754 | NO | YES | YES | YES | ENGLISH | 12/15/2000 |
| 9726335252 | YES | YES | YES | YES | ENGLISH | 12/15/2000 |
| 9724565250 | YES | YES | YES | YES | ENGLISH | 12/15/2000 |
| 2146462000 | NO | YES | NO | NO | ENGLISH | 12/15/2000 |
| 2143965787 | YES | YES | YES | YES | ENGLISH | 12/15/2000 |
| 2145236463 | YES | YES | YES | YES | ENGLISH | 12/15/2000 |
| 2146233354 | YES | YES | YES | YES | ENGLISH | 12/15/2000 |
| 2146815544 | NO | YES | YES | YES | ENGLISH | 12/17/2000 |
| 2143652158 | YES | YES | YES | NO | ENGLISH | 12/7/2000 |

Number of Telephone Numbers for Inmate: 10

Register 55264152   Facility  TS2
Inmate Name  Williams Mathew

TELECOMMUNICATION CALL MANAGEMENT AND MONITORING SYSTEM WITH VOICEPRINT VERIFICATION

CROSS-REFERENCE TO RELATED APPLICATIONS

This application is a continuation of application Ser. No. 14/613,153 filed on Feb. 3, 2015, which is a continuation of Ser. No. 12/218,145, filed Jul. 11, 2008, which is a continuation of application Ser. No. 10/893,575, filed Jul. 16, 2004, which is a continuation-in-part of application Ser. No. 10/215,367, filed Aug. 8, 2002.

FIELD OF THE INVENTION

The present invention relates generally to the field of telephone communication systems in penal institutions or similar facilities. In particular, the present invention relates to a computer-based telecommunication system with the capacity to allow an institution to authorize, control, record, monitor, and report usage and access to a telephone network using speaker independent voice recognition and speaker dependent voice identification to ensure that access is restricted to authorized users only.

BACKGROUND OF THE PRESENT INVENTION

Generally, the need to monitor, control, record and provide detailed records of the usage of a telephone system in a controlled institutional environment is well recognized. It is common to utilize a controlled telephone system capable of monitoring outgoing telephone connections in many types of institutional environments, such as, but not limited to, penal institutions, military institutions, hospitals, schools, businesses, or specific types of government institutions. The reasons for monitoring and controlling institutional telephone systems are evident. To prevent such institutions from incurring unaccountable telephone costs, the institutions must either restrict access to outbound telephone lines or employ a telephone monitoring system to charge the responsible party for making the outbound communication. Otherwise, unaccountable telephone costs would severally hinder the availability of the telephone systems in institutions.

Therefore, it is imperative for many institutions to utilize a communication system that provides an accurate identification means for administrators to determine the individual responsible for each outbound telephone call. A communication system must also provide a monitoring means for maintaining a useful record of the communication. Additionally, the system may include a means for restricting access or a means for providing options to particular users. Considering the number of users in a large institution, different payment methods available, and the excessive call volume at many institutions, it is evident that an effective telephone management system is essential.

Providing telephone systems in specific types of highly restricted institutions, such as in penal institutions, results in the consideration of numerous additional complicating factors. Generally, outbound communication means in penal institutions are heavily regulated by the government. Therefore, communication systems implemented in penal institutions or similar facilities must meet greater security requirements often mandated by regulatory bodies affiliated with the county, state, or federal institution. Thus, the communication system used in a regulated institution must employ unique functions.

In its most general form, a penal institution's telephone system utilizes a call processor to approve and place a call, surveillance equipment or monitoring equipment, and a recording device for evidencing the conversation. Generally, these simple systems are not equipped to restrict an inmate from calling any individual or to verify the identification of a user utilizing advanced authentication techniques. However, it is preferable for the call system devices now employed in such institutions to have the capability to thwart an inmate from calling certain specific individuals or types of individuals. Without the necessary constraints on an inmate's use of the telephone system, inmates have often harassed outside parties or individuals. For example, it is generally preferred that an inmate should not be able to place a telephone call to the prosecutor who prosecuted the inmate's case or another attorney responsible for the sentencing of the inmate. In another example, it may be preferred that an inmate be prevented from contacting the victim of the inmate's crime or witnesses from the inmate's case. It has also been documented that inmates have used previous penal institution call systems to perpetrate additional criminal activities such as fraudulent schemes or specific criminal conspiracies. Specifically, inmates have been known to arrange credit card fraud attempts, the smuggling of contraband into the facility, and have even been known to arrange escape attempts over the penal institution's telephone system. Therefore, it is critical in an efficient penal institution to carefully monitor all outgoing telephone calls making a regulated penal institution telephone system a necessity.

Another concern in implementing an efficient institution telephone system is cost control. In order for a system to be cost effective the system must critically monitor and record the activities of each individual user to properly charge each individual caller for his or her outgoing calls. Typically, telephone communication systems in penal institutions provide an inmate with a telephone account upon arrival. Each individual receives an account number. There are several options for an inmate to select with respect to payment on the account. For example, an inmate may place prior personal earnings into the account. The cost of each call is then deducted from the total amount in the inmate's account until no balance remains. The inmate may choose to utilize collect call means. In addition, or alternatively, an inmate may be assigned a commissary account, where funds are added to the account based on work performed by the inmate. As the funds increase, the inmate may apply these funds to the cost of placing telephone calls.

The inmate debit account may be located onsite, at a central office facility, or at a third-party site. The inmate debit account may alternatively be controlled by the inmate's family. For example, the inmate's family may control the inmate's access to the debit account either remotely (e.g., by using the Internet, accessing a toll-free/pay to dial telephone number, using a mail form, etc.) or by visiting the prison facility. The inmate's family may add funds to the debit account and thereby control the call volume allowed to the inmate.

Another requirement of a secure telephone management system in a penal institution is the accurate identification of the telephone call participants. Generally, it is common in a penal institution to assign each inmate a personal identification number (PIN). When an inmate attempts to place a telephone call, the inmate must supply a valid PIN to gain access to the telephone system. However, a primary problem with this identification method is the ease of obtaining another inmate's PIN. For example, individuals who commonly forget their PIN may write it down, increasing the possibility that an unauthorized individual will view the PIN and use it. In addition, if a PIN number is compromised and utilized by an unauthorized inmate, the unauthorized inmate may then be able to call certain individuals who are restricted to that inmate, since the unauthorized inmate is no longer using the proper PIN associated with that inmate. In known systems, the PIN identification method is incapable of verifying that the individual who supplies the PIN is the actual specified inmate. Some systems have attempted to improve security by requiring the use of a debit card in conjunction with a PIN. The use of the debit card will only allow access to an inmate's account if the correct associated PIN is supplied. This method, however, provides only minimal additional protection because a debit card and its associated PIN can often, with or without force, easily be taken from another inmate, or given to another inmate, especially in the violent atmosphere of a penal institution. For example, one inmate may threaten another inmate in order to obtain such information. Alternatively, one inmate may provide certain services in exchange for the use of another inmate's telephone privileges. The possibility that two inmates will exchange accounts also exists, thereby allowing them to contact people that would normally be restricted to them.

Further attempts to obviate security concerns include requiring personal information, in addition to a PIN, to be supplied by the inmate/user. For example, a user might be prompted to supply a PIN as well as certain information that may only be known to the user. A common example is a request by the call system to provide their mother's maiden name. This provides an additional security measure, but again is minimally secure because such information can easily be obtained in a correctional facility. It would therefore be desirable to develop a telephone management system that incorporates an improved method of identification and/or verification.

Another required feature of a telephone management system for a penal institution or similar facility is a means for restricting calls placed by a user (e.g., an inmate). It is well documented that inmates often try to harass individuals related to their arrest or confinement, such as judges, prosecutors or witnesses, etc., through telephonic communications. Penal institutions have attempted to prevent this by restricting the telephone numbers each inmate is able to access. For example, a system may utilize a PIN or other identification means to access a list of telephone numbers that the inmate may not call, or alternatively, the system may access a list of numbers that the inmate is authorized to connect to (i.e., the inmate can only call the numbers appearing on the list). Telephone numbers placed on the restricted list can include any individual related to the conviction (e.g., the arresting police officer, the prosecuting attorney, etc.), while telephone numbers placed on the permitted list may be, for example, close family relatives. The system may also limit the amount of time each inmate/user is permitted to conduct each outbound telephone call through the system. Furthermore, restrictions may be regularly updated. For example, if an inmate misbehaves, the inmate's telephone privileges may be further limited or revoked completely.

Penal institutions are also concerned with monitoring the activities and communications of inmates. Monitoring telephone activities is necessary to restrict connections to illegal activities outside of the institution. Three existing types of call monitoring techniques are known in the art. The first technique is live monitoring. Live monitoring requires an operator or other individual to listen to each telephone call and alert the proper authorities if necessary.

The second type of monitoring involves recording the telephone conversation via a common recording device. A common example of this is a recording device such as a magnetic tape drive. This type of monitoring may be continuous or intermittent depending on the degree of security required for each inmate.

The third type of monitoring is known as passive monitoring. Passive monitoring may be activated when certain keywords are spoken. In addition, passive monitoring may be activated if the telephone call at the termination end is transferred to a third party via certain known detection means such as "click and pop" detection, etc.

Penal institutions currently record most inmate telephone calls, with the exception of lawyer-inmate communications which are generally prohibited by law. Typically in the art, monitoring may occur using any combination of the three methods (e.g., live monitoring, electronic recording monitoring, or passive monitoring). However, it would be desirable for a telephone management system to embody a means for determining which level of telephone monitoring should be employed for each telephone call. For example, it would be advantageous to flag certain individuals in an inmate's profile as highly suspicious. If the inmate initiates communication with the flagged individual, the system will alert a live operator to monitor the system. In such a system it is essential that the system correctly identify the called individual to avoid unnecessary expenditure of live operators.

Alternatively, the inmate telephone call system may utilize a remote alert notification system wherein the system contacts an operator when a violation has occurred. The system may contact the operator utilizing telephone means, paging means, etc. This notification system may be set to call the operator a limited number of times or until the alert has been noted in the inmate telephone call system. The operator may then access information about the alert remotely using the telephone, Internet, or any other such remote access means.

In order to alleviate some of the problems and concerns discussed herein, many penal institutions have implemented certain task-specific advanced systems. Generally, these "advanced" systems known in the art comprise several features.

For example, it is known in current systems to employ permanent call blocking. Specifically, it is known in the art to block an inmate or group of inmates from dialing certain telephone numbers. Most systems also prevent inmates from talking directly to live operators. This prevents inmates from requesting that the operator forward a call or provide additional telephone numbers allowing the inmates to harass or locate additional parties. Furthermore, current systems block "1-800," "1-900" and other like telephone numbers including toll-free and pay-to-dial telephone numbers. In addition certain institutions may elect to block country codes, specific area codes, or other third-party numbers.

Current systems known in the art may also utilize a feature commonly referred to as "selective" call blocking. As discussed, "selective" call blocking may be employed to thwart inmates from establishing a connection with a selected group of individuals (i.e., with the home telephone of prison guards, wardens, indictment witnesses, trial witnesses, police officers, judges, etc.). It is also foreseeable that the telephone numbers of the family members of these specific individuals may also be blocked.

Some current systems also limit the use of specific long-distance carriers. This feature proves useful in limiting unnecessary costs incurred by employing alternating carriers.

Several current systems utilize features commonly referred to as "flash hook" prevention or "click" and "pop" prevention modes. These systems prevent inmates from extending the current outgoing telephone call and entering a new telephone call with a new number without fully terminating the original telephone call. For example, this prevents an inmate from utilizing common call forwarding features and the like.

In addition, some current institutional telephone systems electronically or manually disable the keypad after a telephone number is dialed and the telephone call is connected. This feature prevents inmates from interacting with telephone games and lotteries, and in certain older systems, prevents the inmate from achieving an unrestricted dial tone.

Another common feature employed by institutional systems is three-way call prevention. This feature prevents an inmate from instructing the called party to bridge the telephone call to another telephone number.

Other known systems in the art may exhibit other regulatory features. For example, generally, telephone communication systems allow an institution to limit the duration of a telephone call and/or to limit the cost of the telephone call. These types of features further allow a facility to customize the telephone call systems thereby preventing unrecoverable expenditures.

Another control used by current institution telephone systems is the use of certain aspects of biometric recognition for the identification of users or inmates (i.e., the calling party). However, systems known in the art have only used biometrics to a limited extent. It is highly beneficial for communication systems in penal institutions to incorporate biometrics as an additional security device. Biometric recognition is commonly available in a number of fields. For example, biometrics recognition has found a number of security uses, including common usage, in credit card systems and building security systems. Biometric information includes fingerprints, rand geometry, voiceprints, retinal patterns, iris scans, signatures, infrared facial patterns, and all other sources which constitute unique physiological characteristics and which can assist in establishing a person's identity. Various devices exist which can scan one or more biometric characteristics and digitize the information.

The features discussed herein are present in several known systems. For example, one such system includes automatic account number validation and billing management. This system prompts a user for an account number and compares the number inputted to a number stored in a database to determine validity. If the account number is valid and found in the database, the system completes the predetermined telephonic connection. If the number is not in the database, and therefore invalid, the system will utilize voice prompts to request re-entry of the number or provide further instructions. The system attempts to locally automate and simplify the process of payment for routing calls without live operator assistance, but does not address additional security concerns that may exist in specific facilities, such as in a penal institution. Furthermore, this system does not provide for protection measures to confirm that the individual supplying the account number is the individual entitled to the use of the account (e.g., the system does not use any biometric identification to verify the identity of a user). In such a hostile environment as in a penal institution, an account number may easily be obtainable through coercion or by force. Additionally, the system does not provide any means of monitoring the conversations taking place or restricting which individuals are accessed by the user.

Another known call management system enables prepayment of telephone calls utilizing a debit system. Specifically, a user of the system obtains a special code by depositing a prepayment. The prepayment is stored in a database on the call management system for use in verifying calling party calls. To access the system, a user dials a special number and inputs a user-specific code for verification followed by the number of the party to be called. Next, the code is verified by the system. If verification is successful and sufficient funds are available, the call is connected. The prepayment amount, minus deductions for the running cost of the call, is tabulated as the call progresses. The call terminates either when the prepaid funds are exhausted in the user's account or when either party disconnects. This system also includes steps to prevent the same access code from being used at different terminals. However, it does not have a means for selecting the call type or a call monitoring means. The system also fails to perform an advanced verification means to identify and authorize a user.

Also known in the art is a multilingual prepaid telephone system capable of interfacing with a public switched telephone network (PSTN). In this system, each user is assigned a PIN and a credit account. To access the system, a user first dials a number to access the telephone system and chooses a language for all subsequent voice prompts. The user then supplies a PIN, which is compared against a list of numbers in a database. If sufficient credit is available for the duration of a telephone call to the destination number, the connection is completed and a timer is set for the available duration of the call. The call terminates either when the allowed amount of time for the call expires or if one party member hangs up the telephone line. If the latter situation occurs, the system computes a new available credit balance for the user's account. However, this system fails to provide a selection means for the user, such as the ability to choose the type of call to be placed (e.g., collect, debit, international, etc.). Further, it does not have any call monitoring means and would therefore be unacceptable as a communication system for a penal institution.

Yet another known system in the art is an integrated commissary system for receiving and processing orders in an institutional setting. The commissary system is designed for use without access to a PSTN. User status and inventory status are stored in an onsite database. To access the database, a user provides identifier information and item selections through selected telephones. The selections are compared against the onsite database using a processor. If the user is authenticated and the requested items are available, the processor generates transaction records, updates user commissary information, and correctly adjusts inventory. The updated information is stored in a file that may be used for record keeping or archival purposes. However, as described this system does not teach a commissary system for use with a PSTN. It also fails to teach multiple authentication means and would therefore be unacceptable for use in a penal institution.

Another known system includes a software process for real-time call rating and debiting so that a subscriber's account balance is not exceeded. The method used in this system estimates the time when the user's balance will expire by using the total charge per second average. The process then determines the time remaining by dividing the account balance by the average charge per second of all telephone calls, and the time limit for the call is then set accordingly. This method is useful if the rate for long distance calls is not known locally. However, the system does not allow for other types of calls, such as collect calls, to take place. Furthermore, the system does not provide an advanced call monitoring apparatus with an advanced authentication apparatus (e.g., no voice identification for verification is used in this system).

Still yet another known system provides automated public telephone control for charge or collect call billing. The apparatus embodies a microprocessor system controlling voice prompting, recognition of responses, network signaling, recording of calling details, and verification of account numbers. The system provides for an automated telephone billing for public telephone systems. The system offers a plurality of billing methods, such as billing to a credit account number, to the called party (collect calling), or to a third party. An additional aspect of this known system is the recognition of voice utterances from other signals and called party spoken words (i.e., the system can recognize the word "yes" when spoken by any individual). However, the system does not identify or verify the individual speaking. Furthermore, this system does not provide a means to identify the user or verify that the user is not partaking in fraudulent activities. Finally, this system fails to teach a monitoring and call control means.

Still another known system in the art includes a means for detecting three-way call attempts by monitoring for pulses of energy indicative of a hook-flash. The system includes a low pass filter for passing energy signals having frequencies below 500 Hertz ("Hz"), preferably in the range of 100 to 300 Hz, and an energy detector for detecting specific electrical energy pulses passing through the filter and having a predetermined minimum magnitude. The system also includes a software window analyzer, which cooperates with the energy detector to detect specific events, such as sound, occurring on the telephone line during a predetermined time window after the detection of the aforementioned energy pulse. The software window analyzer includes a timer means that is activated by the detection of the energy pulse, and a sound means for detecting the occurrence of sound on the telephone line during at least one of multiple windows of time defined by the timer means. The non-occurrence of sound on the telephone line during a specified time window is used by the system to confirm that the detected energy pulse is in fact a three-way call attempt. A counter means is further implemented for counting specific energy pulses detected by the energy detector during the time window when the remote party is using a pulse-dial telephone.

Also known is a collect call system which automatically routes long distance calls without intervention of an outside service or operator. This feature enables private public telephone owners, as opposed to primary telephone companies, to receive revenue for completion of the call. The invention comprises the steps of providing the calling party with voice prompts, receiving voice or dialed signal information about the calling party in response to the voice prompts, either voice or dialed signals, locally recording the information about the calling party, providing the called party information about the calling party, and reacting to a variety of provided signals by either the called or calling party. The known system does not provide for other possible payment methods. The system is further limited by its lack of telephone call monitoring ability and calling party identification means, and is therefore unsuitable for use in penal institutions.

There is also a known system in the art that utilizes biometric verification means for determining if a user is authorized to use a credit or identification card. This system introduces a method embodying the steps of receiving biometric data from a cardholder, scanning the card to obtain user information, and retrieving authorized card owner information stored in a database. The information obtained from the three sources (i.e., cardholder, card, and database) is analyzed and compared to verify that the cardholder is the authorized card owner. A number of possible biometric features may be used such as voiceprints, fingerprints, digital photography, and retinal scans. The system compares the user information to an already existing database, which lessens the possibility of incorrect identification. Further, the system provides a reliable means for verifying a user in a credit or debit card system. However, the system fails to implement additional biometric means useful in identifying a called party and fails to apply these features to specific institutional functions.

Systems are known in the art for controlling, monitoring, recording and reporting telephone communications. The system deals primarily with the identification of a user through use of a PIN and restricting telephone communications through a profile accessed by the PIN. The system further contemplates means for monitoring and recording communications. The system may also incorporate an improved method of monitoring calls. The method includes a means for detecting tones commonly associated with call bridging and call forwarding attempts. For example, it can detect tones such as ring signals, busy signals, special information tones (SIT tones), dual tone multi-frequency tones (DTMF), call progress tones or other similar tones characteristic of the placement of a telephone call. However, this system is limited by detection of certain sounds which may not be readily machine-recognizable. For example, it is foreseeable that interference, background noise, or compressed voice data may inhibit the detection of the tones.

Another known system is used for the verification of a calling party, called party and a secure connection by using secure telephone devices, such as the Micro MMT Sectel® 1500 BDI. Specifically, in this system, the calling and called parties supply voice data which is encoded and transmitted over a telephone network. Both users hear the alternate party's recorded voice data and verify that the supplied voice data is correct. The call is established only if both parties verify that the called party has provided the correct voice data. However, as is known in the art, the secure telephone devices are often costly and would not provide adequate security in a penal institution or similar facility. Additionally, the system does not allow for different possible payment methods for calls or call management. Another system known in the art uses voice recognition as an identification means, including speaker recognition by using two processing units. The first unit receives voice characteristic information by recording specific words spoken by the user. The information is analyzed and stored in a database. The system prompts the user for additional information, which is then received by a second processing unit. The results of the analysis of the second processing unit are sent to a first processing unit with the previously stored information. A comparison of the analyses determines if the user is authorized. This system is limited by its inability to manage call restrictions and lacks monitoring capabilities.

Another system known in the art permits users repetitive access to a multitude of systems. The system requires an initial enrollment phase for access. The enrollment phase consists of extracting biometric data to be stored for future use. The format of the data is compatible with a plurality of verification identification systems including voice recognition, fingerprint identification, and retinal scan identification. However, there are no restrictions to the system or further monitoring means during use of the system, which are essential for systems within a penal institution.

Finally, a system is known that uses acoustic and non-acoustic attributes to identify. An initial profile is created by both utterances spoken by a user and non-acoustic information, such as keying in a user's customer number or social security number. The acoustic recognition contemplates the usage of a plurality of voice recognition methods. The system is limited in its ability due to the lack of monitoring or call management abilities.

In view of the foregoing, clearly there exists a need for an improved method and apparatus for managing an institution's telephone call system. There also exists a need for an improved method for controlling access to an institution's telephone call system by use of advanced authentication and verification techniques including integration of voice or other biometric identification means. Furthermore, a need exists for an improved telephone call monitoring system for a penal institutions or similar facilities that addresses the increased concerns of monitoring the call activity of the calling party. In particular, a need exists for a computer-based telecommunication system with the capacity to allow an institution to control, record, monitor, and report usage and access to a telephone network.

SUMMARY OF INVENTION

The present invention embodies an improved telephone call management system using improved identification means including biometric identification. For example, the identification means may include the utilization of speaker independent voice recognition in conjunction with speaker dependent voice identification. This, in combination with a user-specific personal identification number ("PIN") provides an improved method of identifying and restricting a user's access and utilization of an institution based telecommunications network. In addition, the present invention incorporates control means, monitoring means, recording means, and a reporting means for an institution based telecommunication network. The present invention may implement a debit card platform or other such payment methods. The system of the present invention may be implemented in a variety of facilities including, but not limited to, penal institutions, mental institutions, nursing homes, rehabilitation centers, correctional facilities, government agencies; private and public business, and the like.

One objective of the present invention is to provide a telephone call system including a means for identifying and authenticating an institutional calling party. For example, it is foreseeable that these means may include, but not be limited to, the use of an institution-assigned inmate specific debit card requiring specific authentication data, the use of biometric recognition devices, the use of radio frequency identification devices, etc.

As one specific example, the system may require that a user provide a valid PIN and corresponding voice identification to access the system. The system can verify the PIN and match the provided voice identification with a stored record. Further, the invention ensures that the voice identification includes certain words (e.g., the caller's name). This prevents an inmate from using an easily mimicked voice sample (e.g., the system would reject a voice sample that consists of a user simply whistling, coughing, or remaining silent).

The system of the current invention is designed to operate in either a local area network (LAN) or a wide area network (WAN). In a LAN configuration, the telephone system is controlled by a configurable switchboard device that routes calls, provides voice prompts, and responds to menu selections. Calls placed by users of the system are routed through the switchboard device and connected to the proper outgoing trunk based on the type of call placed (e.g., collect, debit, etc.). The switchboard tests outgoing trunks as calls are placed. If no dial tone is detected, the trunk is taken out of service for a pre-programmed period of time. An integrated cross point switch enables any telephone to access any available outgoing trunk. The cross point switch also allows calls from other switchboard modules to be routed to alternate modules for completion. During periods when all trunks are in use on the module at the telephone connection, calls can still be completed provided that some trunks are available on alternate modules. The switchboard device also has an integrated channel bank, allowing for fully integrated T-1 capability. This allows calls to be processed either over analog or digital trunks as required. The architecture of the switchboard allows it to accommodate multiple processors, eliminating system overload during extremely busy periods of telephonic communications.

The switchboard is connected to a site server, which is commonly referred to as an ITAC (Inmate Telephone Access Control) in penal institutions or a UTAC (User Telephone Access Control) in certain other types of institutions. This device serves as the main database for the telephone management system. It has the ability to log and record details of all telephone calls placed through the system and store them for a period of time defined by the institution. The ITAC/UTAC also digitizes all information for the digital T-1 trunk. A recorder, which may be integral to the system or remote to the system as a separate storage means attached to the ITAC/UTAC, is responsible for recording the telephone calls and storing them in one or more databases depending on the size of the institution or the amount of data which must be archived by the institution and the capability of the storage means.

In the system of the present invention, a new user receives a PIN, account number, cell location and other identification information. This identification information is stored in a database preferably located at the ITAC/UTAC. Further, a new user is required to speak his or her name when subscribing. This sample speech, also stored in the database, is utilized as voice identification data every time a user places a call. Specifically, the system prompts the user to speak his or her name and the user's response is compared with the original speech sample using speaker dependent voice identification. Importantly, the system includes methods for ensuring that the original speech sample is the user's name and is not an easily mimicked speech sample, and that the speech captured when placing a phone call matches this original sample.

Connected to the ITAC/UTAC are a number of administrative and investigative workstations used to create, edit, and monitor user accounts and telephone calls. The investigative workstations may be used to listen to the outgoing telephone calls in real time or to access calls stored on the server or other type of database or storage means.

In a WAN configuration, the site server is connected to multiple switchboard devices that are located in separate institutions. In this embodiment, the ITAC/UTAC serves as the database location for the entire system. Administrative and investigative workstations may be located at every facility. Alternatively, it is foreseeable that one or more sets of workstations at a central facility may be used to administrate all user accounts.

User-friendly software utilizing a graphical user interface (OUI) or other types of on screen display (OSD) capable devices may be employed to administer all user accounts of the telephone management system. The software allows a system administrator to provide calling restrictions at all levels of operation. Such restrictions may include, but are not limited to, the total number of minutes allowed, the total number of calls placed, dates and times calls are allowed, telephone exchanges allowed to be accessed, the number of times the debit inquiry system may be used, and other like restrictions. If a WAN configuration is being used, such restrictions can be set for each institution on the network or for the entire telephone network. In addition, it is contemplated by the present invention that different divisions of each institution, such as cellblocks in a correctional facility, may also be given global restrictions. Since each division of the institution is linked by a LAN/WAN, changes can be made at any of the different institutions and then be applied globally or locally.

Additional restrictions and options are available for individual user accounts. For example, each user may be assigned a language for the telephone system's voice prompts. Another option is the ability to limit the telephone terminals a user may call from or the payment method utilized for each call made.

The called party that a user may contact may also be restricted. For example, certain exchanges or telephone numbers may be blocked. Alternatively, users may have to submit a pre-approved list of numbers to the system administrator. Once the user list has been checked to ensure that the inmate is allowed to call those people, the inmate may only call the people on this list.

Certain options for contacts on the pre-approved list may be set for each person on the list. For example, a language for each person may be set. The voice prompts for that contact will then be in that language. Contacts may also be assigned specific recording restrictions. For example, a conversation between an inmate and an attorney may require specific recording restrictions. Other options such as if a caller can only place calls collect or by debit, may also be specified.

An additional feature of the software is that it can create a debit account for each user and monitor the account balance. The cost of each call is subtracted from the account after the call is completed. Also, an account administrator can manually add or subtract funds to individual accounts. The inmate's access to the account may alternatively be controlled by the inmate's family. In this configuration, the inmate's family controls the inmate's funds and thereby controls the inmate's access to the account.

Since the site server logs data about each call, the present invention is designed to provide reports, either in electric or hard copy form, utilizing specific data from the database. Therefore, a system administrator can track important statistics such as the net profit of the telephone management system during a certain time period. It is foreseeable that the software may incorporate extensive data processing services for providing a user a multitude of correlated dates.

In one embodiment of the present invention, when a user attempts to access his or her account to place a call, the user may be requested, via voice prompts, to select a voice prompt language and enter a user-specific personal identification number. The information entered by the user is compared with information stored in the database for that specific user. If a corresponding PIN match is not achieved, a verification error may be provided and the system may request a re-entry of the PIN. It is foreseeable that if the second attempt fails to provide a match, the individual may be denied access to the telephone system and an official may be notified.

The system can also use speaker dependent voice recognition as an added level of security. For example, when a user is registered (i.e., given a PIN), the system can also store a sample of the user's speech and associate that sample with a PIN. Then each time an inmate attempts a call by entering the PIN, the system prompts the inmate to repeat the previously provided sample. The system utilizes speaker dependent voice identification to ensure the inmate placing the call has the same voice as the stored sample.

The system can also use speaker independent voice recognition to ensure the sample of speech is a certain key word (e.g., the inmate's name). This prevents an inmate from storing a sample (e.g., a whistle, cough, etc.) that is easy to mimic.

Once the inmate's identity is verified, the system may announce the inmate's call restrictions. For example, the system may access a pre-recorded menu of restrictions informing the inmate of specific restrictions, such as total telephone usage time, individual call length, and different payment options, such as collect call means or debit account means. The system may then connect to the desired called telephone number, provided that the number is on the accessible number list for that user. The system may first prompt the person called to select a language for future voice prompts. The language selected may then be saved in the database. Then, the called party may be informed, via voice prompts or other like means, the identity of the calling party and location from where the calling party is located (e.g., John Doe from Peters State Penitentiary). The called party can accept or reject the caller through voice response, DTMF tones, or other like input means. If the called party provides a negative response (i.e., rejecting the call), the called party may select an option blocking calls from this caller, institution or similar calls in the future. The data may then be stored in a database. After accepting the call, the called party may be prompted to supply identification information (e.g., social security number, user name, date of birth, etc.). Additionally, the called party may be asked to provide a PIN to be used for future authentication. The information may be used to later identify the called party and verify permission for communication with the calling party. Alternatively, if the called party is on a pre-approved list, the call may proceed without any voice prompts in a similar manner as a normal PSTN telephone call.

The system may also utilize other authentication means to provide access to the telephone management system. For example, biometric data may be required to access the system. Biometric data includes, but is not limited to, voiceprints, face architecture, signature architecture, fingerprints, retinal prints, hand geometry, and the infrared pattern of the face. Such data may be acquired from users either from prior supplication to biometric systems or from the acquisition of the data from the user upon the creation of a telephone account for use with the system. This data may be stored along with the user's PIN in the user's account profile or some other storage means to be used later as an authentication device.

When a user attempts to access the telephone system at a later time, the user may hear a series of voice prompts directing the user to first supply a PIN and then supply the same form of biometric information that is stored in the database. For example, if the user's thumbprint was stored digitally in the database, the user would have to supply a thumbprint to a device capable of scanning it and converting the resulting data to the same format as the information in the database. The scanned data would then be compared to the information maintained in the storage database. If a positive match occurs based on the PIN and biometric data entered, then the user would be granted access to the system subject to user specific restrictions.

Biometric authentication means may also be implemented to authenticate the called party. In this type of system, the authentication may include one or more biometric authentication means in addition to non-biometric authentication means. In this embodiment, before the called party is allowed to converse with the caller, the called party may be asked to supply voice authentication and/or provide a PIN. This information may be stored in a database either prior to a user's first call or when the first call is made. Similar to the method of speaker independent voice recognition and speaker dependent voice identification (utilized to verify inmates), the system may require the called party to speak a specific word or phrase (e.g., the caller's name). Speaker independent voice recognition is used to verify what the called party spoke. Again, this additional step ensures that the called party provides a significant voice sample that is not easily mimicked. If the data has been stored prior to the call, the called party would have to state the pre-recorded phrase. The recorded data would then be compared with information in the database. If the data is in compliance with the information in the database to within some pre-assigned statistical threshold, the system would allow the call to proceed and a connection would be made. If the data had not been stored prior to the call, it would be retrieved from the called party and used for future voice authentication.

A further authentication means that may be utilized by the present invention is the use of radio frequency ("RF") authentication. The user can be required to have in the user's possession some type of radio frequency identification technology to access the telephone system. This may be accomplished in a number of ways.

In a first example, each user of the system would be required to wear an RF band attached preferably to the ankle or wrist. The RF band may be active, passive, or neutral. For example, the frequency of the band is unique to each wearer. An active RF band contains a transponder that either intermittently or constantly emits an intermittent RF pulse that is detected by a series of sensors placed about the user's location. The sensors relay the detected data to a remote or central database containing a processor that calculates the location of the wearer in one of two usual methods known in the art, as well as those methods not yet contemplated.

The first method involves triangulating the user's source, which requires two or more sensors or a sensor on a rotating platform. The analyzing system detects the angle of the incident pulse with the sensor and uses this data from multiple detectors to triangulate the source of the user.

A second method of detection involves the analysis of the time of flight of the emitted RF pulse. This method requires the same sensor configuration as the triangulation method. In this method, the sensor measures the time it takes each pulse to arrive at the sensor location as compared to the pulses that occur at a regular rate in an active RF device. From this data, the analyzing system can determine an accurate distance from the sensor that the user must be located within some minor degree of error. By combining this information from a multitude of sensors, the location of the person can be triangulated.

Active RF bands may be used in the present invention to locate an individual within the facility housing the telephone system. When an individual attempts to access a telephone terminal, the system can determine the user accessing the terminal since the location of each individual is known. The options for that specific individual can then be used by the phone terminal allowing the user to place a call.

It is advantageous to use active RF bands because they are very accurate for determining the location of an individual. However, most active systems have a relatively short battery life and require constant recharging. A passive RF device may also be used with only slight modification to the system. A passive RF device works by emitting a pulse only when activated by some other emitted pulse. In this embodiment, the sensors may also be equipped with RF pulsing devices designed to activate the user's RF devices. When a user attempts to access a telephone terminal, the system sends out a pulse. As a result, the user's RF device is activated and the person using the telephone terminal is authenticated. The user's specific user options can then be forwarded to the telephone terminal the user is utilizing.

Passive RF bands may be used in conjunction with the present invention for a variety of applications. For example, each telephone may be located in its own booth and fitted with an RF emitter and sensor. When a person attempts to access a telephone account at a terminal, an emitter terminal can send out a pulse activating a passive RF user device. In turn, the RF device may emit a responsive pulse. Subsequently, the sensor on the terminal can detect the responsive pulse. Using time of arrival analysis, the user can be located and verified, thereby authenticating the telephone terminal.

Neutral RF bands may also be used in the present invention. Neutral RF bands function by reflecting an incident RF pulse with a slight modulation, which is unique to each user. In response, the sensor on the telephone terminal can record the reflected wave and forward the information to analyzing software. The analyzing software subtracts off the original pulse signal to determine the modulation frequency of the user's RF band, thereby authenticating the user at the terminal. The correct user options can then be supplied to that specific terminal.

In another example of the present invention, a debit card may also be used in conjunction with a PIN. At each terminal, the user may be instructed to scan a user-specific debit card into a debit card reader and enter a corresponding PIN in order to gain access to the system. Alternatively, a user may enter information related to a debit card in any of a number of known procedures followed by a PIN. This method of authentication may also be combined with biometric and/or RF identification means.

After a user is authenticated and a calling party is contacted, the present invention provides monitoring and safety means that are active when a call is in progress. Call recording is the primary security means. There are three types of call recording utilized by the present invention. However, numerous other call recording systems in accordance with the concepts and objectives of the present invention may be incorporated.

In a first call recording protocol, by default, all calls are logged and recorded unless otherwise specified in a user's contact file (e.g., calls to an attorney are not recorded). It is foreseeable that calls may be archived on a site server or other database storage means for future reference.

A second type of call recording implemented in the present invention is referred to as passive recording. This type of recording may utilize voice recognition software to listen for certain key words or phrases in a conversation. If a key word is uttered, the system records the rest of the call and alerts the system administrator, proper authorities, or implements other security procedures. For example, in a penitentiary, if the word "drugs" is used in a conversation, the system may be activated thereby recording the remainder of the conversation.

The third type of call recording that may be utilized in the present invention involves an operator scan of a user conversation. In response to a flagged conversation, the operator may have the discretion to selectively record the conversation. For example, using the same software used to administrate accounts, an operator can selectively listen to conversations and record suspicious conversations for future reference.

Third-party call detection is another security feature that the present invention may utilize. The system software may have the ability to detect whether a third party is connected upon the origination of the call. If a third line is detected, but not authorized, the software will end the communication and notify the authorities that such an event has occurred. The telephone management system may also include a feature that terminates the telephone call if more then a certain number of individuals are included in the conversation. It is foreseeable that this may be accomplished by voice recognition means.

Another type of third-party call detection involves the detection of hook-flash events. A hook-flash event occurs when a user hangs up the telephone for only a brief instant during a telephone call, just long enough to not disconnect the line. This is usually characteristic of a switch between lines on call waiting or to initiate a three-way conference call. If the telephone system's software detects a hook-flash event by either party to the call, it will terminate the call and alert the authorities. This feature of the system prevents unauthorized third parties from taking part in telephone conversations.

An additional security means incorporated in the present invention is the locking of the telephone keypad after a connection is made. This prevents the caller from dialing out to a third party that has not been approved after a pre-approved connection has been made. Alternatively, the system may allow the user to only press a predetermined number of keys after a connection has been made. This allows an authorized user to access an automated service and enter menu selection keys.

The human voice has the capability of creating DTMF tones also. In order to differentiate tones created by a user's voice from tones created by the telephone keypad, the present invention incorporates software which monitors the frequency of DTMF tones. Such software is capable of determining the source of the DTMF tones.

One objective of the present invention is to provide an efficient and reliable user identification system using biometric identification means wherein speaker independent voice recognition and speaker dependent voice identification are used to verify the identity of a user each time a user attempts to place a telephone call.

Another objective of the present invention is to capture a significant sample of a user's speech when the user subscribes to the system and to request the user to repeat this sample every time the user places a telephone call to provide an improved voiceprint identification system for use in a telecommunications call management and monitoring system.

An additional objective of the present invention is to provide an improved telephone communication monitoring system. Another object of the present invention is to provide an improved call management system using a user-friendly operating system.

An additional object of the present invention is to provide an improved call management system capable of operating in a LAN or WAN.

A further objective of the present invention is to permit alterations of call restrictions and options through a computer control unit.

Still another objective of the present invention is to provide a means of restricting communication options to certain users.

An additional objective of the present invention is to incorporate biometric verification, including voiceprints, face architecture, signature architecture, fingerprints, retinal prints, hand geometry, infrared pattern of the face, etc., with a debit card system. Yet another object of the present invention is to utilize a combination of a PIN and a voiceprint to accurately verify a caller.

Still another object of the present invention is to restrict voiceprints to certain keywords or phrases to ensure that the voiceprints can be used accurately for subsequent identification of a caller.

Yet another objective of the present invention is providing called parties with the option of rejecting the call and blocking similar calls in the future.

Another object of the present invention is to incorporate an active RF device for use in authentication in a call management system.

A further object of the present invention is to incorporate a passive RF device for use in authentication in a call management system.

Another object of the present invention is to incorporate a neutral RF device for use in authentication in a call management system.

Still another object of the present invention is to incorporate advanced software incorporating at least a monitoring module and an accounting module.

BRIEF DESCRIPTION OF THE DRAWINGS

A further understanding of the present invention can be obtained by reference to the preferred embodiment and alternate embodiments set forth in the illustrations of the accompanying drawings. Although the illustrated embodiments are merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention. For a more complete understanding of the present invention, reference is now made to the following drawings in which:

FIG. 12 depicts a sample telephone location maintenance screen for use with software contained in the call management system of the preferred embodiment of the present invention.

FIG. 13 depicts a sample facility number control screen for use with software contained in the call management system of the preferred embodiment of the present invention.

FIG. 14 depicts a sample telephone number control screen for use with software contained in the call management system of the preferred embodiment of the present invention.

FIG. 19 depicts a sample manual financial transaction screen for use with software contained in the call management system of the preferred embodiment of the present invention.

FIG. 25 depicts a sample financial history screen for use with software contained in the call management system of the preferred embodiment of the present invention.

FIG. 26 depicts a sample call records screen for use with software contained in the call management system of the preferred embodiment of the present invention.

FIG. 30 depicts a sample call detail screen for use with software contained in the call management system of the preferred embodiment of the present invention.

FIG. 33 depicts a sample query result screen for use with software contained in the call management system of the preferred embodiment of the present invention.

FIG. 35 depicts a sample account telephone number list report for use with software contained in the call management system of the preferred embodiment of the present invention.

DETAILED DESCRIPTION OF THE PREFERRED EMBODIMENTS

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present invention. The following presents a detailed description of a preferred embodiment as well as alternate embodiments such as a simpler embodiment or more complex embodiments for alternate devices of the present invention.

Figure 1:
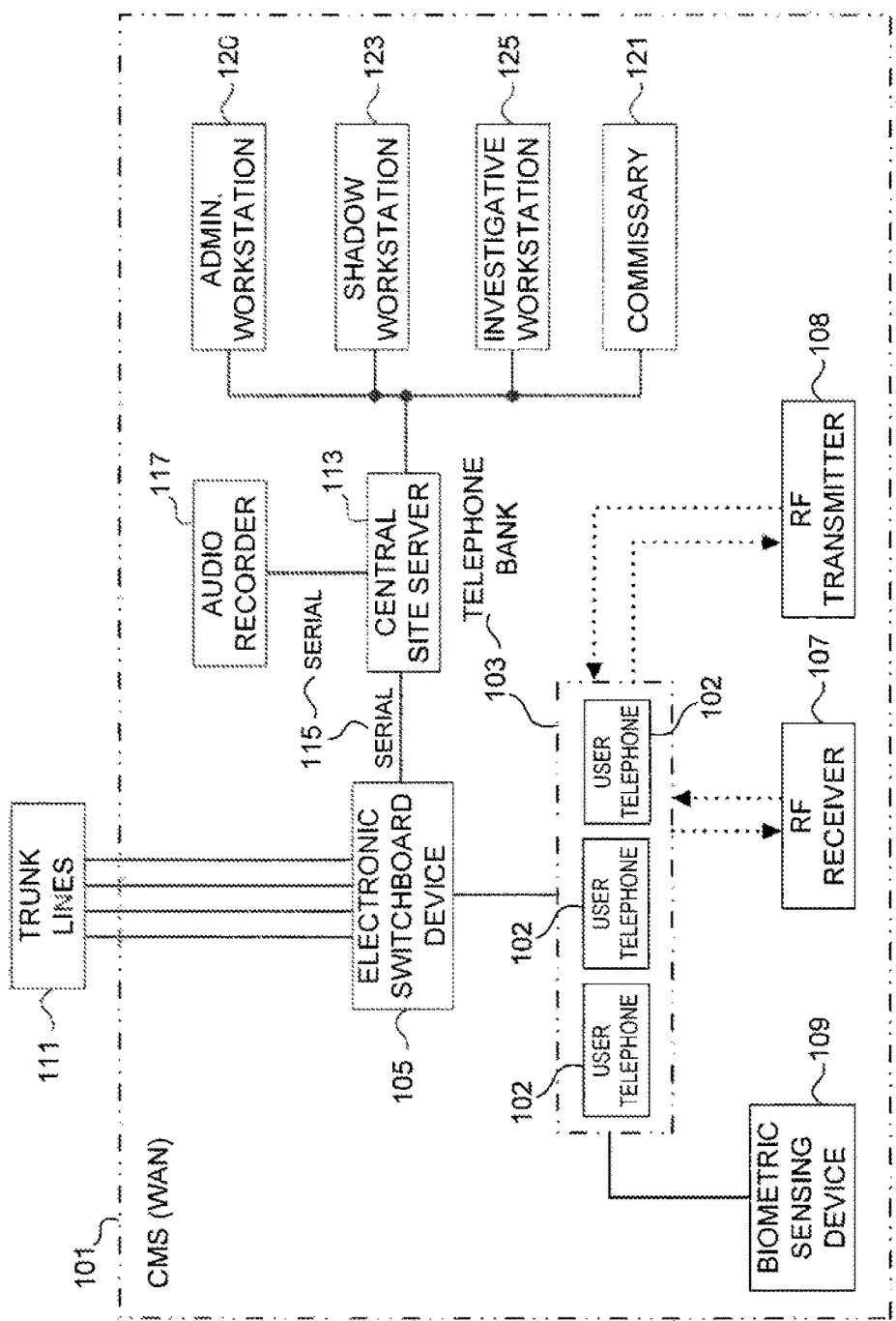
FIG. 1 depicts a schematic representation of the call management system of the present system configured to operate on a wide area network (WAN).

Referring first to FIG. 1, shown is a call management system 101 configured to operate in a WAN (Wide Area Network) according to the present invention. A plurality of user telephones 102, wherein the actual number of telephones depends on the desired capacity of the institution call system, are incorporated into a telephone bank 103 and are connected to an electronic switchboard device 105. It is preferred that telephone bank 103 may be centrally located within a facility to allow for centralized monitoring. However, it is foreseeable that telephone bank 103 may be located at a multitude of locations internal or external to a facility to allow for efficient monitoring. Each user telephone 102 is equipped with biometric sensing device 109, such as a retinal scanner, fingerprint reader, etc., or any combination of biometric devices, so that the acquired biometric data can be used for user authentication. Alternatively, for efficiency, a single biometric sensing device 109 may be employed for a multitude of user telephones 102. Additionally, each telephone may incorporate RF receiver 107 and RF transmitter 108 to provide RF signals for authentication purposes. In this scenario, it is foreseeable that each user is be required to wear an RF transmitter 108 device to transmit radio waves to the RF receiver 107. RF receiver 107 is integral to telephone bank 103 or may be remote to telephone bank 103. Each RF transmitter 108 may be uniquely encoded to a specific authorized user. The encoded signal for RF transmitter 108 may be altered on an intermittent basis depending on the security desired at the institution. RF transmitter 108 may be incorporated into a wristband, ankle band, or any other like device. It is foreseeable that RF transmitter 108 may be semi-permanently or permanently attached to a user's person in any manner. Electronic switchboard device 105 regulates calls and connects them to the proper outgoing trunk line 111. Trunk line 111 may consist of a multitude of connections to any number of local, long distance, or international telephone service providers. The number of trunk lines 111 depends on the outgoing capacity desired by the institution. In addition, trunk lines 111 may be analog, digital, or any other type of trunk lines not yet contemplated. Electronic switchboard device 105 further incorporates an integrated channel bank, allowing calls to be processed over either analog or digital trunks as required by the call management system 101. Specifically, when one trunk line 111 is occupied and handling an outgoing communication, electronic switchboard device 105 automatically accesses an alternate trunk line the handle the outgoing communication. If all trunk lines on the system are in use, the call may be routed to an alternate system (not depicted). For example, electronic switchboard device 105 may be interconnected to a multitude of switchboards to allow for expansion of the system to meet the capacity desired by the institution. A cross point switch integrated into electronic switchboard device 105 may also accomplish this routing.

Multiple processors may also be incorporated into the architecture. This allows call processing even after parallel component failure. The architecture also provides for a sharing of the load between processors, which eliminates system overload during extremely busy periods. The multiple processors enable the system to handle large volumes of calls at any time, and to ensure system integration.

Additionally, electronic switchboard device 105 performs the voice prompts heard by the inmate and the recipient of the call allowing the parties to respond to the menu selections. For example, before each telephone call is placed, preferably, the user of the system is required to provide a personal identification number (PIN) and a speech sample used to verify the identity of the user. Electronic switchboard device 105 prompts the user to provide these identifications and receives the responses (DTMF, and spoken) from the user. Electronic switchboard device 105 tests outgoing trunk lines as calls are placed and digitizes telephone audio for recording and/or biometric voice identification purposes. If no dial tone is present, one of trunk lines 111 may be taken out of service for a pre-programmed amount of time for maintenance. These capabilities are pre-programmed into the device's firmware. However, it is foreseeable that software and software upgrades may provide these services in addition to other services useful in the present invention.

A central site server 113 interfaces within the telephone call system 101 via a first serial port 115. In the preferred embodiment of the present invention, an RS-232 serial port is employed for the interference connection. However, it is foreseeable that other types of serial ports 115 commonly known in the art may be utilized. Serial port 115 may also be comprised of a direct hardware connection or may consist of a series of ports and connecting means commonly known in the art for connecting electronic devices. Serial port 115 is designed to allow firmware driven systems, such as electronic switchboard device 105, to interface with software-based systems, such as a PC designed system operating as a site server. All inmate and call information is routed through central site server 113. At central site server 113, user call information is digitized for efficient data transfer and efficient record keeping. Central site server 113 stores at least each user's financial transaction data. It is preferred that central site server 113 also stores the digitized audio used for voice prompts as well as each user's call restrictions, PIN, biometric verification data, etc. However, depending on the memory requirements, numerous site servers may be employed. It is foreseeable that older archived data may also be stored on an integral or a remote computer system database (not shown) or kept on additional storage devices on the central site server 113. Preferably, the voiced data, PIN, etc., are stored in a database on the central server 113. The database may be any commercially available database such as Microsoft Access, Microsoft SQL server, an Oracle database, an IBM database, etc.

Connected to central site server 113 via one of serial ports 115 is audio recorder 117. In the preferred embodiment of the present invention, an RS-232 serial port is employed for the interference connection. However, it is foreseeable that other types of serial ports 115 commonly known in the art may be utilized. Serial port 115 may also be comprised of a direct hardware connection or may consist of a series of ports and connecting means commonly known in the art for connecting electronic devices. Audio recorder 117 may either be a stand-alone unit or incorporated into the hardware of central site server 113, or incorporated into other hardware devices within the system. Although it is preferred in the present embodiment that audio recorder 117 is digital, it is foreseeable that other known types of recording devices, as well as those not yet contemplated, may be employed in accordance with the teachings of the present invention. Audio recorder 117 records the conversations performed under the direction of telephone call management system 101. Audio recorder 117 may be activated for each call unless the number being called is specifically flagged for no recording or monitoring, such as calls to or from an attorney. Furthermore, audio recorder 117 can monitor multiple telephone lines simultaneously, using a different recorder channel number for each of trunk lines 111. The recorder channel number further enables the institution's staff to identify the call record they wish to review associated with a desired outgoing telephone call. Each user telephone 102 is further associated with a station identification number which allows the staff of the institution to identify the particular user telephone 102 a call was initiated and conducted from. It is foreseeable that the embodiment described herein supports up to 32 inmate telephone stations 103 and 24 trunk lines 111. However, multiple units 105 may be configured to expand the system to meet the capacity demand for the institution. Audio recorder 117 is also used to receive voice samples from the users for identification and authorization purposes. Specifically, when an inmate first "subscribes" he or she must state his or her name. Voice recognitions software stored on central site server 113 verifies that the user spoke his or her name. Alternatively, central site server 113 may be equipped with specialized hardware for receiving and identifying voice samples. Voice identification solutions are known in the art and available from companies such as Nuance, Buytel, Veritel, Integrated Wave Technologies, Intervoice Brite, etc.

Central site server 113 is controlled by software associated with administrative workstation 120. In the preferred embodiment, administrative workstation 120 is connected to central site server 113 via a local area network (LAN). However, it is foreseeable that other types of electronic connections may be employed. The administrative workstation's 120 software can modify call restrictions for individual users in addition to all telecommunication activity of the institution. Additionally, the software can also track a user's commissary information, such as the account balance if a debit system is being used. Furthermore, depending on the needs of an institution, the database may perform other functions.

Commissary workstation 121 is used in conjunction with administrative workstation 120 to manage and record a user's financial transactions. In the preferred embodiment; commissary workstation 121 and administrative workstation 120 are connected to central site server 113 via a LAN. However, other known connections, or connections not yet contemplated may be utilized. Commissary workstation 121 can also record other financial information, such as the total amount spent on collect calls by each inmate, amount spent on debit calls, the total net financial transactions for each user, etc.

Shadow workstation 123 and investigative workstation 125 are also employed in the present embodiment. Shadow workstation 123 and investigative workstation 125 are connected via the local area network linked to central site server 113 in the present embodiment. Shadow workstation 123 utilizes a live operator to monitor telephone calls without detection. It is foreseeable that this function may be performed by software integrated with shadow workstation 123. The shadow workstation 123 software provides a means for patching into a call using circuitry without alerting the user or called party to the operator's presence. If the operator finds that a call being monitored is suspicious, the operator may manually (or by using software) activate the audio recorder 117 to record a portion of an active telephone call. The called party's number may also be flagged in the inmate's profile (stored on administrative workstation 120 or central site server 113) to provide future monitoring of calls from the specific user to the specific called party.

Alternatively, software located on central site server 113 or investigative workstation 125 may be used to passively monitor calls. For example, when certain key words or phrases are spoken, voice recognition software may activate audio recorder 117 via electronic means and alert the proper authorities that a violation has occurred. The same voice recognition solution that is utilized in verifying a user's speech sample (i.e., that a user provides his or her name when subscribing to the system) may be used to identify such key words and phrases.

Furthermore, investigative workstation 125 controls other monitoring and security features interfaced in call system. For example, investigative workstation 125 can be to access past conversations stored on audio recorder 117. Software on investigative workstation 125 may also be configured to detect if a third party is present during a user's conversation. Investigative workstation 125 or central site server 113 may also contain voice recognition software to aid in calling or called party voice authentication. Administrative workstation 120, shadow workstation 123, investigative workstation 125, and commissary workstation 121 may alternatively be combined into one or several units. Furthermore, administrative workstation 120, shadow workstation 123, investigative workstation 125, and commissary workstation 121 may be integral within the central site server. It is also foreseeable that any component may be alternately located off site from the other apparati of the present invention.

Figure 2A:
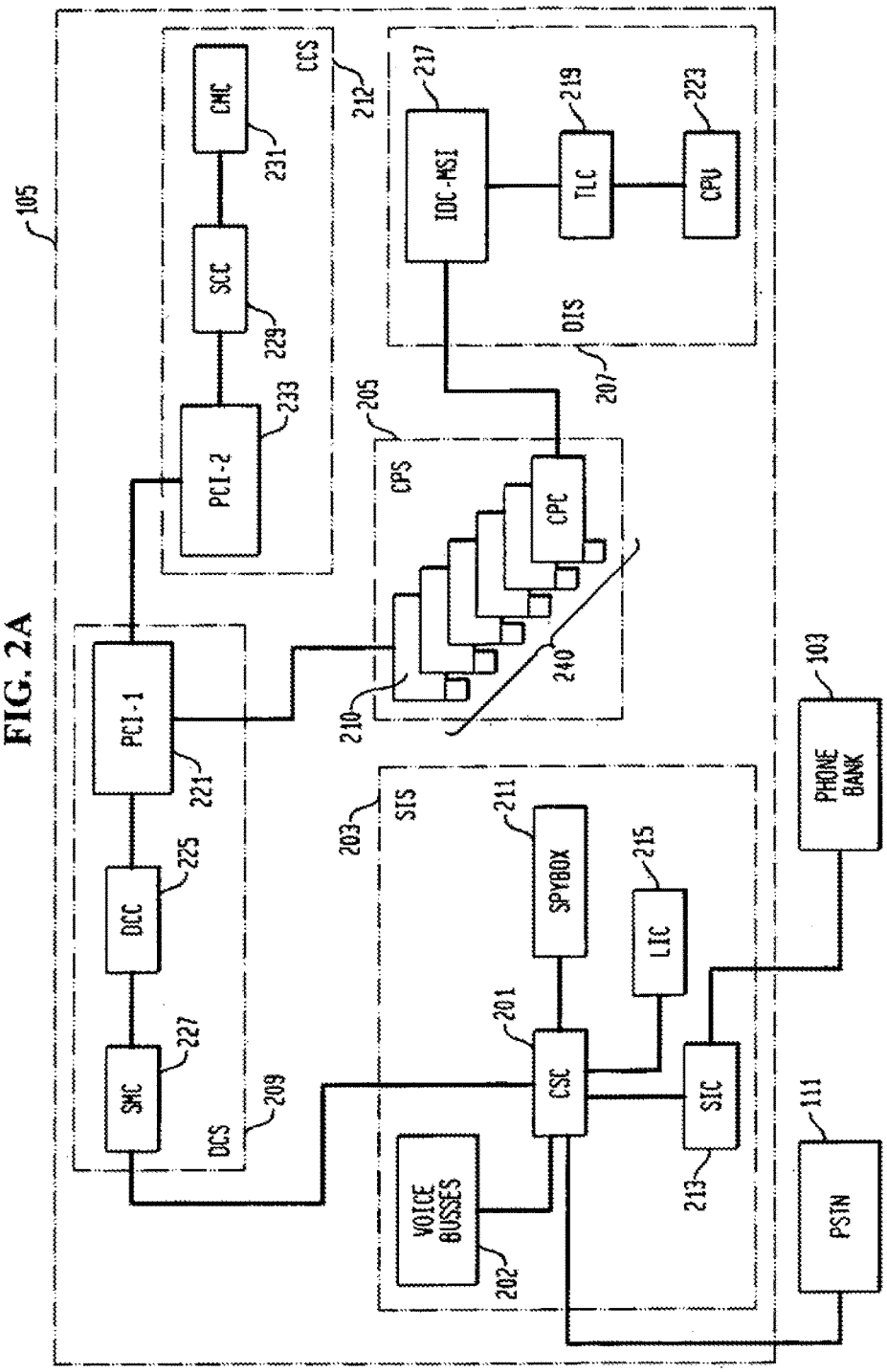
FIG. 2A depicts a schematic representation of the call management system's hardware, specifically directed to the central electronic switchboard device wherein a single electronic switchboard device is utilized.

Referring next to FIG. 2A, shown is an internal hardware diagram of electronic switchboard device 105 of the preferred embodiment of the telephone call management system depicted in FIG. 1. Stations equipped by electronic switchboard device 105 can access all trunk lines 111 accessed by electronic switchboard device 105 through a public switched telephone network (PSTN). Connections between trunk lines 111 and electronic switchboard 105 are supported by cross-point-switch matrix card (CSC) 201 in each unit and a set of associated unit-to-unit voice busses 202.

In the present embodiment of the call system, a series of bilingual voice prompts are provided. These voice prompts guide the user through placing a call through the telephone call management system. Pre-recorded voice prompts instruct the user how to place the call and announce the call to the called party, providing identification of caller and location of call. These voice prompts may be digitally produced and presented in a concatenated form as is presently known in the art or other common form in the art. The voice prompts may be pre-recorded by the institution and retained in an integrated or remote database, or may be recorded in any form as is known in the art. Furthermore, these voice prompts can be played in the language specified by the user's profile, the language specified by the institution, or in a multitude of languages.

Figure 2B:
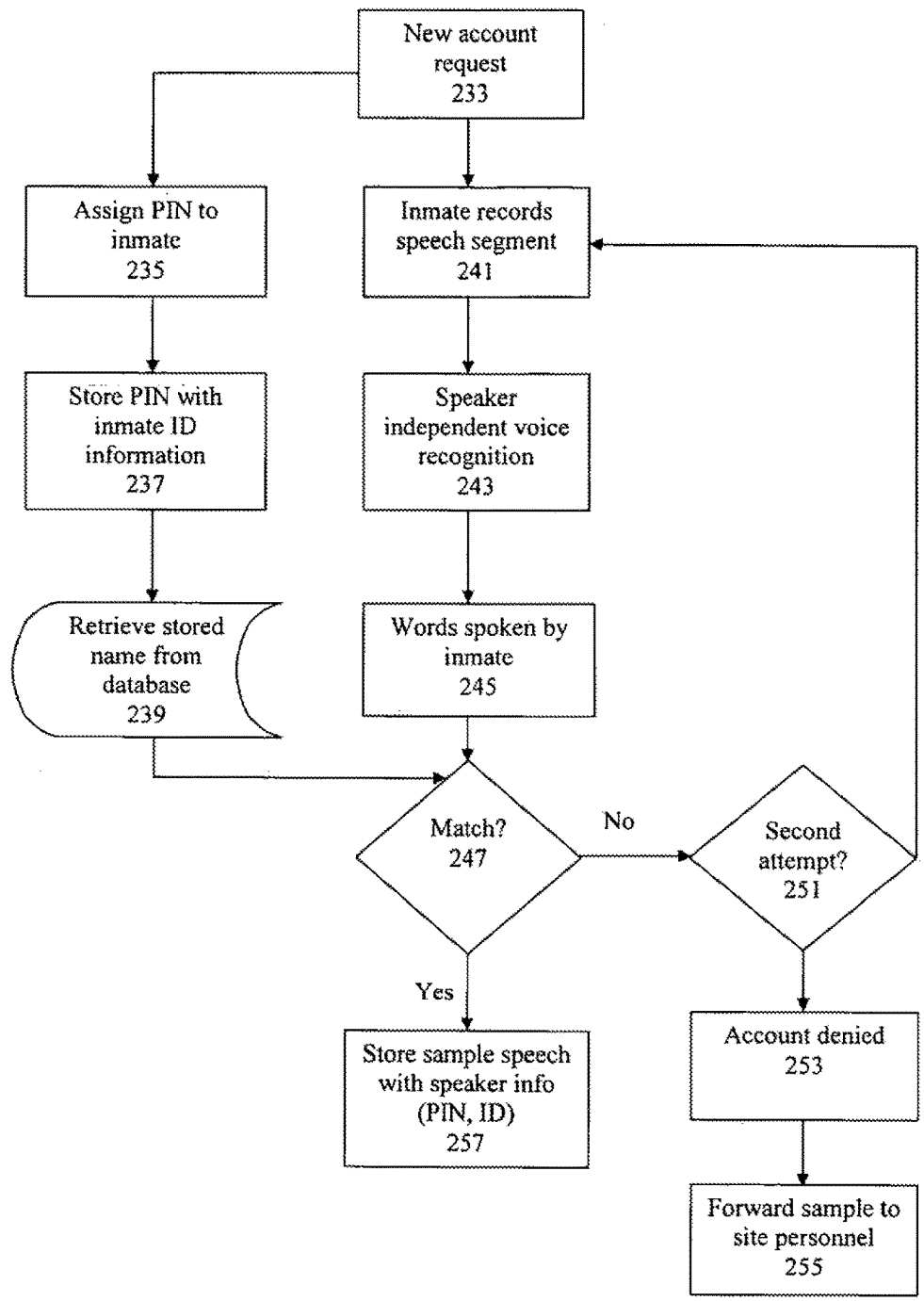
FIG. 2B is a flow diagram showing the process by which an inmate first enters the system and records a speech segment representing the inmate's name.
Figure 2C:
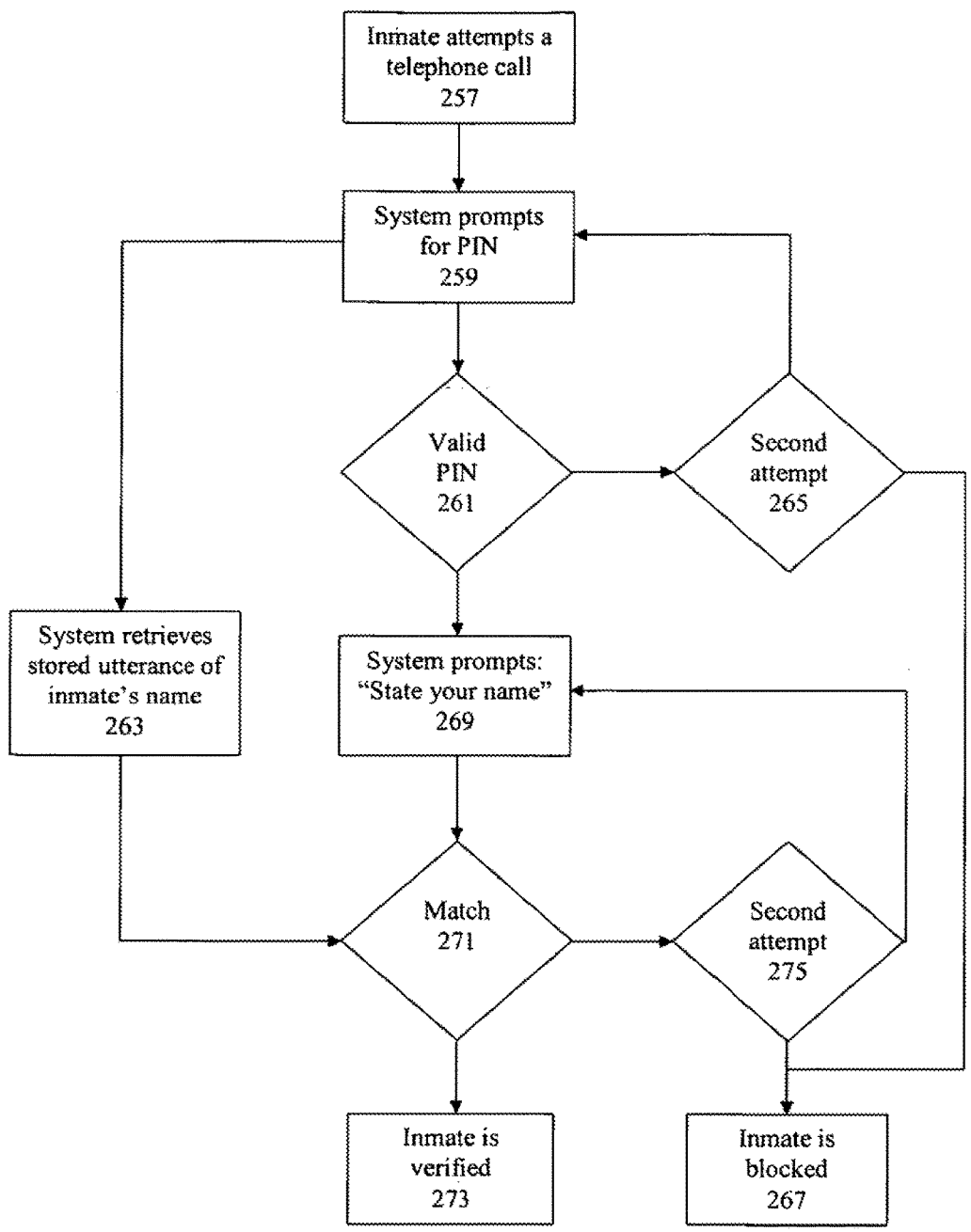
FIG. 2C is a flow diagram showing the process utilized by the system according to the present invention to identify and verify an inmate attempting to place a telephone call, where the system prompts the inmate for a PIN and a sample of the inmate's speech.

FIGS. 2A and 2B are flow diagrams that show the prompts provided to a user to enable the user to subscribe to the system (FIG. 2B) and to prompt the user for identification information before any telephone call is placed (FIG. 2C). Referring first to FIG. 2B, depicted is a flow diagram showing the process by which an inmate first enters the system and records a speech segment representing the inmate's name. When a new inmate is to be entered into the system (step 233), the system assigns a personal identification number (PIN) to the inmate (step 235). This PIN is stored with other inmate identification information such as the inmate's name, the inmate's cell location, the inmate's address, the inmate's social security number, etc. (step 237). This information is stored in a database or equivalent for subsequent retrieval (step 239). Although the database can be located at any point in the system, in the preferred embodiment, the database is stored on central site server 113.

When a new inmate is entered into the system, in addition to assigning a PIN and storing identification information for the inmate, the system also stores a sample of the inmate's speech (step 241). In the preferred embodiment of the present invention, this sample speech should be the inmate stating his or her name. Although other speech segments can be recorded, it is important to require the inmate to record a sample of speech that is not easily repeated. Preferably, audio recorder 117 is utilized to record the utterance of speech avoiding the need for any additional hardware to incorporate voice recognition as part of the system of the present invention. The recording can then be stored with the database in any standard recording format (.wav, .mp3, .wma, etc.).

It is known in the art to utilize speaker dependent voice recognition algorithms, software, hardware, programs, etc. to identify a speaker. However, it is also known in the art that such systems can easily be defeated if the sample of speech can easily be mimicked. For example, a speaker identification program may fail to distinguish a speaker if the sample of speech is simply a whistle or a blow into a microphone. Therefore, the system of the present invention preferably ensures that when the inmate is prompted to record a speech segment (step 241), that the inmate speaks his name.

The system of the present invention utilizes speaker independent voice recognition software to automatically ensure that the inmate has provided a valid speech segment (i.e., his or her name) (step 243). As is known in the art, speaker independent voice recognition software is now commonly available as off-the-shelf software for computers that utilize standard operating systems (e.g., Windows, UNIX, Macintosh, etc.). This software includes voice recognition software modules that can easily be integrated into existing system software. Therefore, the voice recognition software can be readily installed on central site server 113 and can be incorporated into the system of the present invention. Of course, alternative speaker independent voice recognitions solutions (e.g., hardware solutions such as integrated circuits (Ies) or digital signal processors (DSPs)) can be utilized without departing from the spirit of the present invention.

Regardless of the specific implementation, the speaker independent voice recognition module receives the speech segment spoken by the inmate (and captured by audio recorder 117) (step 243) and outputs data representative of the words spoken by the inmate (step 245). The words spoken by the inmate are compared with the stored identification data to verify that the speaker indeed spoke his or her name (step 247). If the speaker did not state his or her name, the inmate may be given a second attempt (step 251). If it is already the inmate's second attempt, an account for that inmate can be denied (step 253), and the sample speech spoken by the inmate can be forwarded to site personnel for manual analysis (step 255).

If, however, the inmate speaks his or her name, as verified by the speaker independent voice recognition module, then the sample speech is stored in the database with the inmate's other information (PIN, identification number, cell location, etc.) (step 257). The initial subscription of a user may also include receipt of biometric information (e.g., thumbprint, retinal scan etc.) to be retained by the call system for future authorization (not shown in FIG. 2B).

After a user provides the necessary verification information, a user profile can be established including restricted call number, amount stored in a debit account, call time restrictions, and other such information. The user profile may contain lists of valid telephone services and types of screening used for that specific user. The information may be displayed to a user via an associated display means, may be electronically provided via a verbal call prompt or may be hidden from the user.

Turning next to FIG. 2C, depicted is the flow of prompts and caller responses to validate a user each time the user wishes to operate the telephone call management system and place a telephone call (step 257). Initially, the system prompts the user to enter a PIN (step 259). As described with respect to FIG. 2B, each user is assigned a unique PIN when subscribed to the system. Generally, the user can provide the PIN using DTMF tones (i.e., pressing numbers on the telephone keypad) or by speaking the numbers or letters that comprise the PIN. The system verifies the PIN as a valid PIN (step 261) and retrieves the corresponding identification information for the user (step 263). If the PIN is not valid, the system may give the user a second attempt to enter a valid PIN (step 265). Any subsequent attempts may be denied (step 267).

If a valid PIN is entered, the system next prompts the user to state his or her name (step 269). The user's spoken sample is received and compared with the stored utterance of the inmate's name (step 271). If the two samples match (i.e., the speaker dependent voice identification solution utilized by the present invention determines the samples were provided by the same person), the inmate is verified (step 273). If there is no match, the user may be provided with a second attempt (step 275). Any subsequent attempts may be blocked (step 267). However, if a user is verified (step 273) the user will be able to use the telephone management system of the present invention in accordance with the user's designated rights and restrictions.

Referring back to FIG. 2A, the user's transmission receipt paths can be controlled during the call processing, thus providing control of the user's communications with interactive call progress prompts and responses, network call progress information and tones and the called party during call announcement and acceptance. For example, after the call is outpulsed to the public switched telephone network (PSTN), the user can listen to normal network provided tones, announcements, call answer, and caller acceptance. However, verbal transmissions from the calling party may only be heard by the called party.

Multiple trunk lines 111 are supported by electronic switchboard device 105. In addition, different routing to the PSTN may be assigned across multiple trunk groups. Use of multiple trunk groups may be required or preferred due to lower network access charges, routing facilities and usage costs, (i.e. local, international, long distance debit, long distance collect, etc.).

In addition, electronic switchboard device 105 can provide digit analysis based on dialed number identification system ("DNIS"), other dialed digits, etc., and can route a call via the appropriate trunk lines 111. Trunk lines 111 may interface the network on direct digital T1 circuits, analog circuits, or other like network interfaces.

The distributed architecture of the hardware and associated software of the electronic switchboard device 105 comprises Station Interface Subsystem (SIS) 203, Call Processing Subsystem (CPS) 205, Digital Interface Subsystem (DIS) 207, Data Communication Subsystem (DCS) 209, and Concentrator Communication Subsystem (CCS) 212.

Station interface subsystem (SIS) 203 provides switched connections to call processing subsystem (CPS) 205. CPS 205 controls digit collection, interactive voice prompts, call screening, network access, etc., during the inmate calling process. Specifically, during the call routing process, if trunk lines 111 in the primary trunk group are all occupied, a variation of call treatments may be implemented. For example, the call may be routed to a secondary trunk group, a voice message may be played, a congestion busy signal may be provided, etc.

In the preferred embodiment, SIS 203 contains four main components including SIC (Station Interface Card) 203 which provides power to all telephones, CSC (Cross-Point Switch) 201 which routes telephone calls from telephone bank 203 to the proper outgoing trunk line 111, LIC (Line Interface Card) 215 which converts analog telephone signals to a format compatible with the call management system, and Spybox 211 which is used for audio monitoring of user telephone calls. The basic function of SIS 203 is to detect and process off/on-hook call service requests from the telephones located at inmate telephone bank 103. SIS 203 also CO1U1 ects the line to an available call processor card (CPC) 210 port for processing the inmate call. In addition, SIS 203 provides switched audio connections to Spybox 211.

The originating user off-hook requires connecting station interface card (SIC) 213 voice paths via cross-point switch card (CSC) 201 to line interface card (LIC) 215. Voice path connections are switched and controlled by CSC 201. The selected LIC 215 outbound port connects the line to CPC port 210 for processing the call. Dial tone is provided to the inmate when CPC 210 is connected and ready for the inmate to enter digits.

Call processing system (CPS) 205 controls all routing and subsystem, interaction processes required by the call management system. CPS 205 contains one or more call processing cards (CPCs) 210 which provide voice prompts to users and receives and record DTMF and voice responses. Thus, CPS 205 is used extensively during the initial login wherein a potential user provides a PIN and a speech sample. Specifically, CPS 205 (specifically CPCs 210) provide prompts instructing the user to provide a PIN, and if the PIN is indicative of an authorized user, a speech sample for voice verification. CPS 205 then receives a user's response to the prompt for a PIN (preferably in the form of DTMF tones), and the user's spoken response to the prompt for a speech sample.

Station voice paths switched through the SIS subsystem 203 are connected to call processing card (CPC) 210. In the present embodiment, CPCs 210 have four ports per card. However, additional ports per card may be utilized in accordance with the objectives of the present invention. For example, in the preferred embodiment, call processing subsystem (CPS) 205 can accommodate up to six CPCs per call system unit allowing each electronic switchboard device to support up to twenty-four call processing ports.

CPS 205 can accommodate multiple CPCs 210 which allows system redundancy and system availability. Real-time call processing loads are distributed across the number of configured CPCs 210. In the preferred embodiment, the subsystem is configured with a minimum of two CPCs 210 per electronic switchboard device. For example, it is preferred that a minimum of two CPCs 210 are utilized as a fault protection. If one CPC fails, call processing would continue on the other active CPCs 210.

Call processing cards (CPCs) 210 support the specialized call processing features and controls required for an institution telephone service. When a user originated call is connected to CPC 210, a dial tone is returned to the user. The dial tone indicates that the call system is ready for the caller to enter digits. During the call process, CPC 210 interacts between other subsystems and the call, thereby supporting the necessary system call sequence control and prompts for completing the call.

CPCs 210 collect dial tone multi-frequency (DTMF) digit information, or like information, entered by the user and provides pre-recorded voice prompts stored in system memory card (SMC) 227 delivered to the user via an audio record/playback buss. CPCs 210 connect the audio/record playback to the user telephone. Interactive voice prompts instruct the user to enter a series of identification and/or authentication information. For example, a user may be required to provide voice information for authentication or recording, DTMF information responses such as a PIN, biometric information for authentication, or provide RF data. Prompt responses are detected and recorded via CPCs 210. Biometric responses are recorded via separate hardware in the call system using a voice buss that couples to the DIS. Voice responses are played on the audio record/playback buss to SMC 227 for processing. Processed voice signals are digitized and stored in memory (not shown). Once the originating call is processed and approved, CPC 210 will either connect the call to its associated network trunk lines 111 and outpulse the call or otherwise be released from the call so that the call can be connected by SIS 203 to an alternate CPC 210 for outpulsing the call. If the user's call is not approved (e.g., if the user's speech does not match the stored speech sample provided by the user during the user's initial subscription to the system), a special call treatment is returned to the user. Special call treatments can comprise voice prompts, busy signals, etc. For example, these special call treatments generally provide information concerning why the call could not be completed and processed.

When the call is outpulsed and answered, CPC 210 provides called party prompts to announce the call, which may include asking the calling and called party for voice verification. The called party may also have to enter a PIN to be authenticated. The system of the present invention supports subscribing called parties. When a potential called party subscribes to the system a similar process is used as when a user subscribes (see FIG. 2B), and a similar process can be used to verify the identity of the called party (see FIG. 2C). Call connections are monitored by the CPC 210 for the duration of the call. This allows CPC 210 to detect answer, call acceptance, switch-hook flashes, disconnect and provide other supervisory signals. SMDR data (or other like call record information) is collected by CPC 210 and buffered in SMC 227.

The CPC hardware is laid out on a PC board design that supports two plug-in daughter boards. The main PC board is identified as the line card. The larger daughter board is identified as the line card extension board. The smaller board of the two is identified as the CLICK board.

Digital interface subsystem (DIS) 207 converts analog voice information to a digital format. Integrated analog/digital conversion card (IDC-MSI) 217 handles analog to digital (A/D) conversion for the telephone call management system. Digital T1 interface card TLC 219 routes calls to CPU 223. CPU 223 contains software which controls user access to the telephone call management system. CPU 223 can also store all financial and authentication data. Furthermore, CPU can be capable of processing any other data as may be required within the system.

Digital interface subsystem (DIS) 207 provides an integrated digital T1 network interface capability for the call system. DIS 207 interfaces call processing system (CPS)

205 lines/trunk ports. DIS 207 formats the digital voice signals into a 24 channel digital T1 interface. In addition, DIS 207 processes user inquiries and performs account update transactions via the LAN. DIS 207 can include an integrated analog/digital conversion card (IDC-MSI) 217, digital T1 interface card (TLC) 219, PCM extension buss (PEB) 221, and a digital subsystem CPU controller card (CPU) 223.

The integrated analog/digital conversion card (IDC-MSI) 217 is a commercial design commonly employed in the art. The design is a proven technology and is utilized in a large number of switching applications.

This design is based on a Dialogic® modular station interface (MSI) board or other similarly designed boards. A PC-AT form factor board was developed by Dialogic® to support integrated digital switching functions. The board is compatible with PCM extension buss (PEB) 221 based designs. Furthermore, the board is compatible with the North American (1.544 Mb/s transmission rate, u-law PCM coding) and European (2.048 Mb/s transmission rate, A-law PCM coding) digital interface standards.

The Dialogic® MSI board consists of a motherboard that can accommodate up to six base modules or two add-on modules. The six-module version supports four analog port interfaces per module. The two add-on module version supports twelve analog port interfaces per module. Each version fully configured supports up to 24 inbound analog ports. These analog ports are connected to distribution blocks for grading to the CPC's line-side interface ports. The CPC and IDC blocks are used for cross-connection the CPC ports 240 to the IDC ports.

Data Communication Subsystem (DCS) 209 controls data communications between multiple call management systems. DCS 209 contains data communication card (DCC) 225, system memory card (SMC) 227, and PC Interconnect Card (PCI-1) 221.

Multiple unit systems require communications between units. This is supported by equipping one of the units with a communications concentrator subsystem (CCS) 212. CCS 212 contains system concentrator communication card (SCC) 229, concentrator memory card (CMC) 231, and a second PC interconnect card (PCI-2) 233.

Completed calls to trunk lines 111 require that caller identification and instructions be provided to the called party. A variety of programmed voice prompts can be used to announce the call and to instruct the called party. Typical voice prompts include information regarding where the call originated from, the type of call (i.e., collect/prepaid), how to accept or decline the call, how to deny future calls from the same caller, etc. For example, if the user (John Doe) places a collect call, the message "You have a collect call from John Doe. Dial -55- to accept the call or hang-up to decline the call," may be played. If the called party enters positive acceptance, the caller is provided a transmission path.

Throughout the duration of the call, the system monitors the called party line for switch hook flashes. Detection of these flashes may indicate potential three-way calling/conference feature activation by the called party. If a hook flash is detected, the system may be programmed to limit the call to a certain time duration, and/or to play a warning tone or play an announcement to both parties thirty seconds prior to disconnect.

In addition, design features prevent the user from reaching live operators or the ability to chain dial. Each call process requires that a specific disconnect duration to the network is completed. New call attempts are forced through a rigid call state sequence and screening, which includes a number of authentication means such as a PIN, biometric information, and/or RF authentication.

A number of features are provided to aid in call screening. Each user profile may contain a list of telephone numbers to which calls may be placed. Certain exchanges or prefixes, such as 1-800, may also be blocked. Other options, such as the number of calls allowed, call minutes allowed, or restriction to specific forms of call payment may be specified.

Concentration communication subsystem (CCS) 212 is responsible for supporting communications between the call system units and to the servers. CCS 212 includes a system concentrator communication card (SCC) 229, a concentrator memory card (CMC) 231, and a second PC interconnect card (PCI-2) 233.

CCS 211 is configured using the same basic hardware cards as utilized in the data communication card system. However, each memory card is independent and operates under different software systems.

Call detail records (CDRs) collected in the CPCs 210 are typically communicated to DCS 209 over the CPC COM port disposed within call processing system (CPS) 205. The CDRs are then buffered in SMC 227. The CDRs may also be transmitted to CCS 212 and buffered in CMC 231. CMC 231 may act as an interim backup for the CDR records. When requested, the buffered CDR's are also transmitted via CCS 212 to the server(s).

Each CDR transmitted and acknowledged by the server is flagged by the memory cards. Servers use a polling method during low traffic periods to upload CDRs from the memory cards. During the next polling sequence, only the CDRs that have not been acknowledged are transmitted to update the server CDR database. Basically, CDRs may at one point be buffered in a DCS memory card (SMC 227), a CCS memory card (CMC 227), or a server database (located in central site server (113 from FIG. 1). This capability enhances CDR reliability and recovery.

Figure 3:
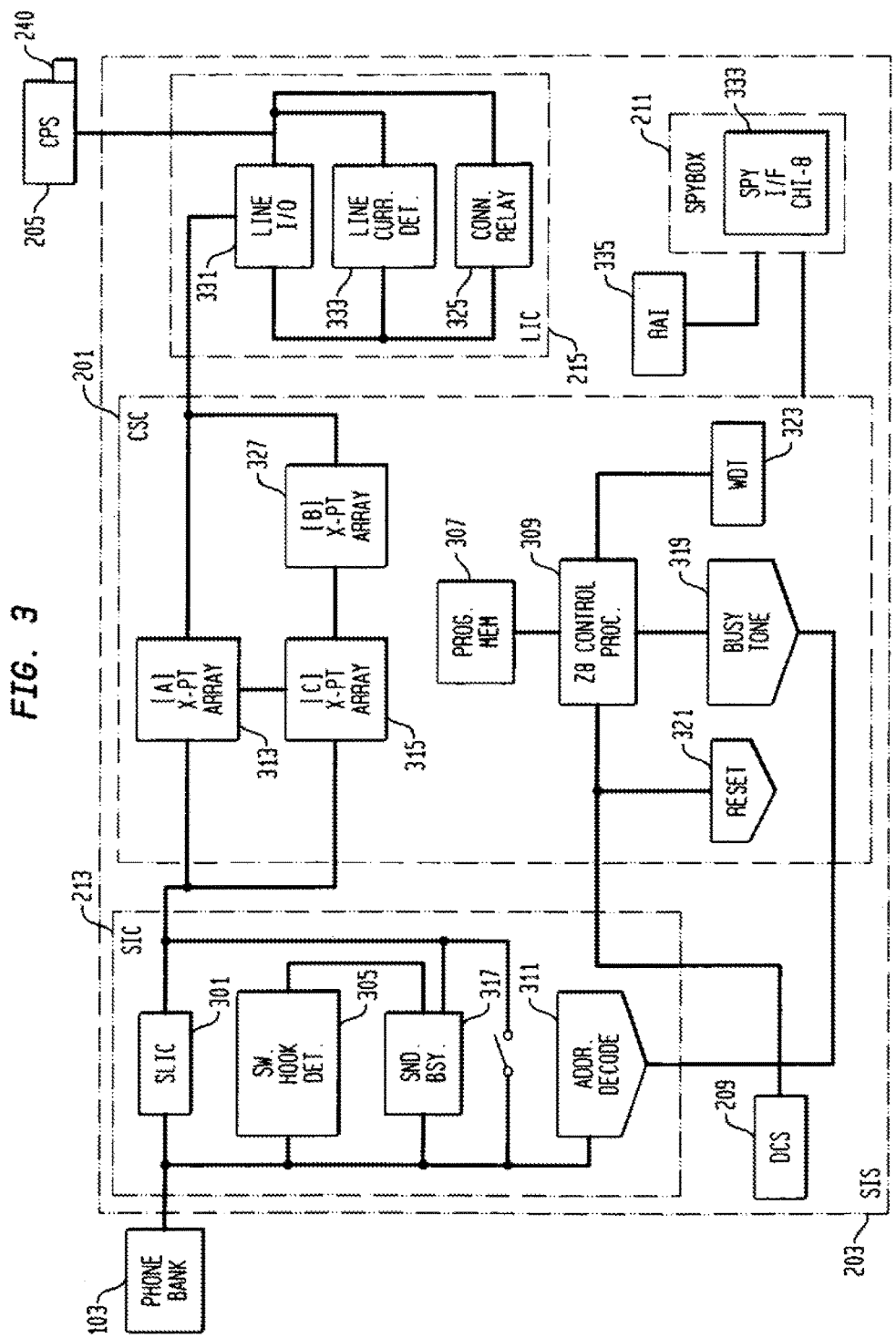
FIG. 3 depicts a detailed schematic representation of the Station Interface Subsystem (SIS) of FIG. 2A.

Referring next to FIG. 3, shown are station interface card (SIS) 203 and its four main components, namely station interface card (SIC) 213, cross-point switch card (CSC) 201, line interface card (LIC) 215, and spy remote audio interface module (RAI) 335. As described above in FIG. 2A, SIS 203 is integrated within electronic-switchboard device 105 and provides a connection point between telephone bank 103 and Data Communication Subsystem 209. Generally, SIS 203 detects the on-hook status of user telephones and provides the appropriate response signal (e.g., dial tone, busy signal, etc.).

As shown in FIG. 3, the first main component of SIS 203 is station interface card (SIC) 213. In the present invention, each user telephone in telephone bank 103 is connected to the system via a two wire (tip/ring) cable pair used for each communication line. These lines are connected to individual subscriber line interface circuits (SLICs) 301 on SIC 213. In this embodiment, SIC 213 supports 32 SLICs 301 per SIC 213. One SIC 213 is equipped per electronic switchboard device configured in the call processing system.

SIC 213 has subscriber line interface circuits 301 to connect and provide power to user telephones 103. Individual switch-hook detect circuits 305 monitor the telephone lines for on/off-hook states. Generally, the normal line state is either idle or on-hook. However, detection of an off-hook state represents a new call service request.

SIC 213 converts the 32 balanced 600 ohm two wire line circuits into 32 individual single wire two-way voice busses. The 32 voice busses connect to [A] point array 313 and [C]

X-point array 315 on CSC 201. Busses then may be connected via CSC 201 to idle CPC ports 240 for call processing. When a valid connection is established, the CPC returns a dial tone to telephones located within user telephone bank 103.

Calls originating from SIC 213 that cannot be connected to idle paths generate a busy tone from generator 317. CSC Z8 control processor 309 selects the send busy circuit in the SIC 317 (via circuitry not depicted). SIC 213 connects the busy tone signal 319 to a telephone in phone bank 103. When the telephone disconnects, the circuit is released and the telephone is ready for a new call origination.

CSC Z8 control processor 309 on CSC 201 continuously queries switch hook memory detect circuit 305 to detect new off-hook service requests. When a permanent off-hook or an invalid connection is detected, CSC Z8 control processor 309 enables send busy signal 317. This places the station line in a permanent or lockout busy state. The condition may be cleared when the telephone or faulty off-hook status is restored. When a condition is restored, the station line can originate new calls.

The second main component of SIS 203 is cross-point switch card (CSC) 201, which provides a 32 by 24 cross point switching matrix for connecting stations to call processors and network trunks. In addition, it also performs switch connections for Spybox 211 monitor access.

CSC 201 supports an automatic reroute feature. Connections to CPC ports 240 during the call process may be switched to a second CPC port. This reroute may be required to access an idle trunk for a different call type route. This feature allows call connections to be rerouted in the system to pre-designated call treatment types or alternate trunks.

Upon initialization, CSC Z8 control processor 309 reads and loads programs from onboard E-PROM based program memory 307. During initialization, CSC Z8 control processor 309 performs subsystem reset 321. At this point, CSC Z8 control processor 309 performs hardware diagnostics and data validation. Configuration control information is sent to the Data Communication Subsystem (DCS) 209 concerning the in-service station location addresses which are mapped into program memory 307. Under control of CSC Z8 control processor 309, address decoders decode the on/off states. The CSC 201 decodes the addresses to select [A] X-Point array 313 or [C] X-Point array 315X-Address location for that individual station.

During operation, onboard watch dog time (WDT) 323 monitors the processor operation and sanity. WDT 323 will automatically reset the hardware if any abnormal condition would prevent the recovery of CSC Z8 control processor 309. Reset 321 then causes the subsystem to re-initialize and return to a normal in-service state. In the case of an invalid on/off hook state or connection, CSC Z8 control processor 309 reset logic can restore the call connection to an idle state, set busy connect for permanent off-hook stations, or reset LIC connect relay 325. LIC connect relay 325 may be enabled or reset under control of the CSC Z8 central processor 309 to connect or release the CPC port. Release of the CPC port will disconnect the forward connection to the network.

In the present embodiment, concentration may be introduced by CSC 201 between its 32 station ports and 24 LIC ports. The level of concentration per unit, provided all 32 stations and 24 trunks are assigned, is 32:24. This would limit the number of simultaneous calls per unit to 24. Concentration levels may be varied by the assignment of stations and trunk lines across the equipped unit. For example, these levels can be 1:1 for a non-concentrated configuration. It is foreseeable that alternate concentration levels may be provided depending on the number of stations and trunk lines utilized in the telephone call management system.

Still referring to FIG. 3, [A] X-point array 313 provides a 32 by 24 matrix. This array cross connects the 32 SIC 213 voice busses to any of the 24 LIC 215 voice busses. The 24 LIC outbound circuits are connected to individual CPC ports 240 in the unit's call processing subsystem (CPS) 205.

When CSC Z8 central processor 309 detects a new call origination, the outbound 24 voice busses on [A] cross-point array 313 are selected first. The first choice routes are to the CPC ports 240 within the same unit. Secondary routes to CPC ports 240 in other companion units are connected through the [C] X-Point array 315.

[B] X-point array 327 provides a 16 by 24 matrix. Eight of the sixteen voice busses represent the inbound unit/unit OUT and unit/unit IN busses. These busses are used to switch station connections to and from other companion units. Outbound access to the busses is via [C] X-Point array 315. Unit/unit inbound access to the 24 LIC 215 voice busses is through [B] X-Point array 327.

The other eight busses are unit/unit IN busses, commonly referred to as half busses. These busses support inbound voice connections for Spybox 211 monitor connections. Monitor access is provided through [B] X-Point array 327, establishing the monitor connection on the trunk side of the call path. A set of dipswitches (16 switches) on CSC 201 provides the option to connect or disconnect the unit/unit voice busses.

The processor's serial COM port (located on the processor) provides data communications between CSC 201 and data communication subsystem (DCS) 209. COM port 329 supports inter-processor communications between units for call connections and unit/unit call control. In addition, in an offline mode, the port may be used to support external maintenance and debug access.

A third main component of SIS 203 is line interface card (LIC) 215, which interfaces SIS 203 to call processor subsystem (CPS) 205. LIC 215 converts the 24 outbound voice busses from CSC 201 to 24 (balanced 600 ohm) two-wire interface circuits. These circuits are connected to individual CPC ports 240. The CPC ports 240, under control of CSC Z8 control processor 309, provide access for call processing and network trunk lines.

Each of the 24 LIC inbound ports directly interface the voice buss from CSC 201. The audio path conversion includes a balanced 600/600 ohm transformer coupled circuit (not shown) and connect relay 325.

Connect relay 325 controls the seizure and the release of the associated CPC port 240. When the relay circuit is enabled, the LIC port extends an off-hook to CPC port 240. In a normal or release state LIC 215 extends on-hook status to CPC port 240. Control of the relay is performed by CSC Z8 control processor 309 address/data buss via I/O address decoder 331. A current detect circuit 333 output is read by CSC Z8 control processor 309. Current detect circuit 333 monitors the loop current in the connection to the CPC port. This permits CSC Z8 control processor 309 to detect the call path connect and disconnect status.

A coupled component of SIS 203 is Spybox card (SBC) 211, which supports non-intrusive access to monitor and record user calls. In the present embodiment, the eight SBC inbound ports interface to the CSC X-point single wire voice busses, which then convert the single wire technology to a balanced 600 ohm two-wire tip and ring voice circuit. The eight outbound two-wire ports connect to remote audio monitor devices. Monitor access in each unit is connected by X-point array [B] 327. Each monitor path is cross connected to one of the 24 inbound voice paths to the LIC.

Spy channel access is connected through the [B] X-Point array 327. The actual monitor connection is made at each unit's LIC inbound voice buss. Therefore, each monitor point connection is made at the trunk side of the telephone call.

The eight spy channel busses have access to a set of eight unit/unit voice busses. These unit/unit buss connections provide access to other companion units in the system. The unit/unit busses connect to the [B] X-pt array 327 in each equipped unit.

The CSC Z8 control processor 309 controls activation of a spy channel connection to an individual telephone call. A monitor request by a Spybox workstation routes a unique broadcast message to the call system units. The broadcast message is sent to each equipped CSC 201 via the COM port. CSC 201 (with the actual telephone call) acknowledges the broadcast message and then completes the monitor connection.

The eight inbound spy busses connect to line current detect circuit 333 on SBC 211. This interface circuit converts the voice buss into a 600/600 ohm balanced two-wire tip and ring line circuit. These line circuits from SBC 211 connect to Remote Audio Interface (RAI) circuit module 335. Each SBC line circuit to RAI 335 has a line current regulator and a line current detector circuit.

The line current regulator is enabled or disabled under control of CSC Z8 control processor 309. The line current regulator controls loop current to RAI 335 when the monitor connection is established. The line current detect circuit senses the loop current to RAI 335. Output of the detect circuit is addressed and read by CSC Z8 control processor 309. This allows the processor to determine the RAI module line connection state.

The final component of SIS 203 is spy remote audio interface module (RAI) 335, which is a single port audio monitoring module. Each RAI 335 uses line power from SBC 211 to detect an active monitor connection. An isolation transformer connects the inmate audio to the monitor OUT and speaker jack. RAI 335 can be placed at various monitor locations at the inmate facility. Each RAI 335 provides a control circuit for activating the recording device.

An isolation transformer provides a balanced 600 ohm tip and ring circuit to the device for recording the inmate conversations. A ⅛" speaker T, R, and S stereo jack located on the module may be used to support an external speaker connection.

Figure 4:
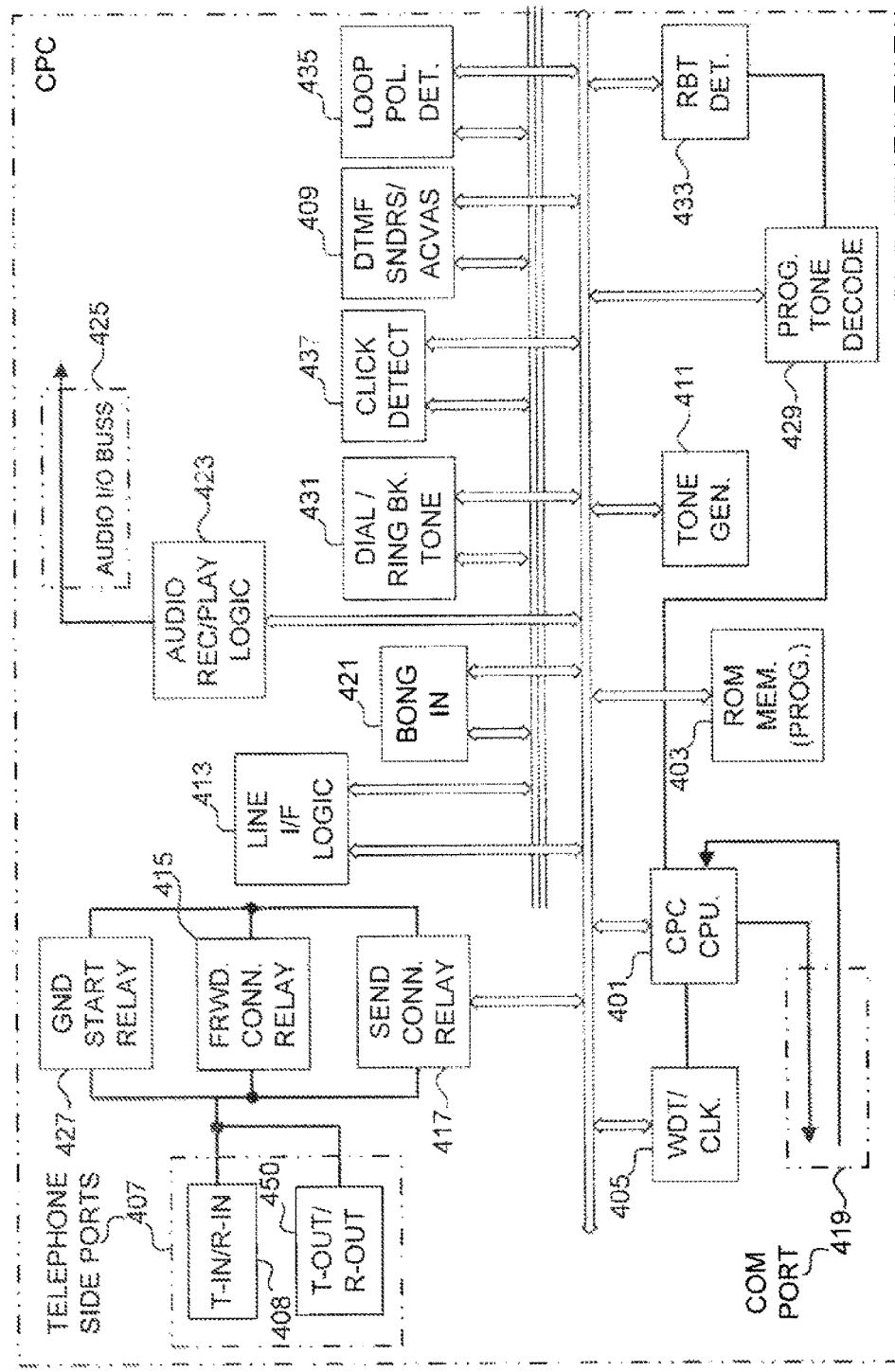
FIG. 4 depicts a detailed schematic representation of the call processing control card (CPC) of FIG. 2A.

Now referring to FIG. 4, shown is a schematic diagram of call processing card (CPC) 210. CPC 210 is an integral device located within the electronic switchboard device. However, CPC 210 may be located external to the electronic switchboard device while still performing the basic functions described herein. Call processing card processor 401 is initialized from E-PROM based program memory 403 when the system powers up. Onboard watch dog time (WDT) 405 monitors sanity of the processor. Call processing card processor 401 will automatically try to recover from abnormal hardware or software error conditions that affect processing. If this error state is persistent and call processing card processor 401 is unable to recover, onboard WDT 405 will automatically force reset call processing card processor 401. This will cause CPC 210 to reinitialize and return to service. The onboard RAM supports real time database access and is battery-backed for data integrity.

The LIC outbound ports connect to CPC telephone side ports 407. The telephone side port signal leads 450 are identified as T-out and R-out.

The LIC outbound ports extend a loop closure signal to the CPC 210. This initiates CPC 210 seizure and connects the station voice path. CPC 210 enables DTMF receivers 409 and returns a dial tone that confirms originating access. This signals the system is ready for the system user to press digits on the telephone keypad. In addition, onboard tone generator 411, which is under control of the call processing card processor 401, sends a dial tone to the station via the line interface logic.

CPC line interface logic design 413 includes both forward connect circuit (FCR) 415 and second connect circuit (SCR) 417. Processing a call requires the station and line side paths be independently controlled by call processing card control processor 401. This allows call processing card control processor 401 to control transmit and receive path information during the user call process.

After the initial seizure of CPC telephone side port 407, the station and line side are split via FCR 415. Enabled DTMF receivers 409 detect the information digits entered by the user. A typical dial plan allowed may include 1+10 digits for debit account type calls terminated to national numbers, 0+10 digits for collect type calls terminated to national numbers, or any other foreseeable combination of digits. Biometric and/or voice verification may occur either before or after DTMF tones have been entered.

Call processing card control processor 401 collects the digits entered by the user and routes the digits to a database capable of providing digit comparison. Digit analysis is performed to determine the call type (collect, debit, speed dial, national, international, etc.).

The call system may require users to enter a Personal Identification Number (PIN). Any range of digits may be used. However, to handle most institution requirements, the range of the PIN is one to nine digits or characters typically. Each number is unique to a user. The PIN may be used to index a discrete user file by the User Telephone Account Control (UTAC) server or an inmate telephone account control (ITAC). COM port 419 on CPC 210 supports communications with the server via data communication control card (DCC) (i.e., 225 of FIG. 2A.). The CPC subsystem design supports up to six COM ports, one for each CPC control processor 401.

Bong tone 421 is played to the user after the digits are entered. Bong tone 421 signals the user that the system is in the auto attendant mode. In the auto attendant mode, interactive voice prompts will interface to the user and guide the user through the calling process, possibly asking for biometric authentication, and providing a means to interface the user entered data to the call system.

Each CPC has audio record/playback logic 423 interfaced to four I/O busses 425. I/O busses 425 connect to the call system voice memory card (SMC) (i.e., 227 of FIG. 2A.). Preferably, each of the four I/O busses 425 is a single wire audio buss, although other configurations may be used. Each I/O buss 425 supports one of four CPC telephone side ports 407. Audio record/playback logic 423 under control of CPC—processor 401 permits individual record/playback on either audio I/O buss 425. Audio buss 425 can be enabled to play or record on either the station and/or the line side of the connection.

The telephone call management system of the preferred embodiment supports playing voice prompts that guide a user through the call process. Audio record/playback logic 425 supports recording of the user's name and the called party's name for later use in voice prompts and/or voice authentication functions. In addition, audio record/playback logic 425 supports playback of pre-recorded voice announcements to the called party when answered. Based on call type and the user data profile, different voice prompt menus may be selected according to the user's preferred language and other like options.

The interface logic's line side is open until CPC control processor 401 is ready to extend the call. Line side ports interface and connect toward the network. Port signal leads 408 are identified as T-in and R-in. Port signal leads 408 connect to either PSTN network analog trunk line 111 facilities or integrated analog/digital conversion card (IDC-MSI) (i.e., 217 of FIG. 2A, not shown) for direct digital T1 network facilities.

A trunk group is determined during the digit analysis based on the dial plan. If the current CPC trunk interface is a member of the selected trunk group, the trunk can be seized. CPC processor 401 enables SCR circuit 417 to seize the appropriate trunk circuit.

Each line side port may be either a loop or ground start operation. Ground start relay circuit 427, under control of CPC processor 401, provides the ground start feature.

When the CPC trunk interface is not in the trunk group selected, the call must be switched to an alternate CPC path. The alternate CPC path selection is initiated by message via COM port 419 to the DCC (i.e., 225 of FIG. 2A, not shown).

DTMF senders 409 under control of CPC processor 401 are attached to outpulse the network information digits. Based on the network trunking plan, various interface protocols may be supported (debit, collect, long distance, etc.).

During network seizure, information outpulsing and call setup, various call progress tones or states may be encountered. The CPC line interface logic supports detection of these network progress tones and supervisory states. Progress tone decoder circuit 429, under control of CPC processor 401, detects the various network progress tones. Complex software and hardware algorithms are used to detect network progress tones and states. The states include dial tone 431, congestion busy signal, subscriber intercept tone, call intercept announcement, line busy signal, ringback tone 433, ring no-answer, answer supervision, and quiet. Loop polarity detection circuit 435 in CPC 210 supports hardware answer supervision. The detect circuit looks for a reverse tip and ring loop polarity.

Optionally, CPC 210 has "CLICK" detect circuit 437 which monitors the network line when answer supervision has been declared. The circuit supports detection of a rotary dialed called party acceptance. Call acceptance by the called party using a touch-tone telephone is detected via an enabled CPC DTMF receiver. "CLICK" detect circuit 437 also supports flash-hook detection used for third-party/conference call setup by the called party telephone.

The PSTN analog trunks utilized with the present invention are typically two-wire line interfaces used for local TELCO access. For this type of line, CPC 210 connections appear on type 66 distribution blocks, which are used to cross-connect the CPC ports 240 to the TELCO lines, or to the IDC ports.

Figure 5:
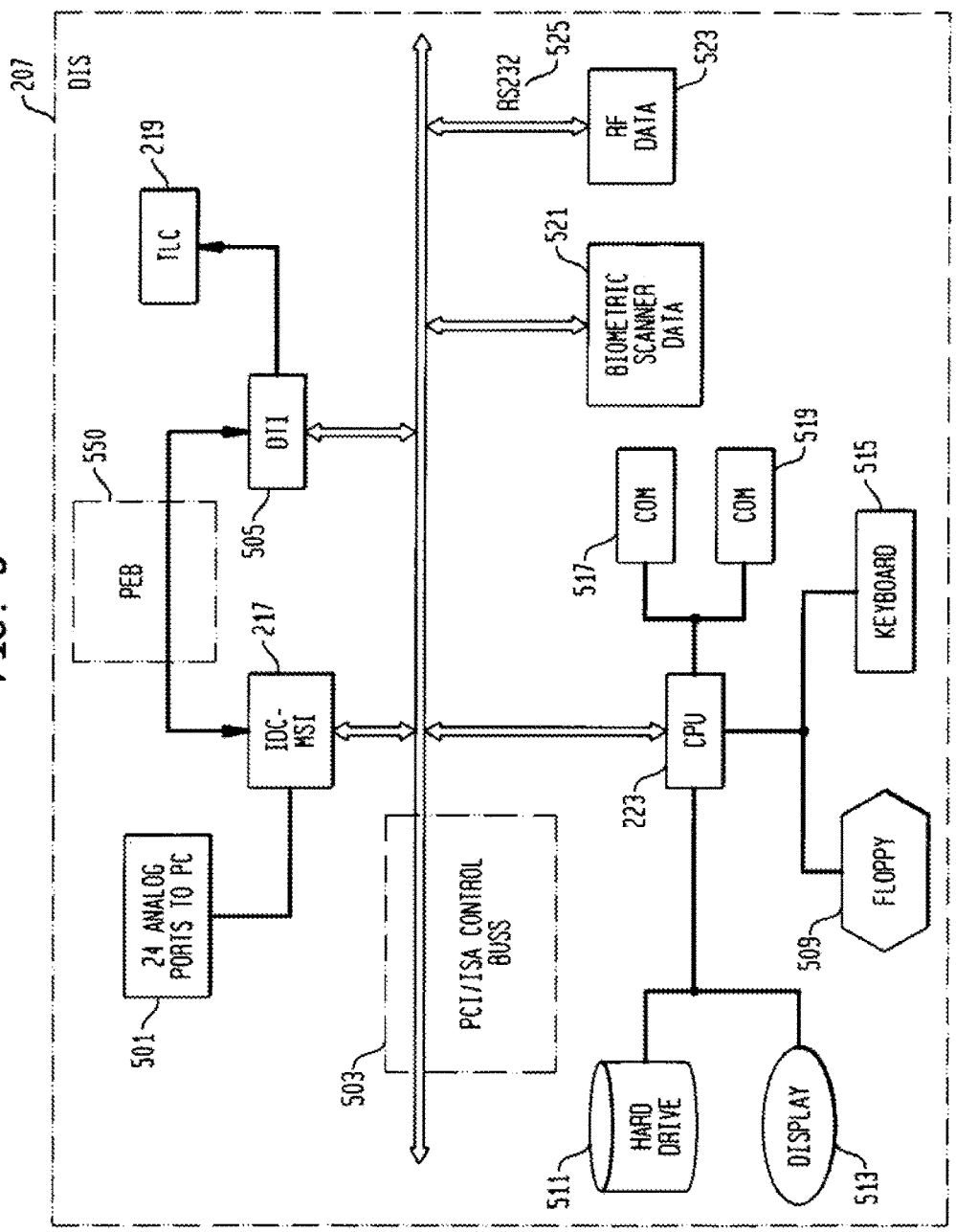
FIG. 5 depicts a detailed schematic representation of the Digital Interface Subsystem (DIS) of FIG. 2A.

Referring next to FIG. 5, shown is a block diagram of digital interface subsystem (DIS) 207. IDC-MSI card 217 provides integrated analog to digital (A/D) conversion. A/D conversion is performed on the voice circuits from the CPC ports 240 to the digital T1 interface card (TLC) 219. Analog ports from CPCs connect to IDC-MSI card 217 at IDC analog interface port 501. Each analog interface port 501 contains electrostatic discharge circuits to filter out sharp high voltage transients. A line interface circuit provides loop control and transmission battery feed. The coder/decoder (CODEC) converts inbound audio from analog to 8-bit digital audio signals and outbound audio from digital to analog, aiding in voice recording, biometric authentication, and the like.

The CODEC's digital audio signals are gated onto the time slot interchange (TSI) switch. The TSI receives digitized audio signals from the CODEC. Channel switching/connection signals are provided from the onboard control processor for each of the 24 channels.

In the preferred embodiment, the TSI switch acts as a traffic coordinator to buffer and gate the digital data from each channel. After the digital data is managed by the TSI switch, the digital signals are routed to PCI-I 221 (shown in FIG. 2A). Digital signals are in a Digital Service Level 0 (DS0) format. DS0 channelized signaling is a 64 Kb/s data digitizing rate used for T1 and E1 systems. Although Digital Service Level 0 (DS0) is utilized in the present embodiment, other formats compatible with the objectives of the present invention may be utilized depending on the requirements of an institution call system. PEB buss 550 links IDC-MSI card 217 PCM channels to TLC 219 and DTI 505.

IDC-MSI card 217 is slave to the digital subsystem CPU card (CPU) 223. In the present embodiment, IDC-MSI card 217 edge connector supports PCI/ISA control buss format, however, other formats may be supported.

In the preferred embodiment of the present invention, DTI hardware 505 is a commercial design presently known in the art. Deployed in a large number of switching applications, the design is a proven technology. Specifically, the design is a derivative of a hardwire design similar to Dialogic's® D/24-SC-T1 digital T1 interface card.

The basic function of TLC 219 is to provide an integrated digital T1 network interface. When using the institution call system of the present invention, it replaces the need to use special channel bank type equipment.

Digital subsystem CPU controller card 223 hardware is a commercial design. The design is a proven technology and supports various TELCO system applications. Key functions of CPU 223 include the processing of the digital interfaces, subsystem statistics, user inquiries, etc.

Digital subsystem controller card 223 is a full size card. The Pentium processor based CPU 223 accommodates up to 256 MB DRAM memory. A secondary level 512 KB cache is also provided. Communications between digital subsystem CPU controller card 223, TLC 219, and IDC-MSI 217 is provided by the PCI/ISA buss. Floppy disk controller 509 supports loading updated programs/data files. Hard disk 511 provides storage media for digitized voice and data files.

Inquiry requests may be initiated by a user of the system from one of the available telephones. Unique access codes along with the PIN number, biometric authentication, voice samples, or RF authentication, may be entered once the user receives dial tone from digital subsystem CPU controller card 223. When digital subsystem CPU controller card 223 receives the digits, it connects to the line side and resends the digit information to IDC-MSI 217. The analog information is digitized by IDC-MSI 217 and routed via PEB buss 550 to TLC 217. Information digits may then be processed by digital signal processors (DSPs) in TLC 217.

TLC 217 has drop-and-insert capability to support digital data outputs that may be processed by digital subsystem CPU controller card 223. The drop-and-insert feature in addition supports playback of digital voice prompts during the inquiry process.

Digital voice files are preferably stored on hard disk 511 of digital subsystem controller card 223, although the digital voice files may be stored anywhere accessible to the system, whether local or remote. The processing of digit information and the use of special menus support the interactive inquiry process. In this embodiment, the recorder is incorporated into CPU 223. CPU 223 also contains software capable of analyzing biometric data from biometric sensor 109 (all depicted in FIG. 1, not shown) via COM port 521. As described above, speaker independent voice recognition software and speaker dependent voice identification software is commonly available and may be implemented by general purpose central processing units such as CPU 223. CPU 223 thus can be implemented to retrieve samples of speech from the user to verify a user to access the telecommunications system of the present invention. It also contains software to analyze RF data 523 from RF receiver 107 via COM port 525.

Digital subsystem CPU controller card 223 LAN interface supports communication with the servers and associated inmate account information. This supports account transaction processing between ITAC and other inmate data files.

Digital subsystem CPU controller card 223 board connectors support connection to external I/O devices. For example, CPU 223 may include display 513, keyboard 515, and/or COM ports 517 and 519.

Figure 6:
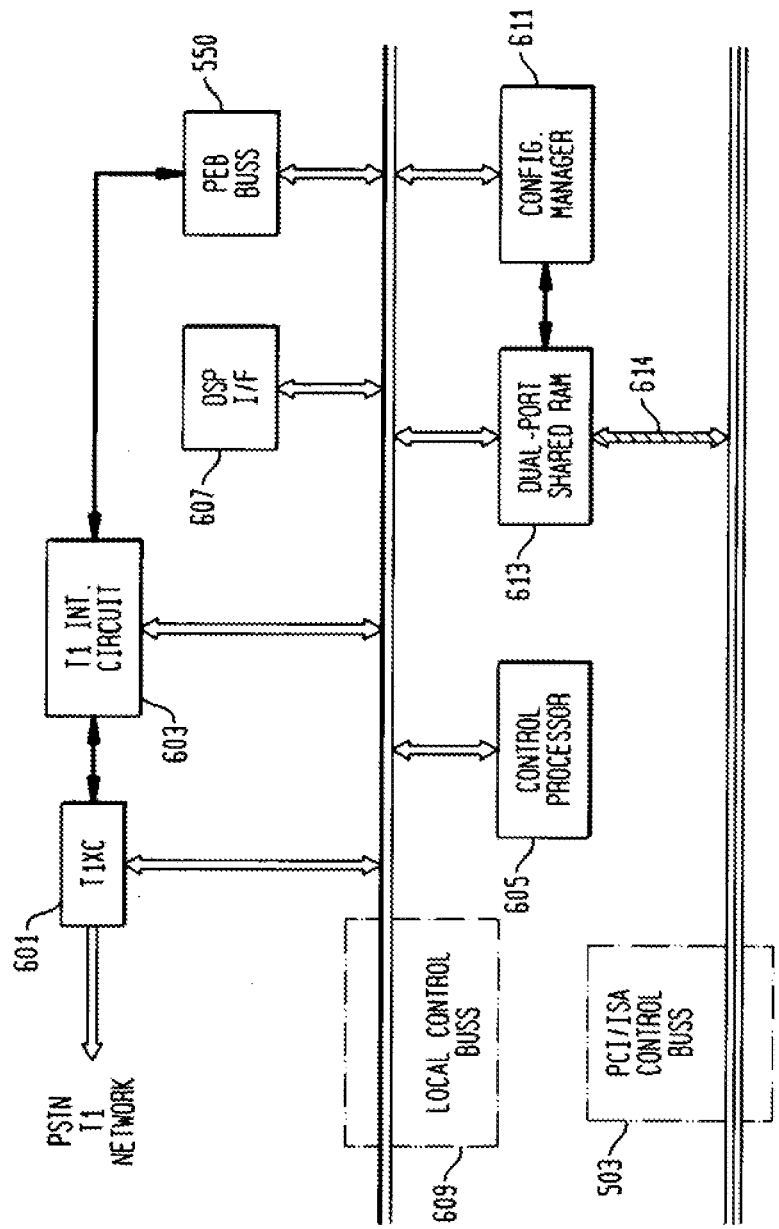
FIG. 6 depicts a detailed schematic representation of the digital T1 interface card (TLC) of FIG. 2A and FIG. 6.

Now referring to FIG. 6, displayed is a schematic diagram of the interface structure of TLC 229. The TLC 229 is an integral part of the digital interface system of the telephone call management system of the present invention. Digital T1 signals from the network enter the DTI-IDC card (not shown) via T1XC line interface 601. The incoming T1 bit stream is interfaced to T1 interface circuit 603. T1 interface circuit 603 acts like a traffic coordinator for gating the digital signals. It buffers the digital data received for each channel and interfaces the data to PEB buss 550. The serial bit stream contains the digitized voice and signaling information for each channel. Under the control of TLC onboard control processor 605, T1 interface card 603 can route a channel being processed to any available PEB buss 550 time slot.

PEB buss 550 supports up to 24 time slots in the preferred embodiment of the present invention. However, the number of time slots may be altered depending on the desired capacity of the call system of the present invention. This enables the telephone call management system to route channels to/from the IDC-MSI card. Each time slot is a digitized bit stream and represents one voice channel. This enables T1 interface card 603 to switch voice channels on PEB buss 550 to and from the IDC-MSI card analog interface ports.

PEB buss 550 time slot data may be routed to a series of digital signal processor (DSP) 607 interface. DSP 607 processes the digitized audio signals data on each channel. This design supports channel drop-and-insert capability. Under control of TLC onboard control processor 605, digital data may be extracted from the bit stream and/or inserted into the bit stream.

Digital signal processor 607 supports user inquiry features of the call system and any voice authentication that may be employed. Digital signal processors 607 may be programmed to perform signal analysis, to automatically adjust gain control, to compensate for variations in the level of incoming audio signals, to compress digitized voice data compression, to send and/or receive DTMF or inband signaling, to monitor channel conditions and status, to detect presence of tones (DTMF, MF, etc.), detect silence/quiet, to determine if a caller is not responding, to decompress stored audio data, to compress audio data for playback, to adjust the volume and rate of speed of playback, to signal bit control (off-hook, on-hook, etc.) based on trunk types (FXS, E&M, etc.), etc.

TLC onboard control processor 605 controls TLC 603 operation via local control buss 609. Local control buss 609 interprets and executes commands from TLC onboard control processor 605. Communications between TLC onboard control processor 605 and the host CPU is via dual port shared RAM memory 613. Dual port shared RAM memory 613 acts as an input buffer and/or output buffer. Upon initialization, the operating firmware that controls TLC 603 is downloaded from the CPU. It is downloaded into the onboard code/data RAM via dual port shared RAM interface 614 via PCI/ISA control buss 503.

Specifically, control of the digital interface subsystem is provided by configuration manager 611. Configuration manager 611 determines and sets various board level operational parameters. This feature eliminates the need to set confusing jumpers or dipswitches.

Figure 7:
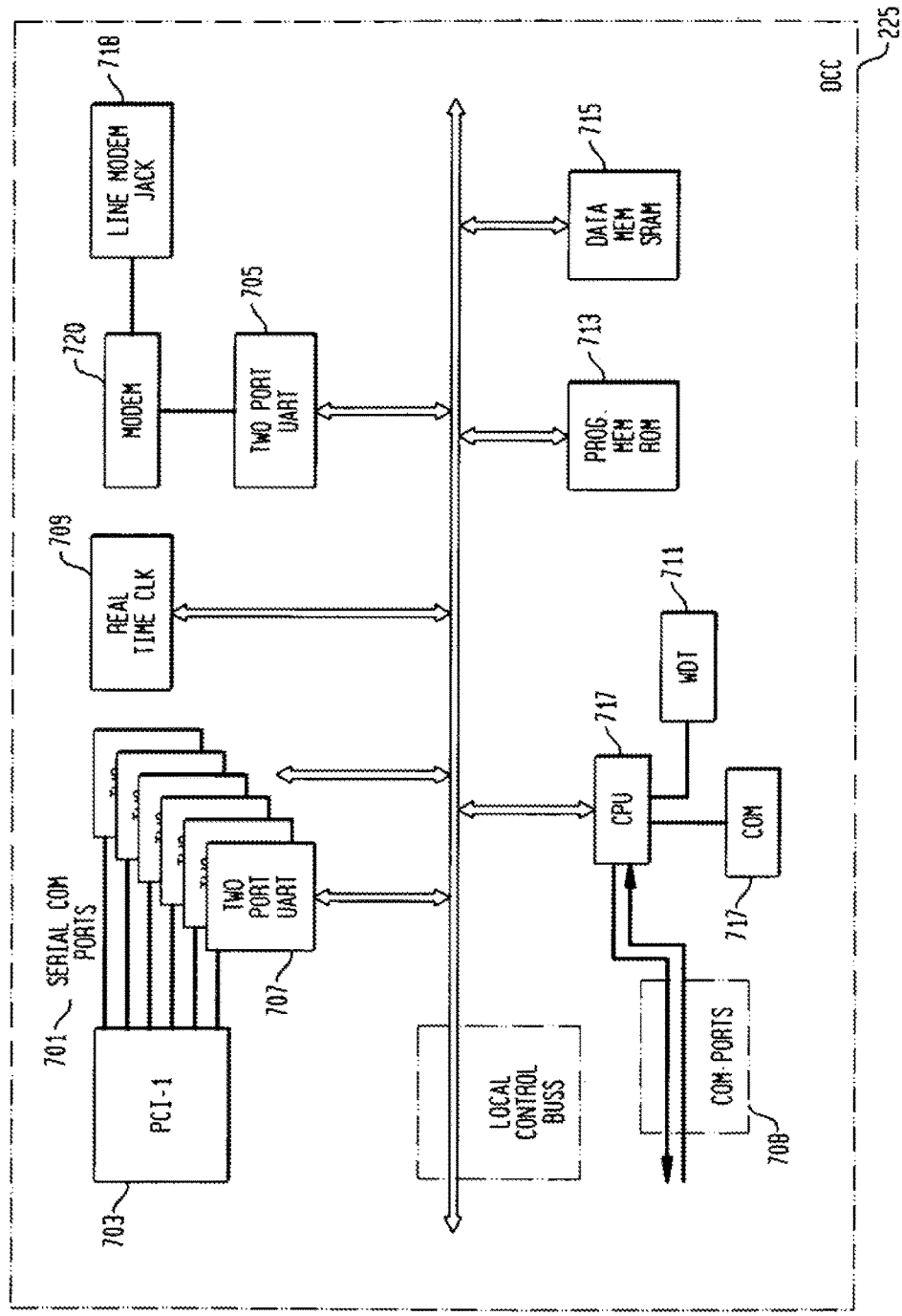
FIG. 7 depicts a detailed schematic representation of the data communications control card (DCC) of FIG. 2A.

Referring next to FIG. 7, shown is a block diagram depicting the performance of the data communication card (DCC) 225 of the preferred embodiment of the present invention, as depicted in FIG. 2A. In the design of the preferred embodiment, DCC 225 supports up to 15 serial communication ("COM") ports 701. However, any number of serial COM ports 701 may be utilized depending on the capacity requirements of the telephone call management system. Server UARTS (Universal Asynchronous Receiver Transmitter) (2 ports per UART, however, any number may be utilized) (i.e., 705, 707) and internal central processor's COM port 717 effect communication between subsystem cards.

In the preferred embodiment of the present invention, one of UART ports 705 supports an internal modem circuit for remote dial access. In addition, six of UART ports 707 are dedicated for connecting up to six CPC serial COM ports 701 from the CPS. Other serial COM ports 701 include one port dedicated for CSC communications and a second COM port dedicated for communications with the system concentrator communication card. Communications between the data communication card and the system memory card is via internal processor COM ports 708.

A battery backed real time system clock 709 on DCC 225 supports an accurate date and time stamp function. This capability is used for time stamping call detail records (SMDR) and reports.

Data communication card central processor 717 sanity is monitored by internal watch dog timer (WDT) 711. This feature provides a hardware type reset for data communication card central processor 717. For example, if a non-recoverable error condition affects the processor sanity, the feature would force reset data communication card central processor 717. Furthermore, WDT 711 feature may force data communication card central processor 717 and/or SMC processor to reset.

DCC 225 has two types of memory located on the board, which include ROM (read only memory) 713, equipped at either 256 or 512 kB in the present embodiment, and SRAM (static random access memory) 715, equipped at 512 kB in the present embodiment. ROM 713 contains the operating programs for DCC 225. On power-up, data communication card central processor 717 boots and initializes the operating programs.

Battery-backed SRAM 715 supports real time and configuration data requirements. Configuration data may be site specific. Alternatively, site programs can be downloaded from remote operations centers.

PCI-1 703 is based on a passive card design. It consists of connectors that distribute and connect signals between subsystem cards. Each call system unit is equipped with one PC card referred to as PCI-I. The PCI-1 card supports the distribution of signals between DCS, SIS, and CPS in each unit. The PCI cards plug into a standard card slot in the Call system unit.

DCC 225 controls and performs communications functions between electronic switchboard unit subsystems. In addition, DCC 225 supports communications with units and subsystems via the CCS. Some operational and maintenance features of the DCC 225 hardware include visual indicators, special line modem access jacks, external serial COM port access jacks, reset & write protect switches, memory equipped options, etc.

In the preferred embodiment, modem access for remote maintenance and administration is supported by line modem 720 and line modem jack 718, such as a RJ14 telephone jack. Generally, the access line usage is low and may be controlled. Therefore, an option makes it possible to share the line for user calling to allow for efficient operations of the call system.

Figure 8:
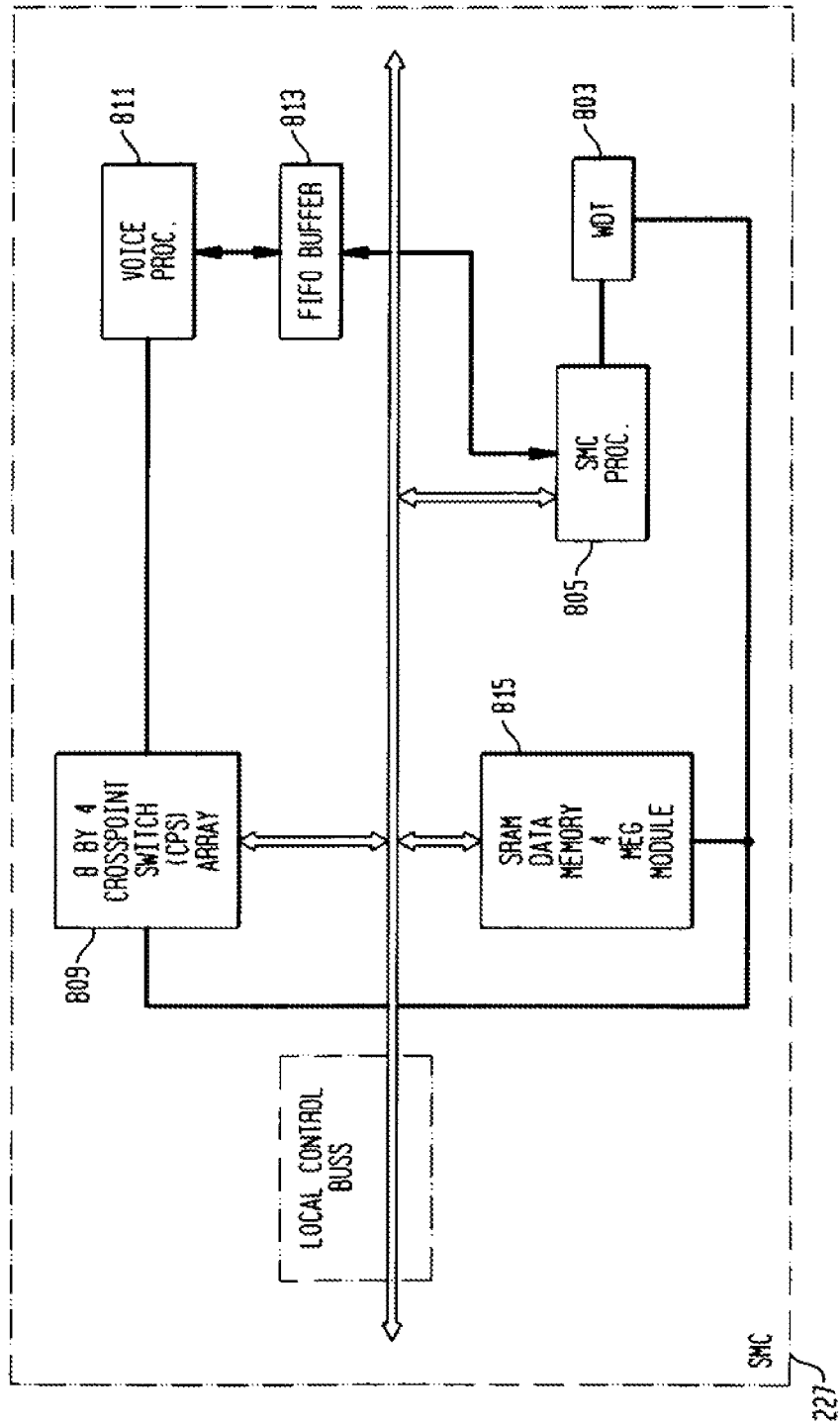
FIG. 8 depicts a detailed schematic representation of the system memory card (SMC) of FIG. 2A.

Next referring to FIG. 8, shown is the architecture of system memory card (SMC) 227 of the preferred embodiment of the present invention as disclosed in FIG. 2A. Functionally, system memory card 227 provides voice processing and buffering of digitized voice files for use as interactive voice prompts and/or use as voice authentication. SMC 227 also performs buffering for call detail records and inmate voice recordings. SMC 227 communicates with the data communication card via the SMC processor 805 internal COM ports. SMC 227 and SMC processor 805 support data and voice communications in the electronic switchboard device of the call system of the present invention. Watch dog timers 803 on processors 805 monitors sanity. SMC processor 805 will reset the internal control of the DCC of the present invention and vice-versa.

The preferred embodiment of the present invention provides for four (8 by 4) cross-point arrays 809. However, other cross-point arrays and configurations may be used. Each cross-point array 809 provides access to the four voice processing circuits on the SMC provided in the preferred embodiment of the present invention. Each equipped CPC provides four audio line record/playback buss connections to SMC 227. Based on a fully equipped unit (6 CPSs per unit at 4 audio line busses each) a total of 24 audio line buss cross-connections are used in the present embodiment. For example, each one of the first three arrays supports four audio line busses from 2 call processing cards. Specifically, each array may access any of the four voice processor circuits 811 of the present embodiment.

Voice processor circuits 811 code user voice signals into digitized voice files for recording and use for authentication. Voice processor circuits 811 also decode user digitized voice files and convert the digital signals to audio signals for playback.

Furthermore, first-in, first-out (FIFO) buffer 813, along with the SMC processor's 805 DMA buss allow larger digitized voice data files to be moved fast and efficiently to and from memory. A multitude of FIFO buffers 813 may be utilized for providing a more efficient call system.

Alternatively, or in addition to the FIFO buffers, memory extension modules 815 may be utilized and designed as plug-in modules for the SMC 227 (as depicted in FIG. 2A, not shown). Memory extension modules 815 contain four Meg memory expansions per module in the preferred embodiment of the present invention.

Figure 9:
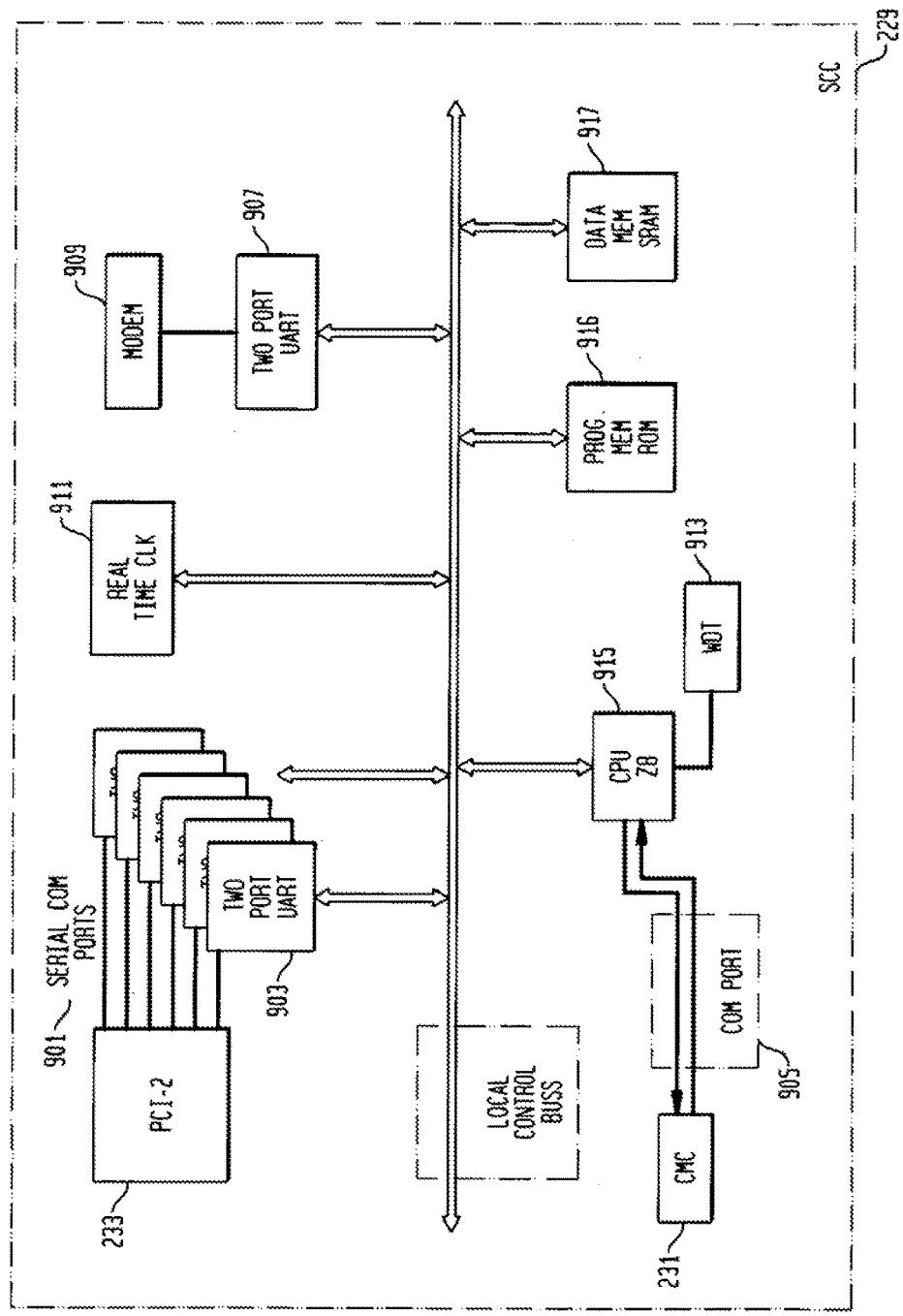
FIG. 9 depicts a detailed schematic representation of the concentrator memory card (CMC) of FIG. 2A.

Referring next to FIG. 9, depicted is a block diagram of the system concentrator card (SCC) 229. SCC 229 is a communications interface controller between multiple electronic switchboard devices and is generally integrated within the electronic switchboard device of the present invention. SCC 229 supports and controls up to 15 serial COM ports 901 in the present embodiment of the invention. Serial COM ports 901 generally comprise 7 DARTS 903 (2 ports per DART) and the see internal processor's serial COM port 905.

Specifically, in this embodiment, one DART port 907 supports an internal modem circuit 909 for remote dial access. Typical COM ports used in SCC 229 include four serial COM ports which are used to connect to the Dec in each electronic switchboard device unit equipped and one serial COM port used to connect to a server COM port. In the present configuration, the SCC processor's COM ports 905 connect directly to the CMC 231 COM port. Furthermore, a battery backed real time clock circuit 911 is also part of the SCC design.

SCC internal processor 915 sanity is monitored by an internal watch dog timer feature 913. This feature provides a hardware type reset for SCC internal processor 915. If a non-recoverable error condition affects the processor sanity, the feature force resets the SCC internal processor 915.

SCC 229 comprises two types of memory located within the system. Specifically, SCC 229 includes programmed memory ROM 916 (read only memory), equipped at either 256 or 512 kB in the present embodiment, and data memory SRAM 917, (static random access memory) equipped at 512 kB in the present embodiment. Although the specific memory capacity for the system is provided for disclosure purposes, it is foreseeable that additional memory, either internal or external to the system, may be provided depending on he desired capacity of the call system. Generally, ROM is used for program memory and contains the SCC's operating software.

In the preferred embodiment, CMC 231 performs buffering for call detail records as a backup to the system memory card. The CMC 231 communicates with the system concentrator communication card via the processors internal COM ports 905. Together they support data communications in the telephone call management system. Watch dog timers 923 on the CMC and SCC processors monitor sanity. A reset from either processor will reset the companion processor. The CCS's CMC uses the same basic hardware as the SMC equipped in the DCS.

Call system software controls all monitoring, recording, financial transactions, and other call processing features. In the preferred embodiment of the present invention, call system software contains six main components. A general description of the call system software is provided herein to offer a general understanding of the possible software for use with an investigative call system. However, the description provided is not intended to provide the full scope of software functions compatible with the present invention. For example, a system administrator section controls which institution authorizes hardware and telephone access to the system. A user administrator section controls which prison authorities have access to the software. Specifically, in a prison environment, the warden may have access to modify all features within the system whereas a guard may only be able to change user profiles in his own cellblock. The account section allows inmate profiles to be created and modified. It monitors the inmate's calling data and financial transaction data. A shadow section allows the software to control the various Spybox monitoring stations to listen to inmate calls. A fifth section allows users of the software to compile various system reports, such as net monthly financial transactions and an extra digits dialed report. A final section processes the biometric information and the RF data for use in authentication. This section uses various algorithms to check a user's recorded information against data supplied to the biometric scanner and RF receiver.

System administration software allows an institution staff member to define defaults and to customize the system. Generally, only authorized staff members may have access to customize system settings, based on individual staff member security levels. However, a user security level may be determined when a user first logs into the system containing the call system software based upon username and the access level that has been set for each user name by a user manager. The sub-menus of software may include class of service (COS) maintenance, living unit maintenance, telephone location maintenance, facility telephone number control, nationwide telephone number control, call pricing, facility default maintenance, transaction type maintenance, etc. In addition, the institution employees may have access to update multiple telephone lists, view calls in progress, monitor calls in progress, manually modify transactions, enable/disable telephones, modify the class of service, etc.

Figure 10:
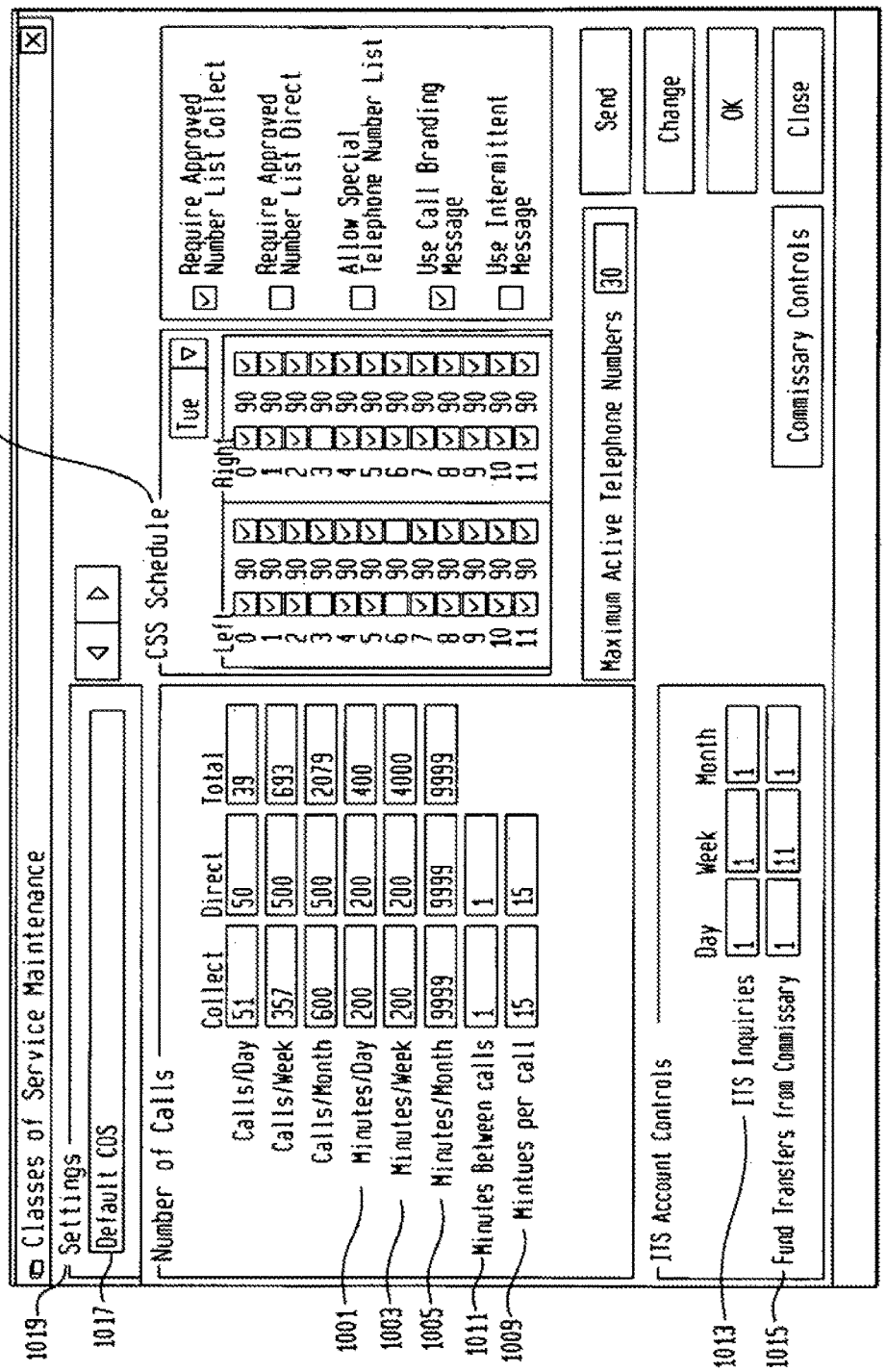
FIG. 10 depicts a sample class of service menu for use with software contained in the call management system of the preferred embodiment of the present invention.

Referring next to FIG. 10, depicted is a sample class of service maintenance menu 1000 integrated with the current system of the present invention. The class of service maintenance menu 1000 may be provided to an authorized institution agent for monitoring the various aspects of the call system of the present invention. Various classes of service maintenance menus (from very simple general menus to extensive broad menus) may be provided in accordance with the general objectives of the present invention. However, depicted is a general class of service maintenance menu 1000 illustrating certain common features as presented in a standard IBM compatible software based program. Although numerous software protocol systems may be utilized in accordance with the overall objectives of the present invention, it is preferred that Microsoft Windows® based programs are utilized. However, the present invention is compatible with other types of operating systems that may be employed depending on the requirements of the institution. In class of service maintenance menu 1000, numerous points of information are depicted for users, including, but not limited to the total number of minutes allowed per user in any given day 1001, week 1003, or month 1005. It is foreseeable that class of service maintenance menu 1000 also sets the dates and times 1007 that calls may be made, as well as telephone call maximum duration 1009 and the time duration between calls 1011. Authorized system users may also set restrictions on access to the inquiry system via data input fields. For example, a data input field may be provided for limiting the number of inquiries 1013 or limiting the number of transfers from the commissary 1015. Further parameters can be determined by system users by changing class of service (COS) maintenance settings 1019. For example, for ease of application, access levels usually match the 'Default COS' 1017, but may be customized for each user.

Figure 11:
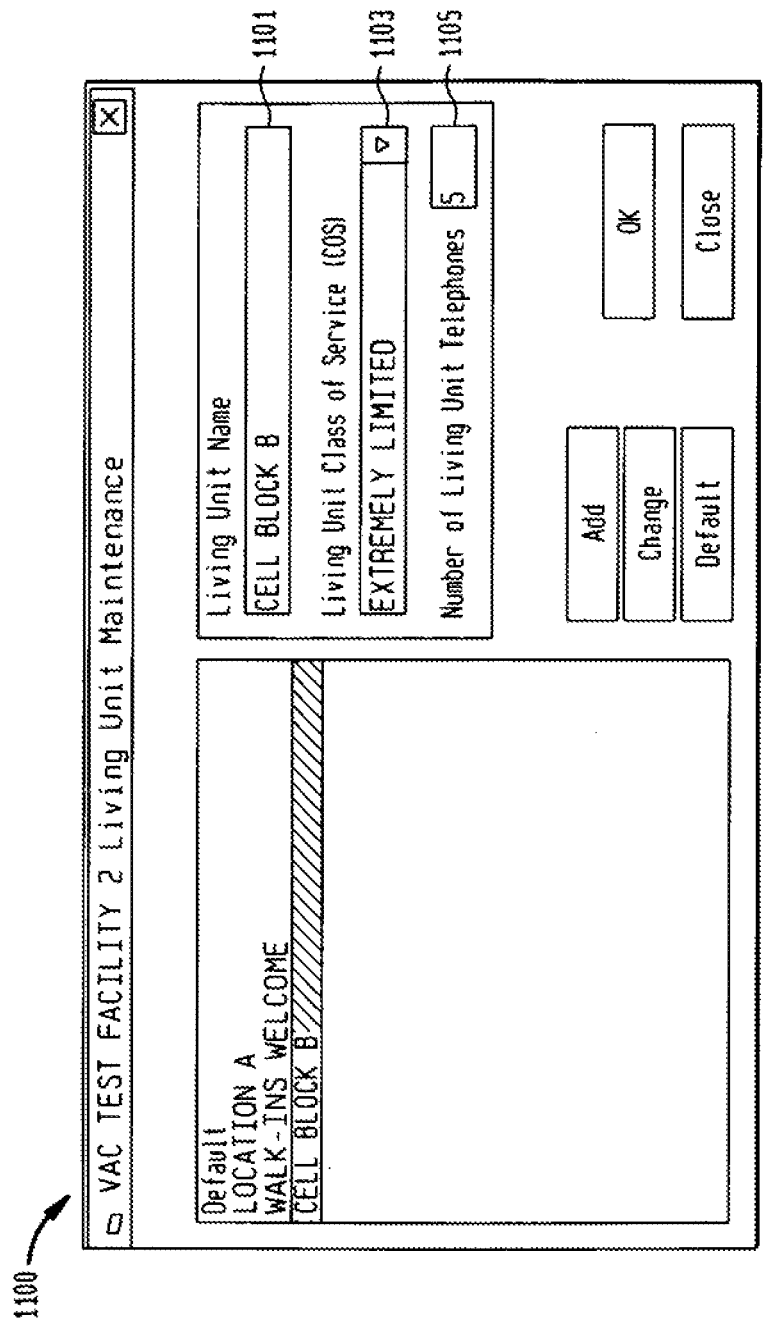
FIG. 11 depicts a sample authorized maintenance interface screen for use with software contained in the call management system of the preferred embodiment of the present invention.

Now referring to FIG. 11, shown is authorized agent maintenance interface screen 1100. Many institutional facilities include individual buildings, departments, wings, etc. (e.g., the term cellblocks is often used or different divisions of a prison facility). As depicted in authorized agent maintenance interface screen 1100, the call system of the present invention refers to these as "living units". As represented in the authorized agent maintenance interface screen 1100, several control settings can be applied to an entire living unit at a time, including setting the default COS for the unit. If assigned, a personal designation overrides a living unit designation and a living unit designation overrides a facility designation. For example, in a correctional facility, living unit name 1101 is the name assigned to the cellblock (e.g., "Cell Block B", "Cell Block C", etc.). In addition, in this example, the living unit COS 1103 is the default COS that will be assigned to inmates assigned to that living unit. Furthermore, the number of living unit telephones 1105 is for informational purposes only, and does not affect the program. Further, options may be available depending on the requirements and capacity of an institution.

Referring next to FIG. 12, depicted is a sample telephone location maintenance screen 1200 utilized in the present invention. For example, telephone location maintenance screen 1200 allows an institutional staff member to define for each telephone station which user telephone account control server may be utilized defined in site server name field 1201. In addition, station number field 1203 provides a data entry point for assigning the station ID or station number to address each telephone location. Living unit field 1205 provides institutional staff members a data entry point to address the telephone locations in various location blocks throughout the institution. Location field 1207 allows users access to specific trunk lines within the call system. Finally, telephone locations summary block 1209 provides a general summary to a staff member for maintaining a call system.

In this example, all parameters except the line number can be changed by staff members' intervention. Further options may be accessible depending on the requirements of an institution.

Figure 13:
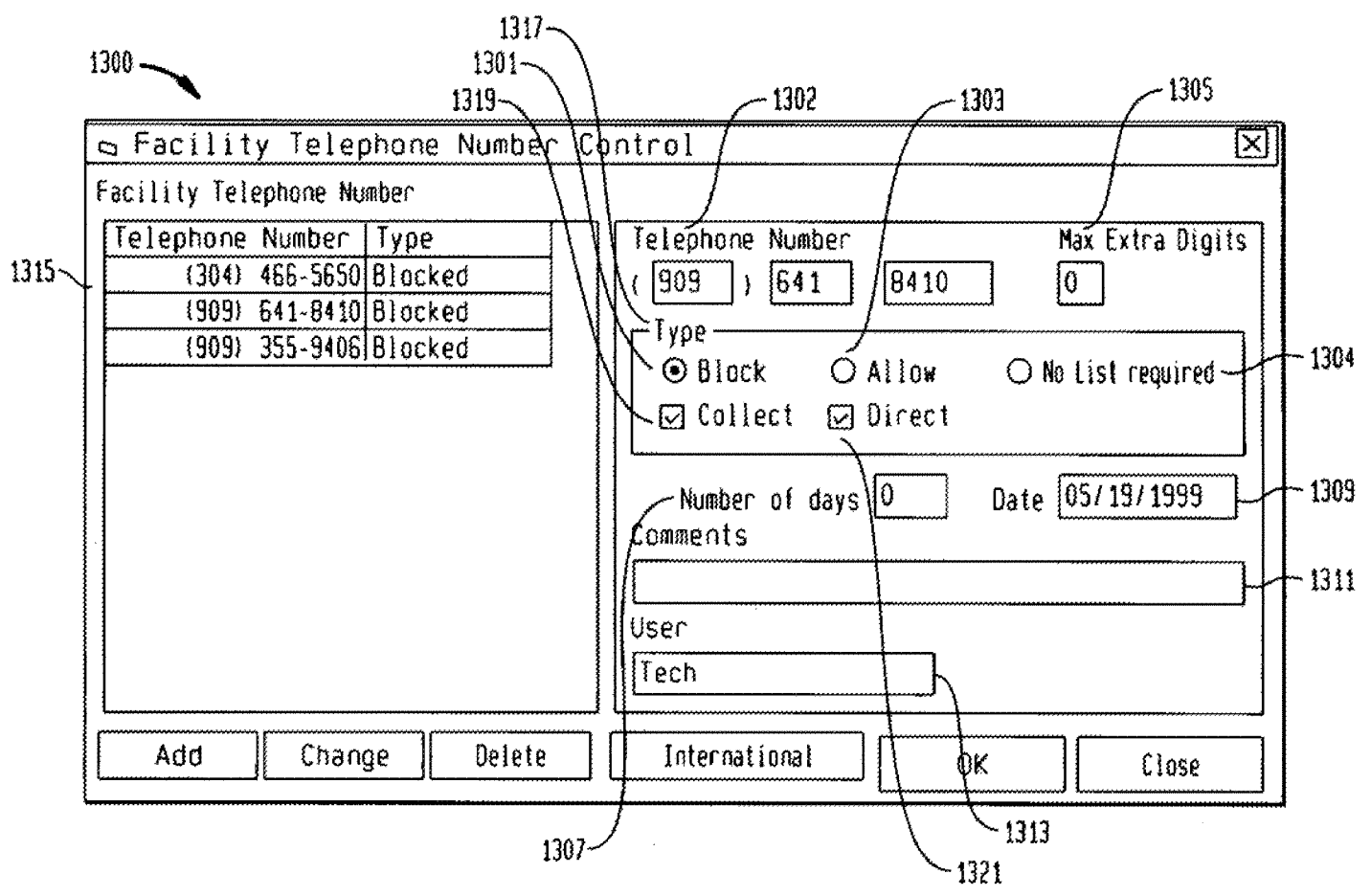

FIG. 13 depicts a sample facility telephone number control screen 1300. Facility telephone number control screen 1300, accessed from a main screen, provides authorized users the ability to define a list of numbers that supercedes the user's personal telephone number list 1315 for either collect and/or direct dial numbers at the facility level. Each telephone number can be modified in the telephone number field 1302. A maximum extra digits field 1305 indicates the number of digits a user is allowed to dial after a call has been connected.

Facility telephone number control screen 1300 additionally contains call type block 1317 that contains a number of fields indicating the type of call. Block field 1301 is selected if a telephone number is not allowed on the user's personal list. Allow field 1303 is selected if the telephone number in telephone number field 1302 is on the user's allowed list. If no list required field 1304 is selected, a user does not have to place the telephone number on their personal list in order to call it. Type block 1317 additionally contains collect field 1319 which is selected if a user is authorized to call the number collect. Similarly, type block 1317 also contains direct field 1321 which is selected if a user is authorized to call the number utilizing direct call means.

Facility telephone number control screen 1300 additionally contains a number of days field indicating the number of days a telephone number is actively on the list. In this example of the present invention, setting number of days to "*" will cause the number to be active on the list indefinitely. Any number greater than "*" will cause the number to only be active for that number of days.

Brief comment field 1311 may be used to describe the reason a telephone number is on the list or any other like comments. The user security level that added the number is indicated (and cannot be modified) in "User" field 1313.

Depicted in FIG. 14 is a sample tasks/system nationwide telephone number control screen 1400. For example, telephone number control screen 1400 allows authorized users the ability to define a list of numbers that supercedes both the user's personal telephone number and facility number control list for either collect and/or direct dial numbers at the national level. Telephone number control screen 1400 can be accessed from a main menu.

Telephone number control screen 1400 contains a list of telephone numbers 1402 which can be assigned a "Blocked" designation 1401 or an "Approved" designation 1403. Blocked numbers will not be connected even if they are on a user's personal list. Approved numbers are connected even if they are not on the user's personal list. Numbers can also be assigned an "Exclude" designation 1404 set to exclude. Excluded numbers are not included in any lists or filters generated using wildcards. The number of extra digits dialed field 1405 can be used to limit the number of digits a user is allowed to enter after a telephone call has been connected to prevent a user from achieving an unauthorized connection or for certain-gaming telephone options.

A number of days field 1407 is used to set the number of days that a number is actively on a user's list. In this example of the present invention, setting number of days to '0' will cause the number to be active on the list indefinitely. Any number greater than '0' will cause the number to be active for only that amount of days, starting from when the number was added to the list as indicated by Date field 1409.

Comment field 1411 is used to describe the number or the reason the number is on the list. User field 1413 indicates the user security level needed to add/edit a number on this screen. In this example, user field 1413 cannot be modified.

Figure 15:
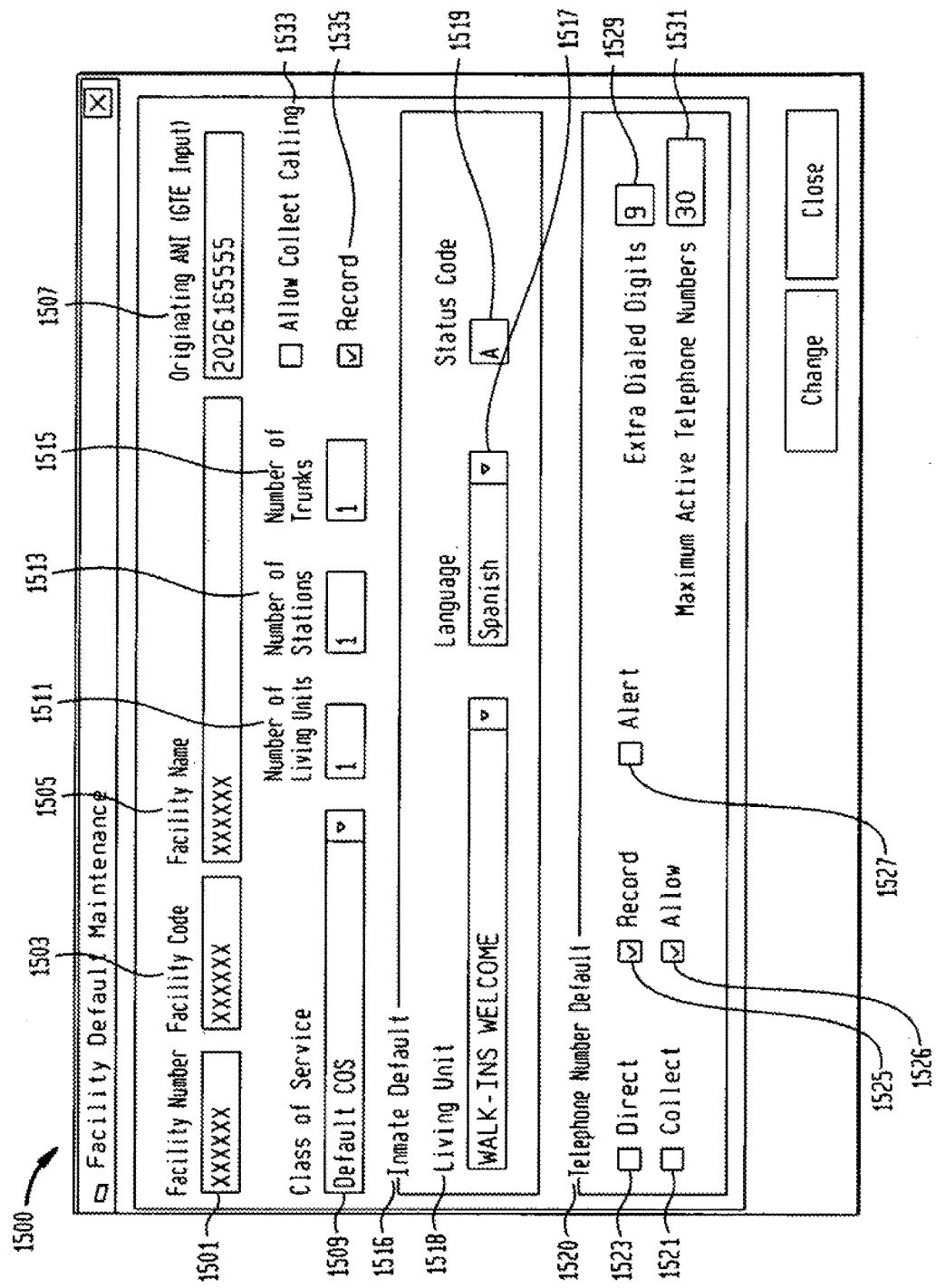
FIG. 15 depicts a sample default maintenance screen for use with software contained in the call management system of the preferred embodiment of the present invention.

Referring next to FIG. 15, shown is an example default maintenance screen 1500. At the top default maintenance screen 1500 are facility number field 1501, facility code field 1503 (automatically generated three-letter designation code), facility name field 1505, and originating ANI field 1507. Facility number field 1500 indicates the number assigned to the facility to which the options on this screen apply. Similarly, facility code field 1503 contains a three-character designation automatically assigned to each facility. Facility name field 1505 indicates a user-specified name assigned to each institution. ANI (Area Number Identified) field 1507 displays the caller's telephone number. Basically, the originating ANI data identifies the source of a call. Despite having multiple lines, a facility might only have one ANI so that all calls are identified the same way. The ANI field is useful for cross-referencing invoices received from local exchanger carriers or Inter-Exchange carriers to the institution.

A class of service parameter 1509 allows an authorized user to choose a specific class of service from a drop down list (e.g., "Default COS", "COS 1", "COS 2", etc.). Number of living units field 1511 indicates the number of living units in each facility. Number of telephone stations field 1513 displays the number of telephone terminals in use in each living unit. Number of trunk lines field 1515 indicates the number of trunks available at the facility.

Facility default maintenance screen 1500 additionally includes user default block 1516. In the example of FIG. 15, user default block 1516 is an inmate default block 1516. Inmate default block 1516 contains living unit menu 1518 from which different living units can be chosen. For each living unit accessible from living unit field 1518, the default language can be selected from language field 1517. Status code field 1519 contains a letter associated with specific features of the institution.

Telephone number block 1520 contains the default settings used for all telephone numbers in class of service field 1509. Direct call field 1523 indicates if direct call access is allowed. Similarly, collect call field 1521 indicates if collect call access is allowed. Record field 1525 indicates if calls are to be recorded. Allow field 1526 indicates if added telephone numbers are to be allowed by default. Alert field 1527 indicates if all telephone numbers added under this particular class of service are to be flagged in a user's profile. Additionally, telephone number default block 1520 also contains an extra dialed digits field indicating the number of digits that a user may press after a call has been connected and a maximum active telephone numbers field 1531 indicating the number of allowed telephone numbers on any user's list.

Figure 16:
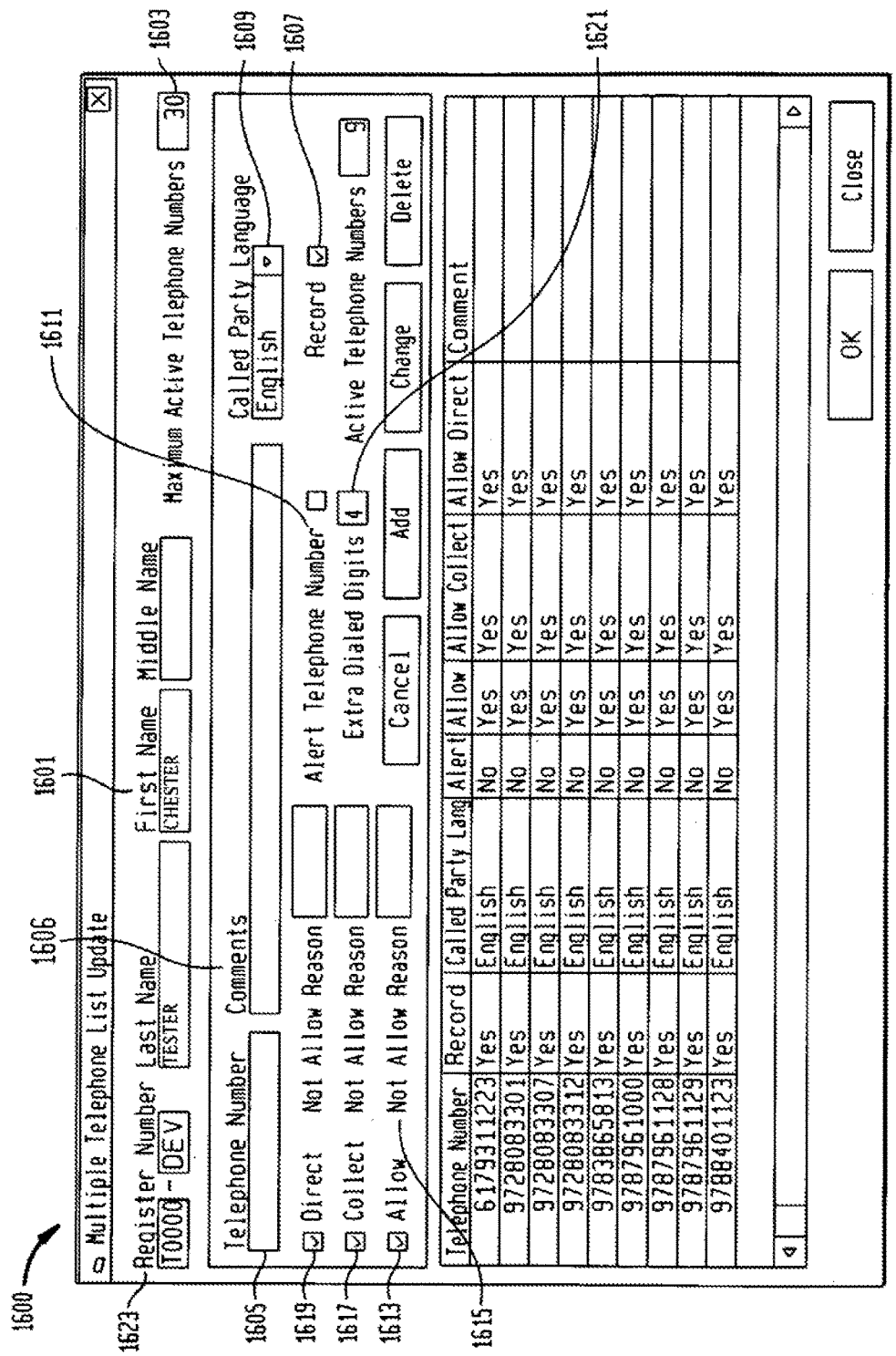
FIG. 16 depicts a sample multiple telephone list update screen for use with software contained in the call management system of the preferred embodiment of the present invention.

FIG. 16 depicts an example of a multiple telephone list update screen 1600. Multiple telephone list update screen 1600 is used to rapidly add several telephone numbers to an inmate's account in a manner that allows an authorized user to see which options have been chosen for each number simultaneously. The information display includes multiple fields. Register number field 1623 displays the unique eight-character number associated with each user authorized under the call management system to place outbound telephone calls. Name field 1601 includes sections indicating a user's first name, last name, and middle initial. Maximum active telephone numbers field 1603 displays the maximum numbers that a user may have on their individual telephone list. Telephone number field 1605 displays the telephone number for which options are being set. New numbers can be added in this field or old ones may be modified. Comments field 1606 can be used to add any information significant to the telephone number listed in telephone number field 1605. Called party language field 1609 is used to select the language used for voice prompts that interface the called party. Record field 1607 can be selected if all calls placed to the specific number are to be recorded. In this example of the present invention, all calls are recorded by default. Alert telephone number field 1611 indicates if the telephone number is to be flagged in a user's profile. Extra dialed digits field 1621 indicates the number of digits a user may enter after a telephone call has been connected.

Multiple telephone list update screen 1600 additionally contains fields limiting access to different call methods. Allow field 1613 is used to indicate if a user is authorized to contact the specified number. A not allow reason field 1615 allows a comment to be added indicating why the number is blocked. Collect field 1617 indicates if a user can access the number utilizing collect call means. Similarly, direct field 1619 indicates if a user can access the number utilizing direct call means.

Figure 17:
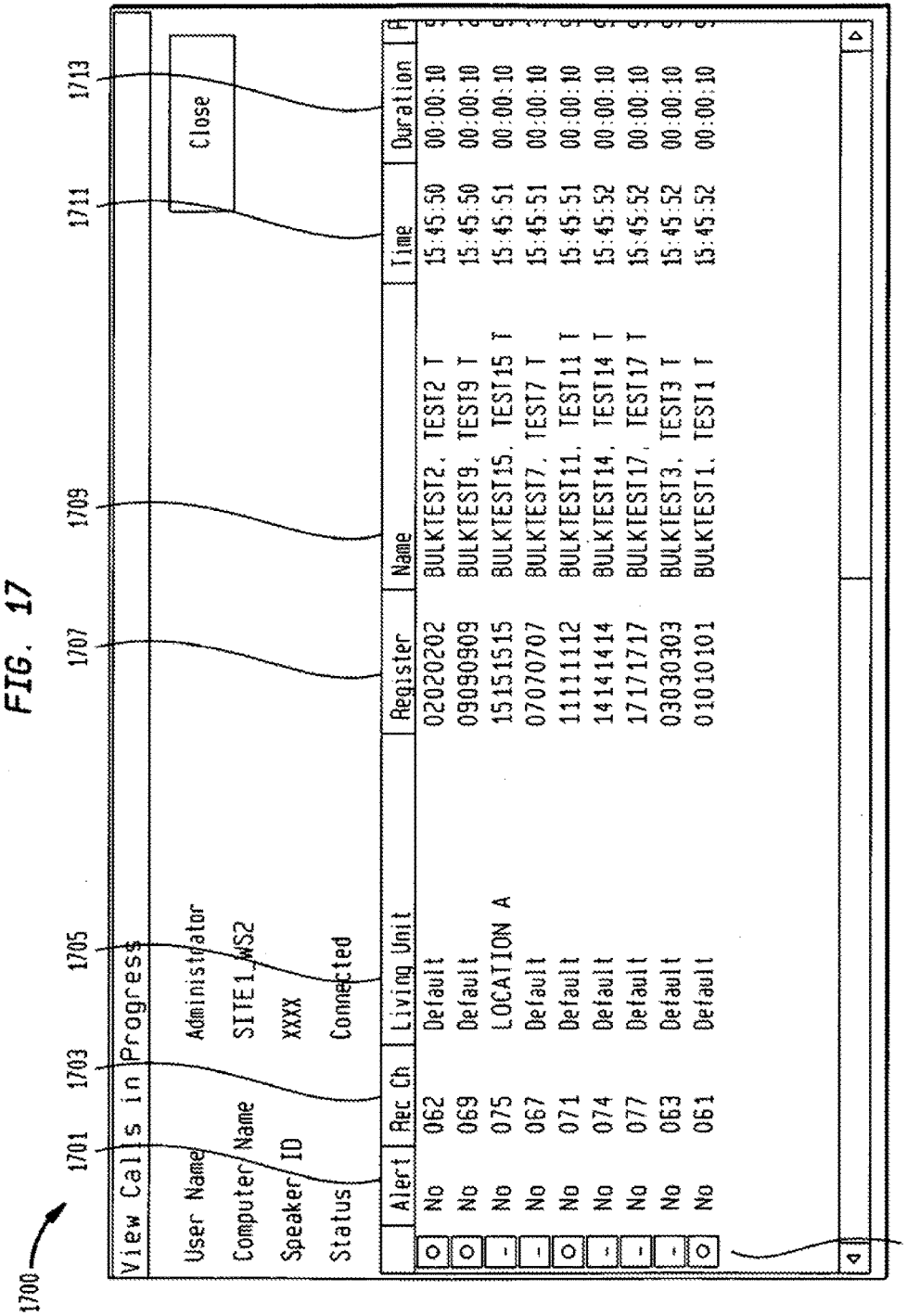
FIG. 17 depicts a sample calls in progress screen for use with software contained in the call management system of the preferred embodiment of the present invention.

Referring next to FIG. 17, shown is a view calls in progress screen 1700 that enables a call system administrator to oversee a list of calls currently in progress. Each telephone station's status is indicated by activity icon 1702 in the first column shown on view calls in progress screen 1700. A number of column headings are used to indicate the different statuses of each telephone terminal. An alert column displays "Yes" if the called number has caused an alert or "No" if the called number has not caused an alert. Recorder channel column 1703 indicates the recorder channel being used for each telephone conversation currently in progress. Living unit column 1705 displays the living unit from which the call is being placed. Register column 1707 displays the user utilizing each telephone station. Name column 1709 displays the user's name associated with the register number displayed in register column 1707. Time column 1711 indicates the time a call was initiated. Duration column 1713 displays the amount of time a call has been in progress.

Figure 18:
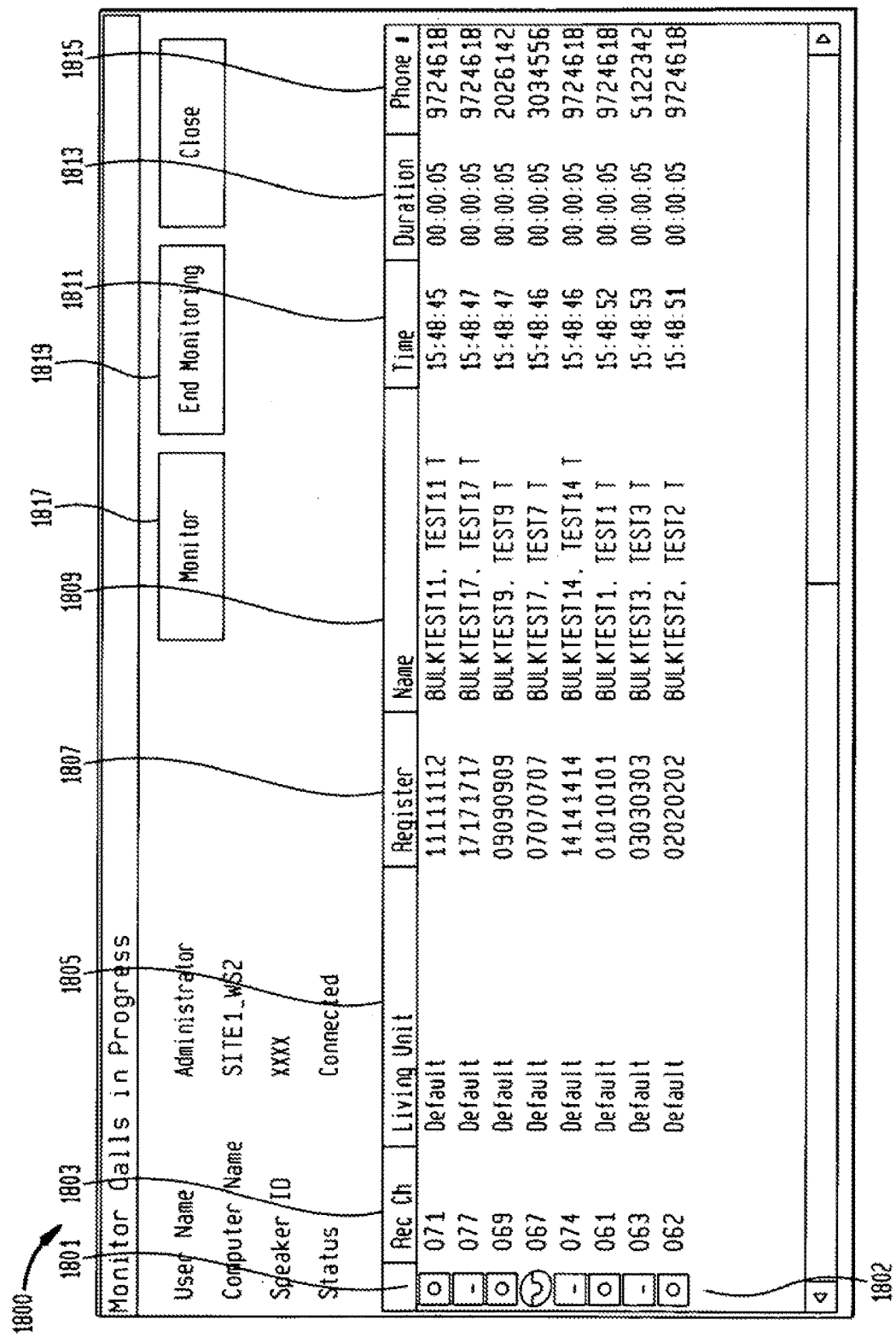
FIG. 18 depicts a sample monitor calls in progress screen for use with software contained in the call management system of the preferred embodiment of the present invention.

Now referring to FIG. 18, shown is an example of a monitor calls in progress screen 1800 that is part of the system administrator software. Call monitoring allows the institution to listen in on specific calls. This is done through the skybox devices. Neither the user nor the recipient of the call will be able to detect any change in sound quality to indicate that a call is being monitored. Each telephone station's status is indicated by icon 1802 in the first column 1801 shown on view calls in progress screen 1800. A number of column headings are used to indicate the different statuses of each telephone terminal. An alert column displays "Yes" if the called number has caused an alert or "No" if the called number has not caused an alert. Recorder channel column 1803 indicates the recorder channel being used for each telephone conversation currently in progress. Living unit column 1805 displays the living unit from which the call is being placed. Register column 1807 displays the user utilizing each telephone station. Name column 1809 displays the user's name associated with the register number displayed in register column 1807. Time column 1811 indicates the time a call was on-hook. Duration column 1813 displays the amount of time a call has been in progress. Phone number column 1815 indicates the number being called from each telephone terminal. Monitor calls in progress screen 1800 may also include additional fields indicating station ID, line number, etc.

By clicking monitor button 1817, an authorized software user may monitor live telephone conversations selectively. End monitoring button 1819 is used to end live monitoring.

Figure 19:
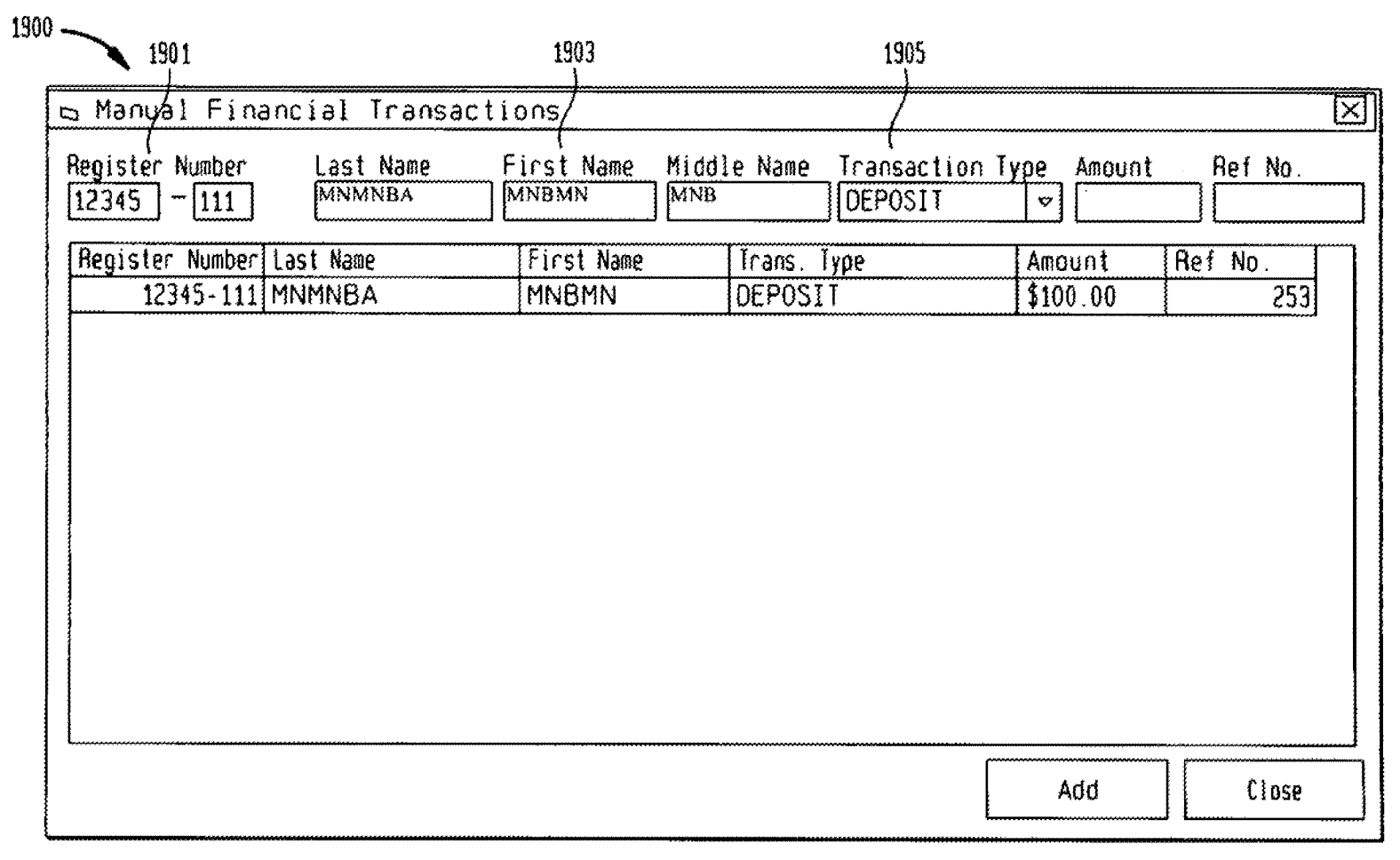

Now referring to FIG. 19, shown is an example of a manual financial transaction screen 1900. Manual financial transaction screen 1900 allows prison staff members to manually transfer funds in or out of an inmate's financial account. Register number field 1901 displays the unique eight-character number associated with each user of the call management system. Name field 1903 includes sections indicating a user's first name, last name, and middle initial.

Transaction type field 1905 indicates the type of transaction selectable from a list. The selection may be deposit, withdrawal, exception, amount of transaction, reference number, etc. Upon completing all manual transactions for a user, a manual transactions report will be generated automatically.

Manual financial transactions screen 1900 is also used to close a user's account. This is done by setting transaction type 1905 to "release". When a user is released using the manual transaction screen, the user's account status automatically changes to inactive, and assuming the user is not using the account at the time, the remaining balance is transferred to a commissary account. No further calls or transactions will be possible with this account while their status remains inactive. In addition, a record of this release will automatically be made on the user release report.

Figure 20:
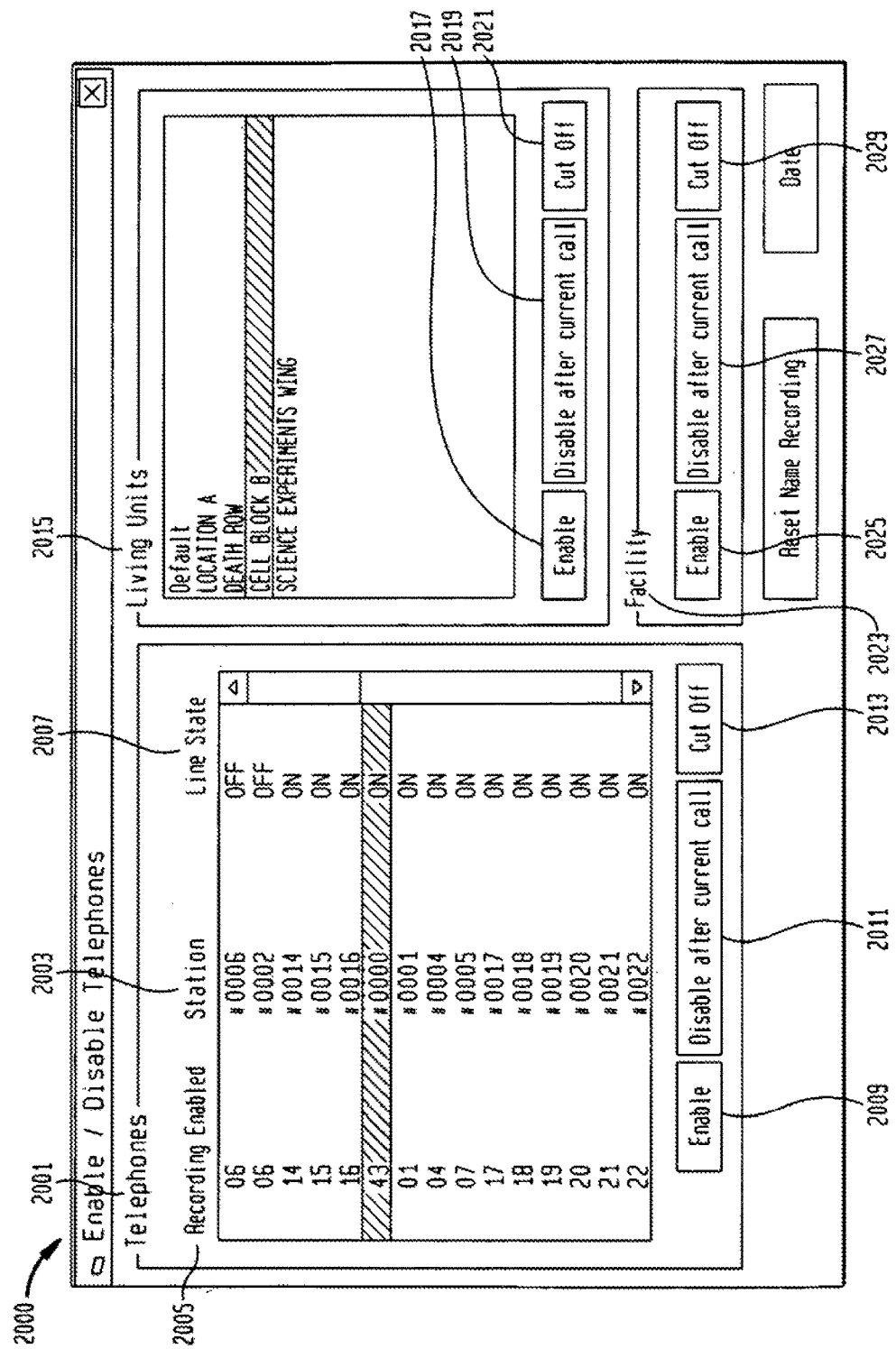
FIG. 20 depicts a sample enable/disable telephone screen for use with software contained in the call management system of the preferred embodiment of the present invention.

FIG. 20 depicts an example of enable/disable telephones screen 2000. The leftmost portion of the screen, telephone block 2001, contains three fields. Station number field 2003 indicates the number assigned to each telephone terminal. Recorder channel number field 2005 indicates the recorder channel assigned to each telephone station. Line state field 2007 indicates the hook status of each telephone station. A telephone terminal can be enabled by selecting the proper station number and choosing enable button 2009. Disable after current call button 20U is used to disable telephones after the line state status field 2007 indicates an "off" status whereas cut off button 2013 is used to disable calls currently in progress.

Enable/disable telephones screen 2000 also allows authorized users to enable/disable all calls at the living unit level or the facility level. Living units block 2015 is used to control the line state status of all phones in each living unit. Telephone terminals are enabled by choosing enable button 2017. Disable after current call button 2019 is used to disable telephones after all telephone stations are free whereas cut off button 2021 is used to disable all telephones even if calls are in progress.

To enable/disable telephones at the facility level, buttons in facility block 2023 are utilized. Telephone terminals are enabled by choosing enable button 2025. Disable after current call button 2027 is used to disable telephones after all telephone stations are free whereas cut off button 2029 is used to disable all telephones even if calls are in progress.

Figure 21:
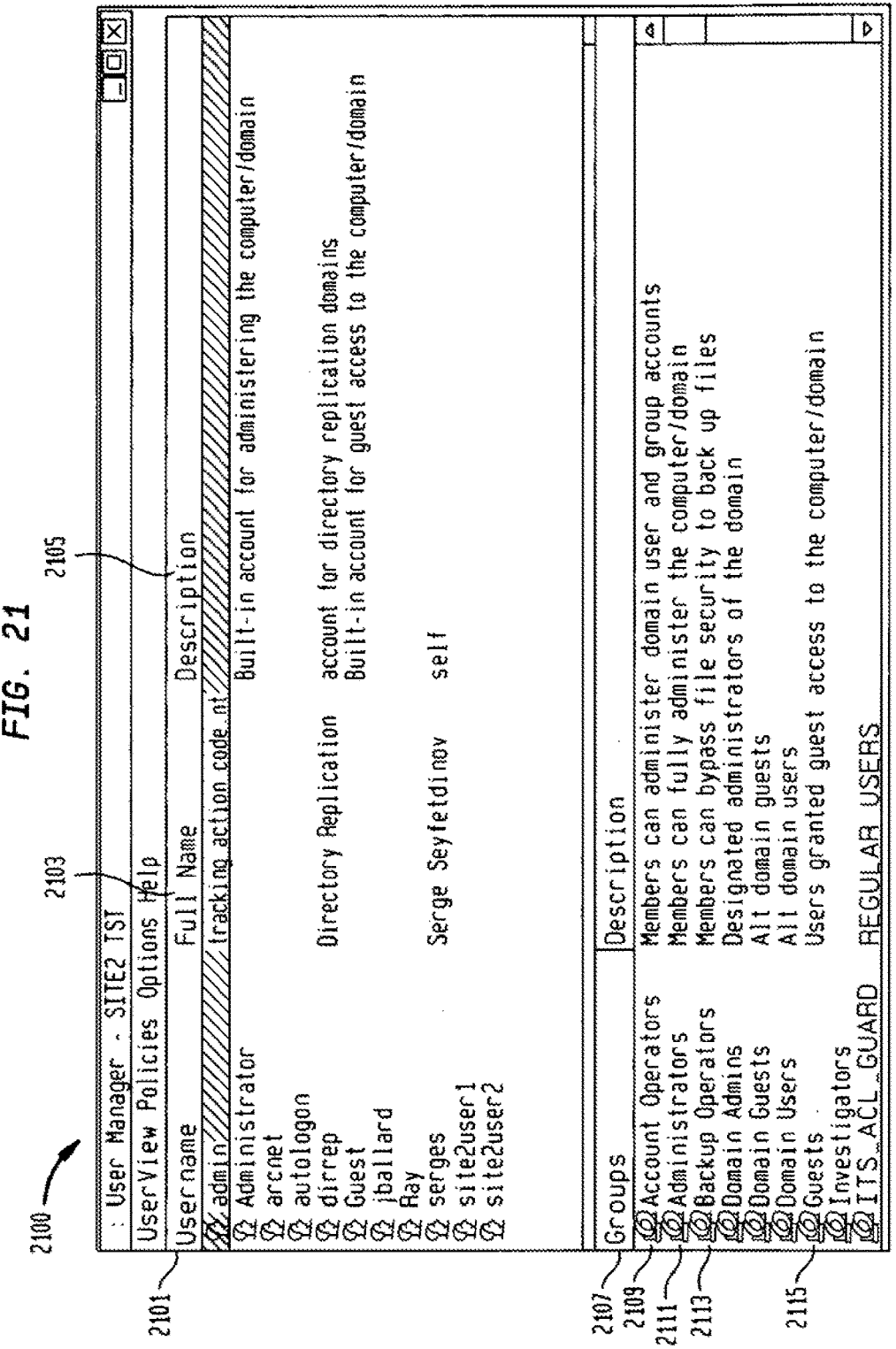
FIG. 21 depicts a sample user manager screen for use with software contained in the call management system of the preferred embodiment of the present invention.

Now referring to FIG. 21, shown is sample user manager screen 2100 which is utilized to control a self-contained application used for assigning access privileges to software users. Only authorized staff may access the telephone system. In addition, their access is limited to only those facilities for which they are responsible, unless granted increased access by a higher security level. The user administration option include a user manager and screens to set security level access and user alerts. Usemrname column 2101 indicates the different authorized users. User names typically indicate security level, such as "guest", "administrator", etc. Full name column 2103 typically displays the first, middle, and last name corresponding to each username. Description column 2105 displays a brief description associated with each username.

Different lists of users are accessed from groups block 2107, typically located at 23 the bottom of the screen. User groups may include, but are not limited to, account operators 2109, administrators 2111, backup operators 2113, and guests 2115. Each user group may additionally be given a selection. User security profiles and groups can be modified by double clicking on the desired user or group.

Figure 22:
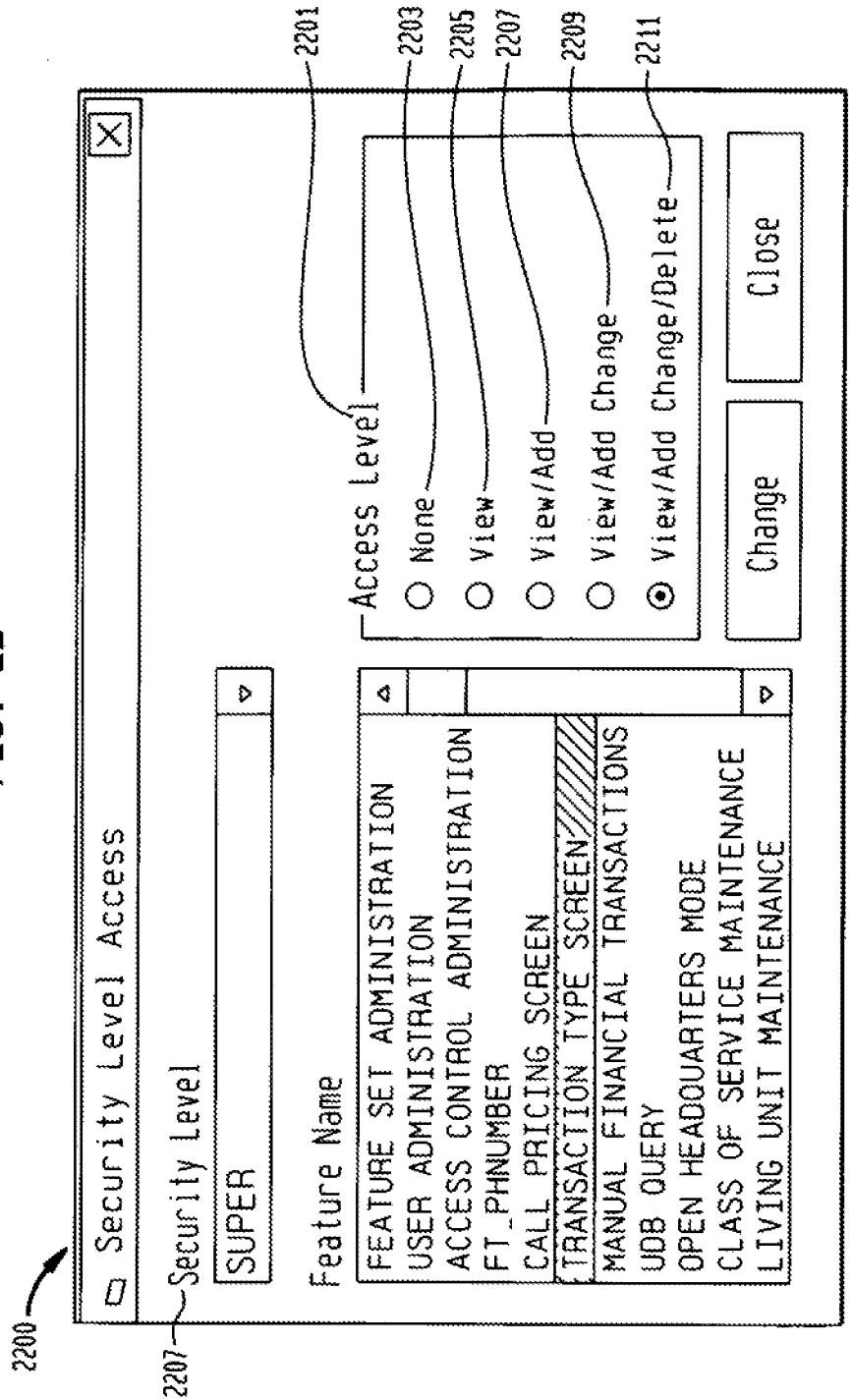
FIG. 22 depicts a sample security level access screen for use with software contained in the call management system of the preferred embodiment of the present invention.

Referring next to FIG. 22, depicted a sample security level access screen 2200, which is available from the main menu of the user manager software. Security level field 2207 determines how much access a prison staff member has to work with information and modify settings in the call management system. For each security level, the access capabilities may be set for each feature, selectable from access level block 2201. If none selection 2203 is selected, a user is denied access to the system. The view selection 2205 allows users with this security level to only view user profiles and other features of the system. The "view, add" selection 2207 allows users with this security level the added ability to add new phone numbers to the software. The "view, add, change" selection 2209 allows users with this security level the added ability to change settings within system. The highest level of access afforded to users is granted by selecting the "view, add, change, delete" selection 2211 which allows full control over the software. Security level field 2207 includes selections such as monitor, unit operator, investigative, technician, supervisor, COF operative, etc.

Figure 23:
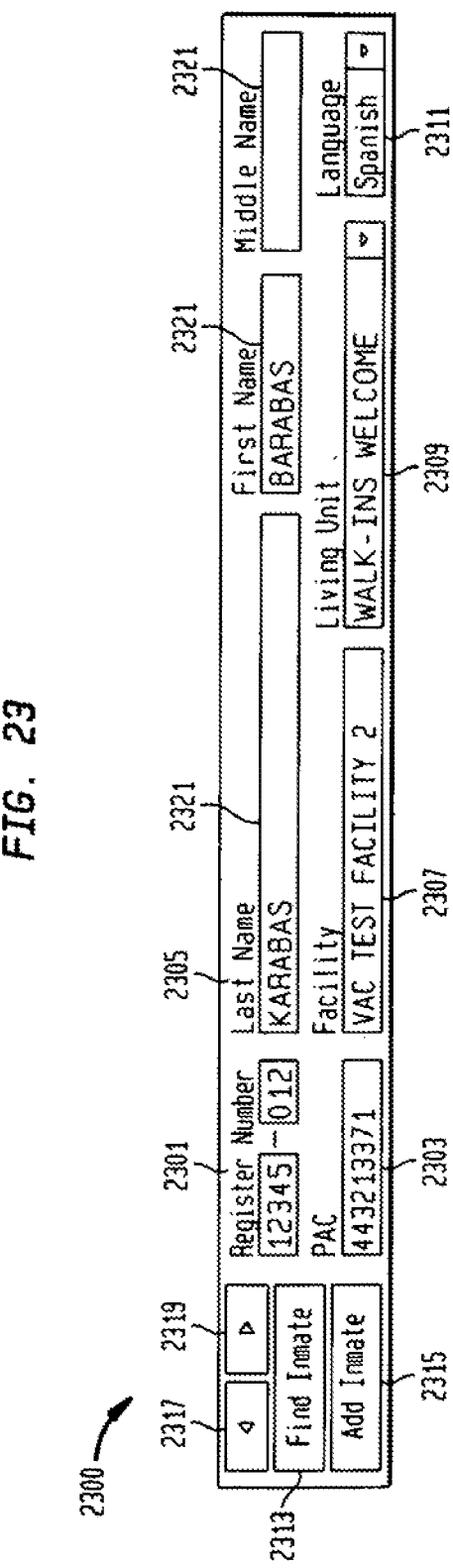
FIG. 23 depicts a sample user information screen for use with software contained in the call management system of the preferred embodiment of the present invention.

Now referring to FIG. 23, shown is a sample user information screen 2300 displayed at the top of every page of an inmate's account information. Users establish an account to have funds for telephone transactions. In order for a user to place a direct dialed call, a user must have sufficient funds in an account to pay for at least a three-minute call. For example, in a correctional facility, this account is separate from the user's commissary account, which is the inmate's general prison spending account. However, a user may transfer money from their commissary account into a user-specific account. Alternatively, a prison staff member can perform a manual transaction. At no time will an account balance be allowed to drop below zero.

A user must have a system account established in order to make telephone calls from a specific facility. This information will be stored on the site server which may be integral or remote from the call system architecture. When an inmate is transferred from one facility to another, only the inmate's account information, COS, and telephone lists are transferred to that facility. However, previous information may remain in an archived database or other storage system.

Register number field 2301 contains an eight-digit number unique to each user. Although eight digits are utilized for the present invention, numerous character strings may be utilized depending on the number of intended users. A name field lists the user's first, last, and middle name. Facility field 2307 indicates the facility at which the user is located. Living unit field 2309 indicates the living unit in which a user is located. A language field 2311 is used to select the language of voice prompts used by the call system. Personal identification number field 2303 displays the user's PIN used to access the call system. The PIN is used in conjunction with biometric authentication and/or RF authentication. For example, as discussed with respect to FIGS. 2A and 2B, the system of the present invention may implement a system of speaker independent voice recognition and speaker dependent voice identification to verify a user. Such voice processing can be implemented with off-the shelf hardware or software. The PIN is a confidential number. Should the number be lost or stolen, a new PIN should be assigned as soon as possible to prevent fraud. A unique PIN will be selected from a national pool of numbers and assigned to the user.

In the example of a penitentiary, a find inmate button 2313 allows access to an inmate's account from any page on the inmate account information screen. User accounts can also be added from this screen via the Add Inmate (or Add User in other embodiments) button 2315. Using the ">" button 2317 and "<" button 2319 buttons allows for easy navigation through inmate profiles.

Figure 24:
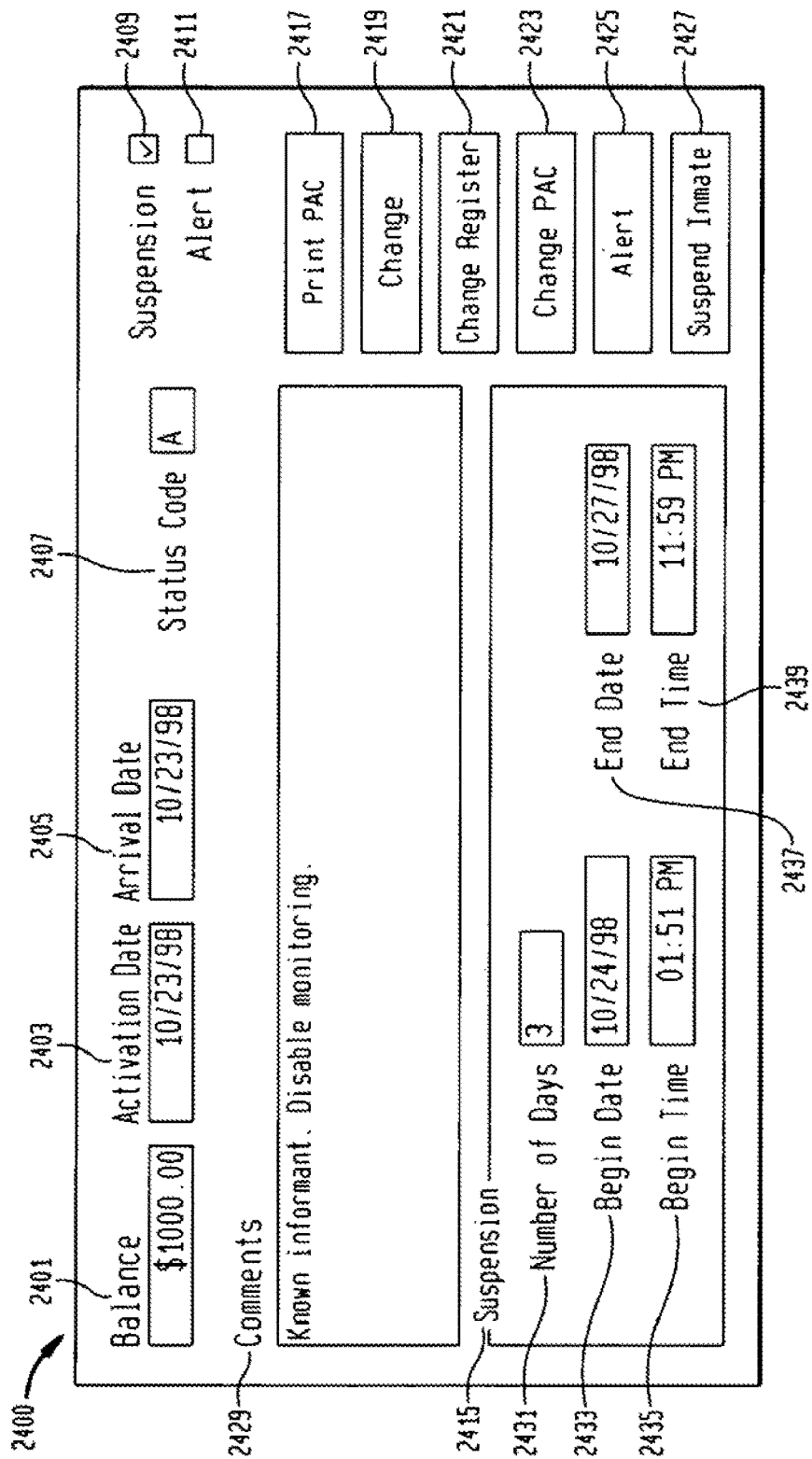
FIG. 24 depicts a sample account screen for use with software contained in the call management system of the preferred embodiment of the present invention.

FIG. 24 depicts a sample account screen 2400 which is used to monitor a user's account balance and suspension status. A user's financial account is used to pay for direct dialed calls from their account. This is separate from any money a user may have in their commissary account. When placing a direct dialed call, a user must have a large enough balance, displayed in balance field 2401, to pay for at least a three minute call, or they will be informed that they have insufficient funds to place the call.

The account activation date field 2403 indicates the date a user's account was originally created. It is supplied automatically by the program and cannot be modified. Financial and call records for an inmate should be available back to this date. In the present example, the most recent data is kept locally on the site server, unless the inmate had been transferred within that time, in which case only the data since the transfer is kept.

The date of arrival field 2405 displays the date that an inmate arrived at their current facility. The date of arrival is automatically generated when an inmate is transferred to a new facility.

Inmates may be assigned a status code, displayed in status code field 2407, to help separate them into various classifications. The status code is a single letter code from A-Y. The definitions for these codes are established by the central site server. In the present embodiment, a status code 'Z' indicates that the inmate has been released, and their account is inactive. Status 'Z' cannot be set manually. It is done automatically once an inmate has been released using the manual transaction screen. An account with a status code 'Z' cannot make calls or process transactions from that facility.

Suspension field 2409 indicates whether or not a user's calling privileges are suspended. Similarly, alert field 2411 indicates a user's current alert status. Comments field 2413 can be used to display any information regarding a user's financial, alert, or suspension status.

Buttons located in the lower right corner of account screen 2400 are used to modify a number of user settings. Print PAC button 2417 is used to print a user's current PIN or other access number. Change button 2419 is used to modify data such as user name, living unit, user language preference, status code, and comments. Change register button 2421 allows authorized personnel to change a user's identification number. Change PAC button 2423 is used to modify a user's current PIN. Alert button 2425 toggles alert field 2411. Finally, suspend inmate button 2427 is used to toggle suspension field 2409.

The prison staff has the capacity to temporarily suspend an inmate's calling privileges using suspension block 2429. Number of days field 2431 is used to set the length of a user's suspension. Begin date field 2433 and begin time field 2435 are used to input the respective date and time that a user's suspension is to begin. Similarly, end date field 2437 and end time field 2439 are used to input the respective time and date a suspension is to end. Information regarding a user's last suspension remains displayed in suspension block 2429 even after the suspension has expired.

FIG. 25 displays a sample financial history screen 2500, which includes all call system financial transactions for the inmate's account during the year and month selected in year field 2502 and month field 2504. A date column 2501 displays the date of each financial transaction. Time column 2503 displays the hour at which each financial transaction occurred. Type column 2505 indicates the type of each transaction (e.g., deposit, withdraw, refund, etc.). Amount column 2507 displays the monetary amount involved in each financial transaction. Balance field 2509 displays the resulting balance after each financial transaction has occurred. Facility column 2511 displays the facility location at which the transaction occurred. Reference number column 2513 indicates the specific reference number assigned to each financial transaction. User column 2515 displays the system user that authorized each financial transaction.

Financial transaction screen 2500 also includes a number of buttons located in the upper right hand corner. Display button 2517 refreshes the financial transaction list for the month and year selected. Display button 2517 must be pressed each time the year and date are changed. Current month button 2519 brings up financial transaction data for the current month. Sort order button 2521 determines the order in which the information will be displayed. In this embodiment, the choices are date/time (ascending or descending), or transaction type/date/time (ascending or descending). Refund button 2523 is used to perform a direct dial call refund.

FIG. 26 displays a sample call records screen 2600 which includes everything about each call made or attempted, and whether or not the call was successful. The range of dates listed is determined by year field 2601 and month field 2603.

Date column 2605 displays the date of each financial transaction. Time column 2607 displays the hour at which each financial transaction occurred. Dialed digits column 2609 indicates the sequence of digits used during each phone call. Duration column 2611 displays the time in minutes of each phone call and charge column 2613 indicates the resulting cost of the call. Charge type column 2615 indicates the calling method used for each telephone call (e.g., direct call, collect call, international, etc.). Call result column 2617 displays the appropriate completion code for each call. A completion code is chosen from a pre-assigned code list indicating possible outcomes of telephone calls. Recorder column 2619 displays the recorder used for each call. Alter type column 2621 indicates the type of alert triggered, if any.

Figure 27:
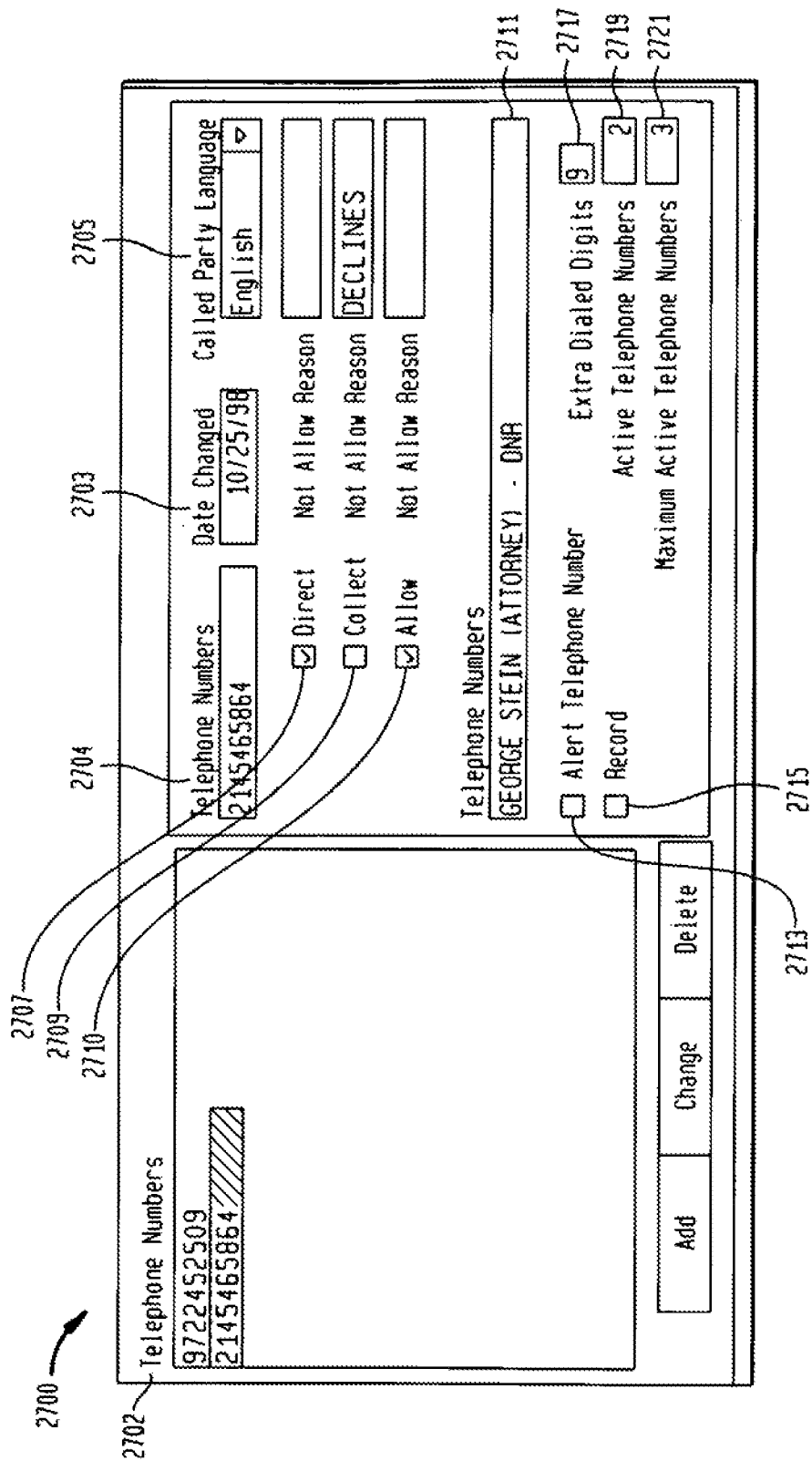
FIG. 27 depicts a sample telephone list screen for use with software contained in the call management system of the preferred embodiment of the present invention.

Displayed in FIG. 27 is a sample telephone list screen 2700. A user's list of telephone numbers is displayed in telephone number list 2702. By selecting a particular telephone number from this list, its associated information (i.e., name of party, whether to record those calls, etc.) can be edited using options located on the right hand portion of telephone list screen 2700. Telephone number field 2704 is used to change the digits in each telephone number. Date changed field 2703 indicates the last time telephone number information was modified. Called party language field 2705 indicates the language of voice prompts used to interface the called party. Direct dial field 2707 is used to select if direct dial calls are allowed for the telephone number listed in telephone number field 2704. Collect call field 2709 is used to select if collect calls are allowed. Allow field 2710 is used to set the telephone number to a user's allow list. Comments field 2711 is utilized to store any extra information concerning the called party. Alert telephone number field 2713 is used to toggle an alert flag on the telephone number. Record field 2715 is used to indicate if telephone conversations are to be recorded. Extra dialed digits field 2717 indicates the number of extra digits allowed after a call is connected. Active telephone numbers field 2719 displays the number of telephone numbers currently on a user's active list. Maximum telephone numbers field 2721 displays the maximum amount of telephone numbers that may be on a user's list at any given time.

Figure 28:
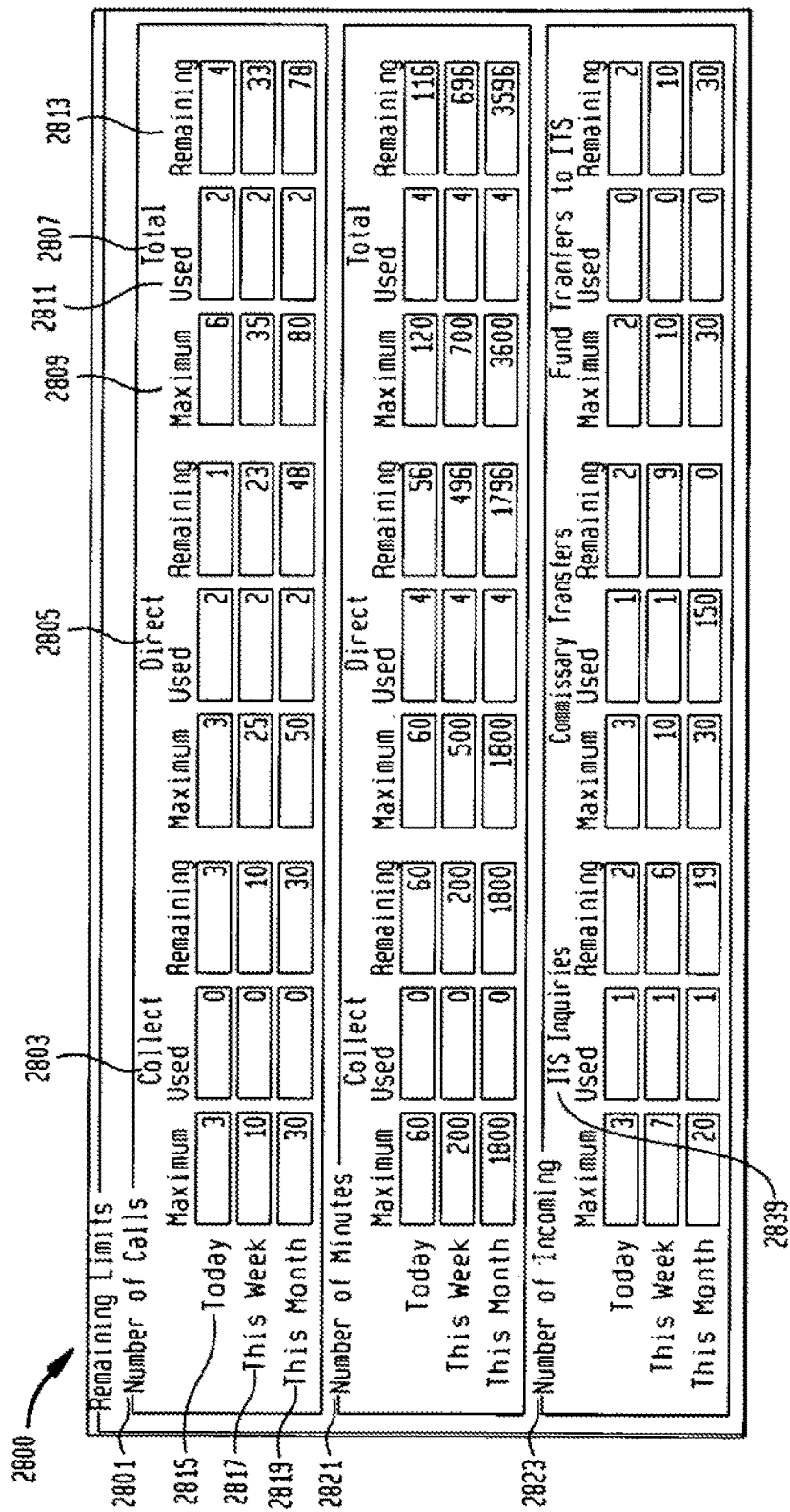
FIG. 28 depicts a sample call limit status screen for use with software contained in the call management system of the preferred embodiment of the present invention.

Shown in FIG. 28 is a sample call limit status screen 2800 containing three separate sections. The number of calls block 2801 displays information relating to the number of calls placed. Number of calls block 2801 is divided into a collect section 2803, direct section 2805, and total section 2807. For each section, there is maximum column 2809, used column 2811, and a remaining column 2813. Additionally, each section contains today row 2815, "this week" row 2817, and "this month" row 2819. The intersection of these rows in columns forms nine fields in each section for a total of twenty-seven fields in each block. The additional blocks are a number of minutes block 2821 and a number of inquiries block 2823.

Figure 29:
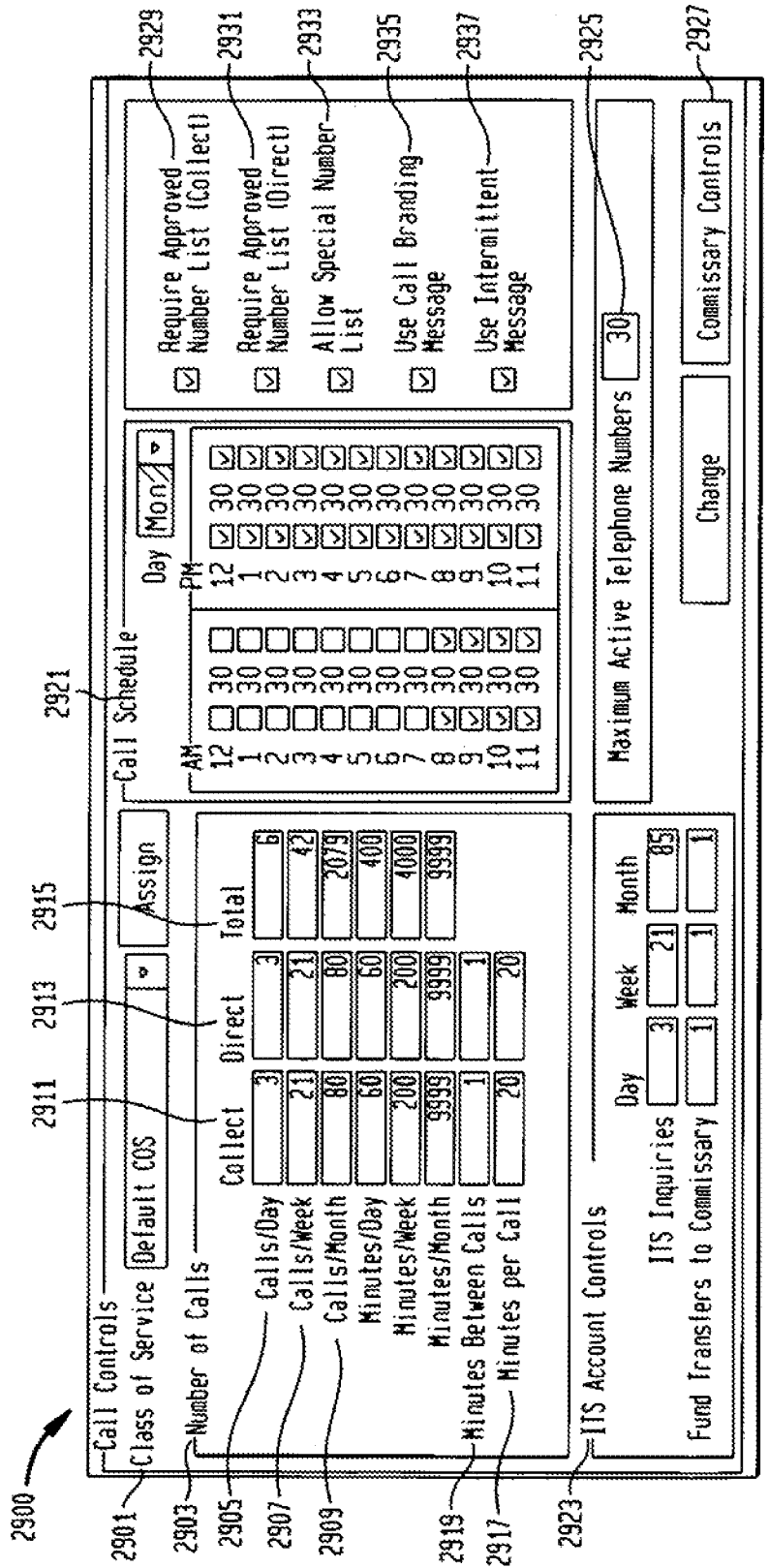
FIG. 29 depicts a sample access control screen for use with software contained in the call management system of the preferred embodiment of the present invention.

FIG. 29 depicts a sample access control screen 2900 in which the calling limits and permissions are set, usually by assigning a predefined COS to the inmate. Initially, the COS assigned to an inmate account is the default COS for the living unit they have been assigned to. In addition, all the settings and permissions may be customized for the inmate manually.

Call access control block 2903 contains collect column 2911, direct call column 2913, and total column 2915. Corresponding to these columns are a number of rows. At the intersection of the rows and columns a number of fields are formed. Calls/Day row 2905 is used to enter the number of collect, debit, and total calls allowed per day. Calls/Week row 2907 is used to enter the number of calls allowed per week. Calls/Month row 2909 is used to enter the number of calls allowed per month. A minutes between calls row 2919 indicates the amount of time that must lapse between calls before another can be made. Minutes per call row 2917 is used to enter the maximum duration allowed for each telephone call.

Call schedule block 2921 determines when the inmate may use the telephone system. For each day of the week, selected from the day drop down list, there is a checkbox for each half hour period of time. If checked, calls are allowed to begin during that half-hour. For instance, if 9:30 PM is checked, calls can begin anytime from 9:30-9:59:59 PM.

ITS access control settings block 2923 determine how many times inmates may perform an inquiry for each day, week, or month.

Maximum active telephone numbers field 2925 limits the number of telephone numbers on the inmate's approved list. Commissary controls button 2927 switches screens to allow control of when and how often inmates may access the commissary system and transfer funds.

A number of check box fields are also located on this screen, including require approved number list (collect) field 2929, require approved number list (direct) box 2931, allow special number list 2933, use call branding message 2935, and use intermittent message 2937.

Branding allows a pre-recorded message to be played for the called party at the beginning of every call to announce, "This call is from a Colorado Correctional Facility." This message can be set for the individual inmate, a living unit, or all inmates at a facility. Call branding may be turned on or off at the discretion of the prison staff.

Much like call branding, intermittent messages play the pre-recorded message "This call is from a Colorado Correctional Facility" throughout the call. How often the message plays is randomly determined, within a set minimum and maximum duration between plays.

The Shadow software provides the capability to digitally record, store, playback and execute a possible keyword search. Shadow resides on a separate site server providing flexibility in implementation and sizing of the system. It can simultaneously record conversations from all telephones installed at a site regardless of the size of the site. As an integrated part of the system, the Shadow software is completely transparent to the user. An intuitive user interface is provided for playback of the conversation.

The call records screen, (FIG. 26), is used to access the Shadow software. Each call record can be played by double-clicking on the desired call record. This example call detail screen is shown in FIG. 30. Call detail screen 3000 contains all details of the selected call. Telephone number field 3001 indicates the number called. Date/time field 3003 indicates the date and time the call commenced. Call result field 3005 displays the final status of completed call. Facility field 3007 indicates the facility from which the call was placed. Telephone location field 3009 displays the living unit from which the call was placed. Station ID field 3011 indicates the particular telephone terminal used to place the call. Destination field 3013 indicates the trunk line used for the call. Call type field 3015 displays the method employed for placing the call. Carrier field 3017 displays the long distance carrier used for the call. City and state field 3019 indicates the location of the placed call. Extra dialed digits field 3021 indicates if extra dialed digits are allowed after a call has been connected. Call details screen 3000 also contains three-way call field 3023 used to enable conferencing calling. Clicking play button 3025 allows authorized users access to the shadow software.

Figure 31:
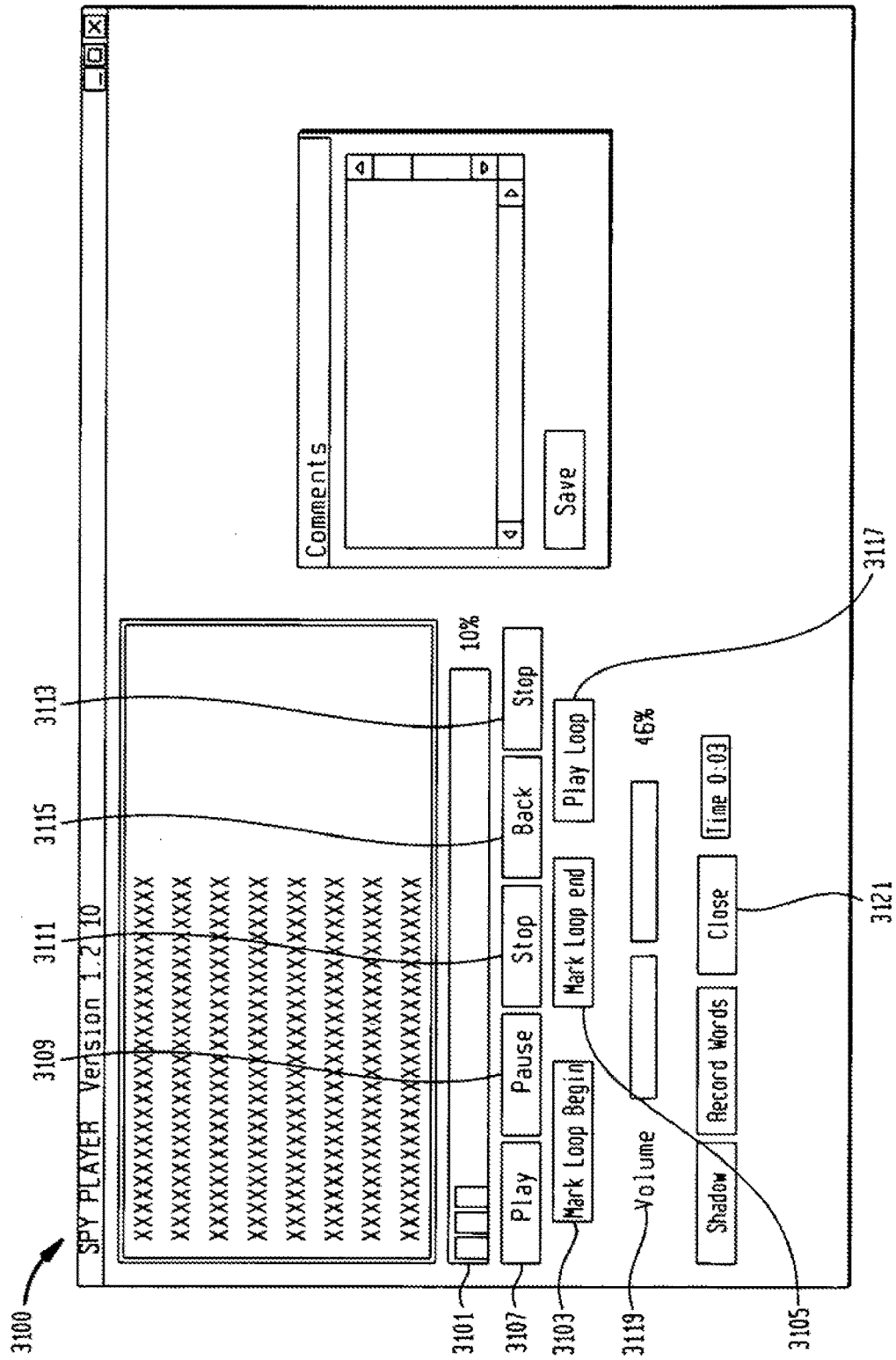
FIG. 31 depicts a sample spy player screen for use with software contained in the call management system of the preferred embodiment of the present invention.

FIG. 31 shows an example spy player screen used for controlling the shadow hardware. The top half of the screen provides the user with full control of the software. Percentage bar 3101 at the top of the lower half permits the user to see how far into the conversation he has progressed. This information can be used in conjunction with mark loop begin button 3103 and mark loop end button 3105.

Play button 3107, pause button 3109, and stop button 3111 operate in the typical fashion. Step button 3113 permits users to "fast forward" in the recorded conversation to any point. Playback is automatically resumed when the step button is released. Back button 3115 is used in a similar manner. Mark loop begin button 3103 marks the beginning of a selected segment of the recorded conversation for repeated playback. This feature is extremely useful when a segment of the recorded conversation is not readily understood. Mark loop end button 3105 marks the end of a selected segment of the recorded conversation for repeated playback. This button is grayed out until mark loop begin button 3103 is activated.

Play loop button 3117 is used to replay the portion of the conversation from the mark loop begin to the mark loop end positions. Repeated playback continues until stop button 3111 is depressed. The button is grayed out until mark loop begin 3103 button is activated. Volume bar 3119 permits users to adjust the volume to a desired level. Close button 3121 closes the shadow button and returns the user to the call detail screen (as shown in FIG. 30).

Figure 32:
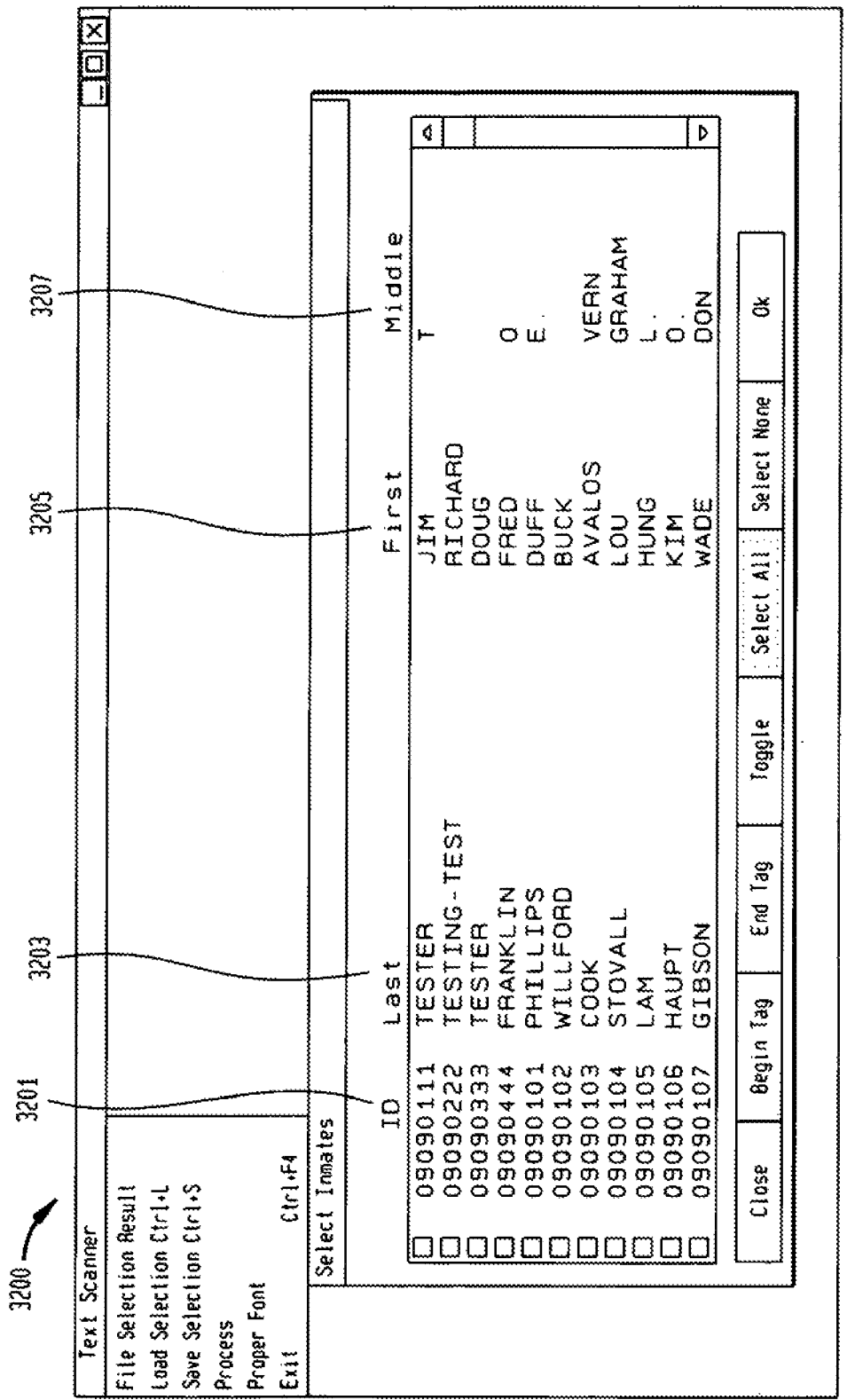
FIG. 32 depicts a sample "text scanner" selection screen for use with software contained in the call management system of the preferential embodiment of the present invention.

The Shadow software also incorporates a text scan, which can be used to find a particular call for audio review. A site to search is selected from a drop down list accessed from the main screen of the software. This brings up a text scanner selection screen shown in FIG. 32. Text scanner selection screen 3200 contains a number of columns. Resident ID number column 3201 displays the ID number of each inmate. Last name column 3203 displays the last name of the user. Similarly, first name column 3205 and middle name column 3207 contain the first and middle name of the user, respectively.

After the desired criteria have been chosen from this list, the software executes the text scan and query result screen will appear, as shown in FIG. 33. From query result screen 3300, the desired call can be selected and played back using the Shadow software. Resident ID number column 3201 displays the ID number of each inmate. Date column 3303 displays the date the call was made. Time column 3305 indicates the time at which a call commences. Destination ANI column 3307 displays the sequence of digits dialed. Duration column 3309 displays the time duration of a completed call. Station name column 3311 displays the station identification number of the phone used to place the call.

Figure 34:
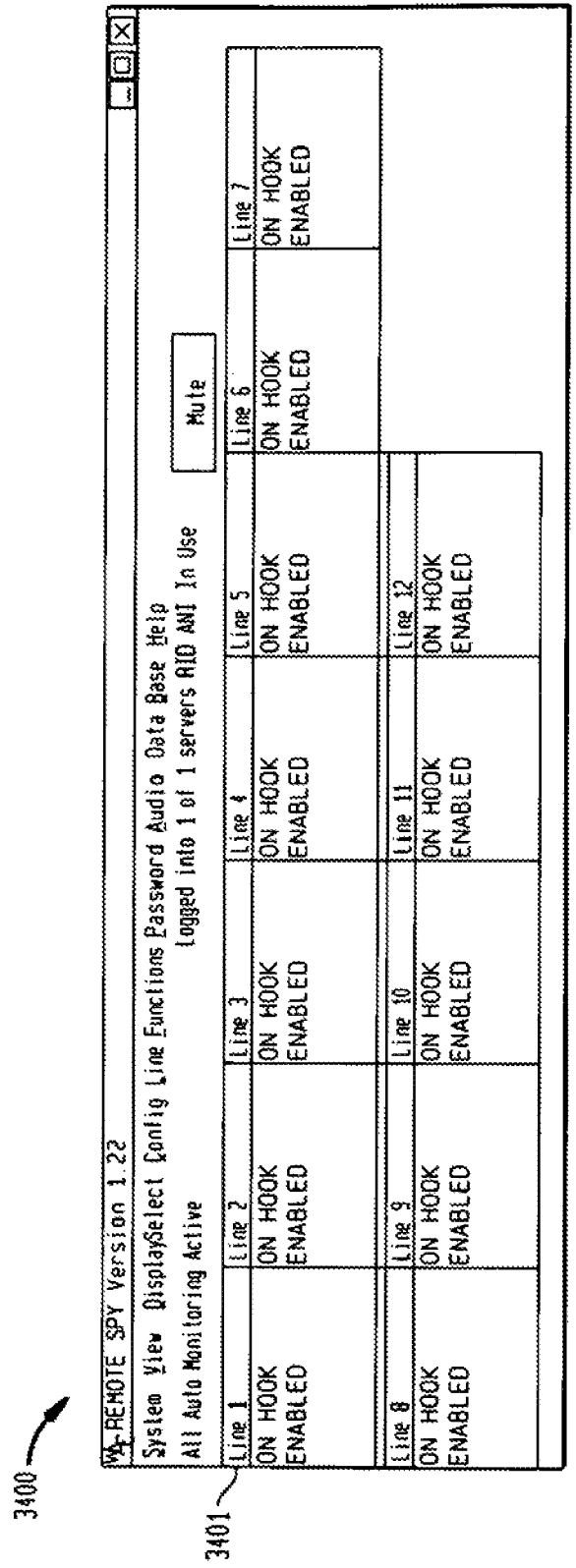
FIG. 34 depicts a sample remote spy screen for use with software contained in the call management system of the preferred embodiment of the present invention.

FIG. 34 depicts sample remote spy screen 3400 used to interface the shadow software. It can be used to remotely view all calls in progress. Each telephone line is displayed with its associated status in status box 3401. By double Clicking on any telephone line, users can access the details (FIG. 30) of the call showing telephone number of called party, inmate RID, line out, first name, last name, screen block, line enabled or disabled, current status of line, off hook time, and on hook time. For each telephone call, a user can access buttons for force hang up, host record; or filename, start monitoring, start local recording, local record file name, or close. Users may also listen to real time telephone conversations using this piece of the shadow software.

The call system allows for quick and easy tabulation of data. Every report contains at a minimum general report capabilities. Reports may either be generated automatically at certain times or under certain conditions, or printed upon demand by prison staff members with appropriate user level access. Reports may be generated for one facility or a combination of facilities, depending upon the requesting user's security level.

All reports contain, at a minimum, time, terminal making request, parameters of the report, number of pages, report heading, end of report footer, report heading on each page, report title on each page, identified of the staff member creating the report. In the present example, the header on each page includes the prison name, report name, data and time of the report, page number, and field headings. The footer, contained at the end of the report, contains total for all columns containing dollar values, total count of inmates if the report contains inmate information, and total call counts or total call duration if report includes this information.

Various reports have different selection criteria and parameters to be defined before running the report. Many will prompt the user for a start date/time and an end date/time and an end date/time. Others require the user to select individual or multiple records at a time. Some reports utilize 'wizards', such as the telephone wizard, that allow the use of pre-saved selections. All reports can also be saved for later use.

An example report is shown in FIG. 35 displaying an account telephone number list report. Account telephone number list report 3500 displays all the telephone numbers on the allowed list for one or more inmates. For each inmate, the report displays inmate DOC number 3501, inmate name 3503, and facility code 3505. The report additionally contains phone number column 3507, collect calls column (yes/no) 3509, accept direct calls column (yes/no) 3511, recorder on column (yes/no) 3513, number allowed column (yes/no) 3515, called party language column 3517, date number added to their list 3519, and total number of telephone numbers on the list 3521. Similar reports for call and financial statistics may be compiled according to their desired use.

Biometric and RF Authentication Software

Separate software controls the biometric and RF authentication. The biometric portion of the software will be contained first.

As discussed with respect to FIG. 2B, upon entering an institution, each potential telephone user has a telephone account setup. If biometric authentication is being utilized by the institution, the required information is scanned using a biometric scanner. This information is relayed through the DIS and stored on the site server along with the user's PIN and other authentication information. When a user attempts to access the telephone system at a later time, the system will ask the user to supply the same biometric information to the scanner located at the telephone. This information is compared to the biometric information already located on the site server using complicated algorithms to process the digitized data. If the supplied information matches the stored information, the user is authenticated and can use the call system call management system.

The biometric scanner may be a retinal scanner, fingerprint scanner, body heat sensor, or any other like device.

Such scanners typically include means of digitizing the information so it is readily available to the DIS.

As discussed with respect to FIG. 2B, the system preferably uses voice recognition and identification to further ensure the correct identity of a user who wishes to access the system. When the user enters the system for the first time (i.e., subscribes) he or she is required to provide a speech sample. Speaker independent voice recognition is used to verify the sample is significant (i.e., not just a whistle, cough, sigh, etc.). Then, during all subsequent accesses, the user is required to provide the same speech sample with the correct PIN. For example, in one embodiment, the user is required to state his or her name each time the user wishes to place a telephone call. The use of a speech sample provides an extra level of security in the system of the present invention. It is well known that PINS are easy to steal, guess or to obtain via coercion. Voiceprint identification is also generally less cumbersome to the user than other methods of biometric identification.

The called party may also be voice authenticated each time a user places a call (e.g., a record of voice prints for the called family members may be established). This provides additional security because it ensures that the user is not communicating with an unauthorized party. The biometric information provided by the called party can also be used for third party call detection. By continuously sampling voice data from the telephone conversation, the biometric software can be used to detect if a third party or an unauthorized person has spoken. Upon third party detection, the call can be disconnected and/or authorities may be notified. This will cause an alert in the inmate's profile.

The biometric authentication software can easily be extended for use with telephone cards. Upon purchasing a telephone card with limited or unlimited debit, the user provides voice initial voice data for future voice authentication. This may occur in a number of ways. For example, the user may be required to provide voice information at the institution that the telephone debit card was purchased, such as a supermarket or convenience store. The voice information may also be provided the first time that a user calls the access number for the debit card. A voice prompt asks the user to state and repeat their name. Additionally, the telephone number from which the user is calling from may be asked for and entered via DTMF tones or recording based on the ANI data. The telephone system may then hang up the line and call back the number provided by the user and ask for voice authentication utilizing the information previously provided. Upon authentication, the user does not have to repeat the initial voice supplication. If a user attempts to use the purchased telephone debit account again, the user only has to supply voice authentication and/or an account or PIN. In this way, the user does not have to carry the telephone card to access the telephone system and need only remember the telephone access number. This authentication process can additionally be used with prepaid cellular telephones.

A similar authentication process may also be used to access an internet telephone account, or any other secure internet information. The person simply uses the microphone attached to their computer to provide the voice authentication instead of the telephone handset. This information can be transmitted via the internet to the server containing the stored biometric data and be used to voice authenticate the user.

The voice database concept may be extended for use on a PSTN. Each user of the public telephone network would only be granted access if the user's name is in the database. The voice database may also be used to limit telephone access. For example, a convicted criminal would be blocked from ever calling his previous victims. Teenagers may also be blocked from accessing "1-900" numbers and the like.

A national voice database may also be used to track wanted criminals. For example, if a wanted criminal or suspect ordered a pizza from a local pizzeria, biometric software, located on the same server as the voice database, could recognize the calling party as the wanted criminal. Authorities would then be alerted that the fugitive has been identified. Since the called number is known, authorities already have a means of narrowing the search field for the criminal. Authorities may then call the pizzeria and inquire about previously placed orders. This would provide them with a list of possible locations that the criminal may be located. Furthermore, if voice recognition is also in the capability of the biometric software, the food order of the calling party may be ascertained. Authorities could then inquire who placed that specific order. Speech recognition capability may additionally allow the address of the calling party to be located without ever having to call the pizzeria because a delivery address or telephone callback number is typically provided when placing a food order. Once the suspect is located, the suspect can easily be apprehended. This technology may also be used to help apprehend criminals who steal any device interfaced with a telephone network, public or private. Such devices include, but are not limited to, cellular telephones, wireless internet appliances, and laptops. Whenever the criminal attempts to use the stolen device, a voice print is automatically recognized by the voice database as not being an authorized user of that device. The proper authorities could then be alerted.

The RF authentication portion of the software operates in a similar fashion. When a user picks up the telephone, the RF emitter is activated. The signal is reflected by a band the user wears and the reflected signal is received by the RF sensor. Using this information, the RF software determines the distance of the inmate from the telephone and the user's uniquely encoded RF frequency. This is done using complex algorithms known to one skilled in this particular art. If the user is not a valid user of the call system, the prison authorities are notified at which facility and station ID the violation occurred. If the user is a valid user, the supplied PIN and/or biometric information are also authenticated. The user is allowed access to the system only if the information supplied is valid and agrees with the other authentication method utilized.

Figure 36:
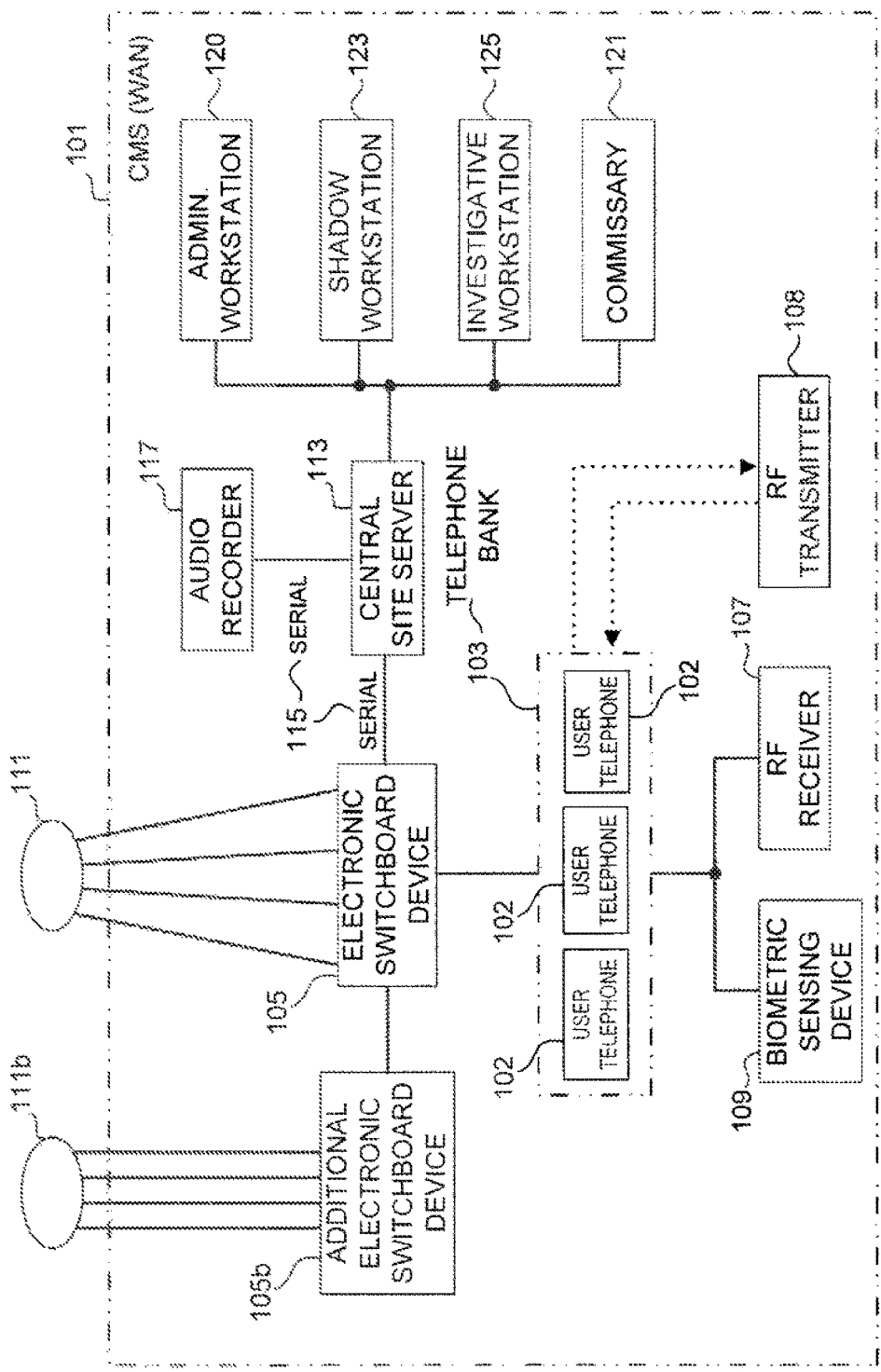
FIG. 36 depicts a schematic view of an alternate embodiment of the present invention wherein a second electronic switchboard device is connected in parallel within the call management system to handle additional trunk line capacity and overflow.

Referring next to FIG. 36, shown is an alternative embodiment of call management system 101 configured to operate in a WAN (Wide area Network). A plurality of user telephones 102 (wherein the actual number depending on the desired capacity of the institution call system) are incorporated into telephone bank 103 and are connected to electronic switchboard device 105. It is preferred that telephone bank 103 may be centrally located within a facility to allow for centralized monitoring. However, it is foreseeable that telephone bank 103 may be located at a multitude of locations internal or external to a facility. Each user telephone 102 is equipped with biometric sensing device 109, such as a retinal scanner, fingerprint reader, etc., or any combination of biometric devices, so that the acquired biometric data can be used for user authentication. Alternatively, for efficiency, a single biometric sensing device 109 may be employed for a multitude of user telephones 102. Additionally, each telephone may incorporate RF receiver 107 and RF transmitter 108 installed to provide RF signals for authentication purposes. In this scenario, it is foreseeable that each user may be required to wear RF transmitter 108 device to be received at RF receiver 107 which may be integral (or remote to) telephone bank 103. Each RF transmitter 108 is uniquely encoded to a specific authorized user. The encoded signal for RF transmitter 108 may be altered on an intermittent basis depending on the security desired at the institution. RF transmitter 108 may be incorporated into a wristband, ankle band, or any other like device. It is foreseeable that RF transmitter 108 may be semi-permanently or permanently attached to a user's person in any manner currently known. Electronic switchboard device 105 regulates calls and connects them to proper outgoing trunk line 111. Trunk line 111 may consist of a multitude of connections to any number of local, long distance, or international telephone service providers. The number of trunk lines 111 depends on the outgoing capacity desired by the institution. In addition, trunk lines 111 may be analog, digital, or any other type of trunk lines not yet contemplated. Electronic switchboard device 105 also further incorporates an integrated channel bank, allowing calls to be processed over either analog or digital trunks as required by call management system 101. Specifically, when one trunk line 111 is occupied and handling an outgoing communication, electronic switchboard device 105 automatically accesses an alternate trunk line to handle the outgoing communication. If all trunk lines 111 on the system are in use, the call may be routed to an alternate system as a busy signal (not depicted). For example, electronic switchboard device 105 may be interconnected to another electronic switchboard device 105 which may be located within the institution or at a geographically distinct location. In this embodiment, electronic switchboard device 105 is connected to an additional series of trunk lines 111. The electronic switchboard device 105 routes calls to electronic switchboard device 105 if call volume is high. A cross point switch integrated into electronic switchboard device 105 may also accomplish this routing.

Multiple processors may also be incorporated into the architecture. This allows call processing even after component failure. The architecture also provides for a sharing of the load between processors, which eliminates system overload during extremely busy periods.

Additionally, electronic switchboard device 105 performs the voice prompts heard by the user and the recipient of the call allowing the parties to respond to the menu selections. Electronic switchboard device 105 also tests outgoing trunk lines as calls are placed and digitizes telephone audio for recording and/or biometric voice identification. If no dial tone is present, trunk line 111 is taken out of service for a pre-programmed amount of time for maintenance. These capabilities are pre-programmed into the device's firmware. However, it is foreseeable that software and software upgrades may provide these services in addition to other services useful in the present invention.

A central site server 113 interfaces within call management system 101 via first serial port 115. In the preferred embodiment of the present invention, an RS-232 serial port is employed for the interference connection. However, it is foreseeable that other types of serial ports 115 commonly known in the art may be utilized. Serial port 115 may also be comprised of a direct hardware connection or may consist of a series of ports and connecting means commonly known in the art for connecting electronic devices. Serial port 115 is designed to allow firmware driven systems, such as electronic switchboard device 105, to interface with software-based systems, such as a PC designed system operating as a site server. All user and telephone call information is routed through central site server 113. At central site server 113, user call information is digitized for efficient data transfer and efficient record keeping. Central site server 113 stores at a minimum each user's financial transaction data. It is preferred that central site server 113 also stores the digitized audio used for voice prompts as well as each user's call restrictions, PIN, biometric verification data, etc. However, depending on the memory requirements, numerous site servers may be employed. It is foreseeable that older archived data may also be stored on an integral or a remote computer system database (not shown) or kept on additional storage devices on central site server 113.

Connected to central site server 113 via a second serial port 115 is audio recorder 117. In the preferred embodiment of the present invention, an RS-232 serial port is employed for the interference connection. However, it is foreseeable that other types of serial ports 115 commonly known in the art may be utilized. Serial port 115 may also be comprised of a direct hardware connection or may consist of a series of ports and connecting means commonly known in the art for connecting electronic devices. Audio recorder 117 may either be a stand-alone unit or incorporated into the hardware of central site server 113. Although it is preferred in the present embodiment that audio recorder 117 is digital, it is foreseeable that other known types of recording devices, as well as those not yet contemplated, may be employed in accordance with the teachings of the present invention. Audio recorder 117 records the conversations performed under the direction of telephone call management system 101. Audio recorder 117 is activated for each call unless the number being called is specifically flagged for no recording or monitoring, such as calls to or from an attorney. Furthermore, audio recorder 117 can monitor multiple telephone lines simultaneously, using a different recorder channel number for trunk lines 111. The recorder channel number further enables the site's staff to identify the call record they wish to review associated with a desired outgoing telephone call. Each user telephone 102 is further associated with a station identification number. The station identification number allows the staff of the institution to identify the particular user telephone 102 a particular call was initiated and conducted from. It is foreseeable that the embodiment described herein supports up to 32 inmate telephone stations 103 and 24 trunk lines 111. However, multiple units 105 may be configured to support up to xxx telephone stations and xxx trunk lines.

Central site server 113 is controlled by software associated with administrative workstation 120. In the preferred embodiment, the administrative workstation 120 is connected to central site server 113 via a local area network (LAN). However, it is foreseeable that other types of electronic connections may be employed. The administrative workstation's 120 software can modify call restrictions for individual users in addition to all telecommunication activity of the institution. Additionally, according to the present example, the software also tracks the inmate's commissary information, such as the account balance if a debit system is being used. Furthermore, depending on the needs of an institution, the database may perform other functions.

A commissary workstation 121 is used in conjunction with the administrative workstation 120 to manage and record inmates' financial transactions. In the preferred embodiment, commissary workstation 121 and administrative workstation 120 are connected to a central site server 113 via a local area network. However, other known connections, or connections not yet contemplated may be utilized. Commissary workstation 121 can also record other financial information, such as the amount spent on collect calls by each inmate, amount spent on debit calls, the total net financial transactions for each user, etc.

Shadow workstation 123 and investigative workstation 125 are also employed in the present embodiment. Shadow workstation 123 and investigative workstation 125 are created via a local area network linked central site server 113 in the present embodiment. Shadow workstation 123 is used by a live operator to monitor telephone calls without detection. It is foreseeable that this function is performed by software integrated with shadow workstation 123. Shadow workstation 123 software provides a means for patching into a call using circuitry without alerting the inmate or called party as to the operator's presence. If the operator finds that a call being monitored is suspicious, the operator may activate the audio recorder 117 to record a portion of an active telephone call. The called party's number may also be flagged in the inmate's profile stored on administrative workstation 120 or central site server 113.

Alternatively, software located on central site server 113 or investigative workstation 125 may be used to passively monitor calls. For example, when certain key phrases are spoken, voice recognition software activates audio recorder 117 via electronic means and alerts the proper authorities that a violation has occurred.

Furthermore, investigative workstation 125 controls other monitoring and security features interfaced in the call system. For example, investigative workstation 125 can be used to access past conversations stored on audio recorder 117. Software on investigative workstation 125 may also be configured to detect if a third party is present during an inmate's conversation. Investigative workstation 125 or central site server 113 may also contain voice recognition software to aid in calling or called party voice authentication. The administrative workstation 120, shadow workstation 123, investigative workstation 125, and commissary workstation 121 may alternatively be combined into one unit. Furthermore, 120, 123, and 120 may be integral within the central site server. It is also foreseeable that 120 may be alternately located off site from the other apparati of the present invention.

While the present invention has been described with reference to the preferred embodiments and several alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A computer-implemented method for restricting access to a call management system, the method comprising the steps of:
   during a registration process by a user of the call management system:
      receiving a first image from the user via a biometric sensing device;
      verifying the first image is indicative of a face using image recognition; and
      associating the verified first image with a user profile and storing the verified first image in a database; and
   during each subsequent access attempt by the user to the call management system to place a call:
      prompting the user to utilize the biometric sensing device to provide a second image;
      determining that a visual characteristic of the second image matches a visual characteristic of the verified first image;
      determining that the visual characteristic of the second image is a statistical match to the visual characteristic of the verified first image; and
      in response to determining that the visual characteristic of the second image is a statistical match to the visual characteristics of the verified first image:
         retrieving voice prompt menu information associated with the user profile;
         selecting a voice prompt menu from a plurality of voice prompt menus based on the retrieved voice prompt menu information;
         playing the selected voice prompt menu for a called party that the user is attempting to contact, wherein the voice prompt menu prompts the called party to supply biometric authentication information; and
         allowing the call in response to receiving and authenticating supplied biometric authentication information from the called party.

2. The method according to claim 1, further comprising:
   during the each subsequent access attempt by the user to the call management system to place a call:
      after the allowing the call to be completed, sampling image data from the call to detect if an unauthorized person is party to the call based on the visual characteristic of the verified first image.

3. The method according to claim 1, wherein the camera is an infrared camera and the first image, the first verified image, and the second image are infrared images.

4. The method according to claim 1, further comprising:
   during the registration process by the user of the call management system:
      assigning an identification to the user; and
      associating the identification with the first image in the database; and
   during the each subsequent access attempt by the user to the call management system to place the call:
      receiving the identification from the user; and
      locating the first image in the database using the identification.

5. The method according to claim 4, further comprising:
   in response to determining that the visual characteristic of the second image is a statistical match to the visual characteristic of the verified first image:
      querying the database with the identification;
      determining whether the user is authorized to place the call based on the querying; and
      allowing or rejecting the call based on the determination.

6. The method according to claim 4, further comprising:
   taking a control action in response to detecting that an unauthorized person is party to the call.

7. The method according to claim 1, further comprising:
   monitoring the access to the call management system by updating the database.

8. The method according to claim 1, further comprising:
   prompting the user to position his/her face within a field of view of the camera,
   wherein the prompting is implemented with a graphical user interface.

9. The method according to claim 1, wherein the visual characteristic of the first image, the visual characteristic of the verified first image, and the visual characteristic of the second image are measures of face architecture.

10. An apparatus for restricting access to a call management system, the apparatus comprising:
a database; and
one or more processors and/or circuits configured to:
register a user, the registering including:
receiving a first image from the user via a biometric sensing device; and
storing the first image in the database; and
authorize or reject-a subsequent call attempt by the user by:
receiving a second image from the user;
verifying that the first image is indicative of a face;
determining that a visual characteristic of the second image matches a visual characteristic of the first image;
in response to determining that the visual characteristic of the second image matches a visual characteristic of the first image,
retrieving voice prompt menu information from the database;
selecting a voice prompt menu from a plurality of voice prompt menus based on the retrieved voice prompt menu information;
playing the selected voice prompt menu for a called party that the user is attempting to contact, wherein the voice prompt menu prompts the called party to supply biometric authentication information; and
authorizing the subsequent call attempt in response to receiving and authenticating supplied biometric authentication information from the called party.

11. The apparatus according to claim 10, wherein the one or more processors and/or circuits are further configured to:
after authorizing the subsequent call attempt, obtain image data of the user during the call;
compare a visual characteristic of the image data of the user during the call to the visual characteristic of the verified first image; and
detect if an unauthorized person is party to the call based on the comparison.

12. The apparatus according to claim 10, wherein the database further includes an identification provided by the caller, the identification being associated with the caller and the first image in the database; and
wherein the one or more processors and/or circuits are further configured to locate the first image using the identification.

13. The apparatus according to claim 10, wherein the one or more processors and/or circuits are further configured to take a control action in response to detecting that an unauthorized person has spoken.

14. The apparatus according to claim 10, wherein the camera is an infrared camera and the first and second images are infrared images.

15. The apparatus according to claim 10, wherein the visual characteristic of the first image and the visual characteristic of the second image are measures of face architecture.

16. A tangible non-transitory computer-readable device having instructions stored thereon that, when executed by at least one computing device, causes the at least one computing device to perform operations comprising:
during a registration process by a user of a call management system:
receiving a first image from the user via a biometric sensing device;
verifying the first image is indicative of a face using image recognition; and
associating the verified first image with a user profile and storing the verified first image in a database; and
during each subsequent access attempt by the user to the call management system to place a call:
prompting the user to utilize the biometric sensing device to provide a second image;
determining that a visual characteristic of the second image matches a visual characteristic of the verified first image;
determining that the visual characteristic of the second image is a statistical match to the visual characteristic of the verified first image; and
in response to determining that the visual characteristic of the second image is a statistical match to the visual characteristics of the verified first image:
retrieving voice prompt menu information associated with the user profile;
selecting a voice prompt menu from a plurality of voice prompt menus based on the retrieved voice prompt menu information;
playing the selected voice prompt menu for a called party that the user is attempting to contact, wherein the voice prompt menu prompts the called party to supply biometric authentication information; and
allowing the call in response to receiving and authenticating supplied biometric authentication information from the called party.

17. The tangible non-transitory computer-readable device of claim 16, the operations further comprising:
during the each subsequent access attempt by the user to the call management system to place a call:
after the allowing the call to be completed, sampling image data from the call to detect if an unauthorized person is party to the call based on the visual characteristic of the verified first image.

18. The tangible non-transitory computer-readable device of claim 16, the operations further comprising:
during the registration process by the user of the call management system:
assigning an identification to the user; and
associating the identification with the first image in the database; and
during the each subsequent access attempt by the user to the call management system to place the call:
receiving the identification from the user; and
locating the first image in the database using the identification.

19. The tangible non-transitory computer-readable device of claim 18, the operations further comprising:
in response to determining that the visual characteristic of the second image is a statistical match to the visual characteristic of the verified first image:
querying the database with the identification;
determining whether the user is authorized to place the call based on the querying; and
allowing or rejecting the call based on the determination.

20. The tangible non-transitory computer-readable device of claim 18, the operations further comprising:

taking a control action in response to detecting that an unauthorized person is party to the call.

* * * * *